US009040728B2

(12) United States Patent
DeLuca et al.

(10) Patent No.: US 9,040,728 B2
(45) Date of Patent: May 26, 2015

(54) CRYSTALLIZATION OF (20R) 19-NOR-24-DIFLUORO-1α,25-DIHYDROXY VITAMIN $D_3$

(71) Applicant: Wisconsin Alumni Research Foundation, Madison, WI (US)

(72) Inventors: Hector F. DeLuca, Deerfield, WI (US); Agnieszka Flores, Madison, WI (US); James B. Thoden, Madison, WI (US); Hazel M. Holden, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/828,223

(22) Filed: Mar. 14, 2013

(65) Prior Publication Data

US 2013/0324751 A1 Dec. 5, 2013

Related U.S. Application Data

(60) Provisional application No. 61/652,949, filed on May 30, 2012.

(51) Int. Cl.
*C07C 401/00* (2006.01)
(52) U.S. Cl.
CPC ............ *C07C 401/00* (2013.01); *C07B 2200/13* (2013.01); *C07C 2101/14* (2013.01); *C07C 2102/24* (2013.01)
(58) Field of Classification Search
CPC .............. C07C 401/00; C07C 2102/24; C07B 2200/13
See application file for complete search history.

(56) References Cited

U.S. PATENT DOCUMENTS

| | | | |
|---|---|---|---|
| 5,086,191 A * | 2/1992 | DeLuca et al. ................ | 552/653 |
| 5,536,713 A | 7/1996 | DeLuca et al. | |
| 5,843,928 A | 12/1998 | DeLuca et al. | |
| 6,462,031 B2 * | 10/2002 | DeLuca et al. ................ | 514/167 |

OTHER PUBLICATIONS

Iwasaki, H.; Miyamoto, Y.; Hosotani, R.; Nakano, Y.; Konno, K.; Takayama, H. "Synthesis and Biological Evaluation of (23R)- and (23S)-24,24-Difluoro-1a,23,25-trihydroxyvitamin D3" Chem. Pharm. Bull. 1998, 46 (12), 1932-1935.*
Norris, J.F. "Experimental Organic Chemistry" McGraw-Hill Book Company. New York. 1924. Ch 1, pp. 1-3.*
Sicinski et al., "Synthesis and Biological Activity of 1alpha, 25-Dihydroxy-18-Norvitamin D3 and 1alpha, 25-Dihydroxy-18, 19-Dinorvitamin D3", Journal of Organic Chemistry, 196, 39(22): 4497-4506.
Wu et al., "A Practical Synthesis of 14-epi-19-nor-1alpha, 25Dihydroxyvitamin D3 Analogues and Their A-ring Epimers", Journal of Organic Chemistry, 2001, 20: 3779-3788.
International Search Report and Written Opinion, PCT International Application No. PCT/US2013/0388889, mailed Jul. 1, 2013.
Andrews et al., "A Direct, Regio- and Stereoselective 1Alpha-Hydroxylation of (5E)-Calciferol Derivatives", Journal of Organic Chemistry, 1986, 51: 1635-1637.
Baggiolini et al., "Stereocontrolled Total Synthesis of 1[alpha],25-Dihydroxycholecaliferol and 1[alpha],25-Dihydroxyergocalciferol", Journal of Organic Chemistry, 1986, 51: 3098-3108.
Calverley et al., "A Biologically Active Vitamin D Metabolite Analogue", Tetrahedron, 1987, 43(20): 4609-4619.
Choudhry et al., "Synthesis of a Biologically Active Vitamin-D2 Metabolite", Journal of Organic Chemistry, 1993, 58:1496-1500.
Lythgoe et al., "Calciferol and its Relatives. Part 22. A Direct Total Synthesis of Vitamin D2 and Vitamin D3", J. Chem. Soc. Perkin I, 1978, 590-595.
Lythgoe, "Synthetic Approaches to Vitamin D and its Relatives", Chem. Soc. Rev., 1983, 9: 449-475.
Paaren et al., "Direct C-1 Hydroxylation of Vitamin D Compounds: Convenient Preparation of 1alpha-Hydroxyvitamin D3,1alpha-Dihydroxyvitamin D3 and 1alpha,Hydroxyvitamin D2", Proc. Natl. Acad. Sci. USA, 1978, 75(5): 2080-2081.
Paaren et al., "Direct C-1 Hydroxylation of Vitamin D3 and Related Compounds", J. Org. Chem., 1980, 45: 3253-3258.
Perlman et al., "Novel Synthesis of 19-Nor-Vitamin D Compounds", Tetrahedron Letters, 1991, 32: 7663-7666.
Nerinckx et al., "An Improved Synthesis of 1Alpha-Hydroxy Vitamin D3", Tetrahedron, 1991, 47(45): 9419-9430.
Sardina et al., "Studies on the Synthesis of Side-Chain Hydroxylated Metabolites of Vitamin D. 2. Stereocontrolled Synthesis of 25-Hydroxyvitamin D2", Journal of Organic Chemistry, 1986, 51: 1264-1269.
Sicinski et al., "New 1alpha,25-Dihydroxy-19-norvitamin D3 Compounds of High Biological Activity: Synthesis and Biological Evaluation of 2-Hydroxymethyl, 2-Methyl, and 2-Methylene Analogs", J. Med. Chem., 1998, 41: 4662-4674.
Sheldrick, "Phase Annealing in SHELX-90: Direct Methods for Larger Structures", Acta Cryst., 1990, A46: 467-473.
Toh et al., "Studies on a Convergent Route to Side-Chain Analogues of Vitamin D:25-Hydroxy-23-oxavitamin D3", Journal of Organic Chemistry, 1983, 48: 1414-1417.
Vanmaele et al., "A Stereocontrolled Partial Synthesis of 1Alpha-Hydroxy Vitamin D3", Tetrahedron Letters, 1982, 23 (9): 995-998.
Vanmaele et al., "1Alpha-Hydroxy Previtamin D3 and its Selective Formation From 1-Keto Previtamin D3", Tetrahedron, 1984, 40(7): 1179-1182.
Vanmaele et al., "An Efficient Synthesis of 1Alpha-25-Dihydroxy Vitamin D3", Tetrahedron, 1985, 41(1): 141-144.

* cited by examiner

*Primary Examiner* — Sean Basquill
*Assistant Examiner* — Andrew S Rosenthal
(74) *Attorney, Agent, or Firm* — Andrus Intellectual Property Law, LLP

(57) ABSTRACT

Disclosed are methods of purifying the compound (20R)-19-nor-24-difluoro-1α,25-dihydroxyvitamin $D_3$ to obtain the compound in crystalline form. The methods typically include the steps of dissolving a product containing the compound in a solvent comprising hexane and 2-propanol, cooling the solvent and dissolved product below ambient temperature for a sufficient amount of time to form a precipitate of crystals, and recovering the crystals.

7 Claims, 1 Drawing Sheet

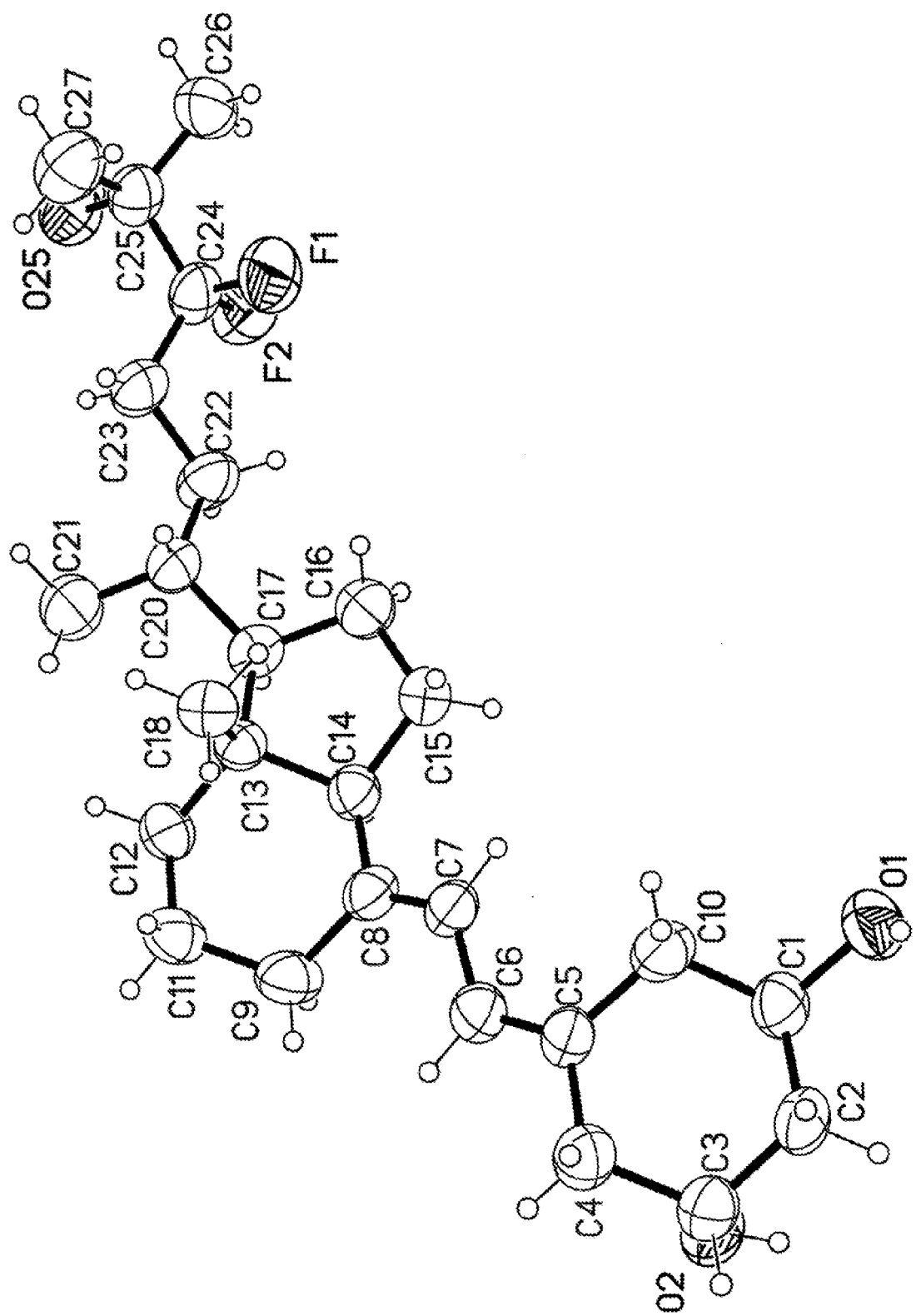

US 9,040,728 B2

CRYSTALLIZATION OF (20R) 19-NOR-24-DIFLUORO-1α,25-DIHYDROXY VITAMIN $D_3$

CROSS-REFERENCE TO RELATED PATENT APPLICATIONS

The present application claims the benefit under 35 U.S.C. §119(e) to U.S. Provisional Patent Application No. 61/652,949, filed on May 30, 2012, the content of which is incorporated herein by reference in its entirety.

STATEMENT REGARDING FEDERALLY SPONSORED RESEARCH OR DEVELOPMENT

This invention was made with government support under DK047814 awarded by the National Institutes of Health. The government has certain rights in the invention.

BACKGROUND

The field of the present invention relates to purification of organic compounds, and more particularly to the purification of the compound (20R)-19-nor-24-difluoro-1α, 25-dihydroxyvitamin $D_3$ (referred to herein as "24F2-DM") by preparing the compound in crystalline form.

Purification of organic compounds, especially those designated for pharmaceutical use, is of considerable importance for chemists synthesizing such compounds. Preparation of the compound usually requires many synthetic steps and, therefore, the final product can be contaminated not only with side-products derived from the last synthetic step of the procedure but also with compounds that were formed in previous steps. Even chromatographic purification, which is a very efficient but relatively time-consuming process, does not usually provide compounds which are sufficiently pure to be used as drugs.

Depending on the method used to synthesize 1α-hydroxyvitamin D compounds, different minor undesirable compounds can accompany the final product. Thus, for example, if direct C-1 hydroxylation of the 5,6-trans geometric isomer of vitamin D is performed, followed by $SeO_2$/NMO oxidation and photochemical irradiation, (see Andrews et al., *J. Org. Chem.* 51, 1635 (1986); Calverley et al., *Tetrahedron* 43, 4609 (1987); Choudry et al., *J. Org. Chem.* 58, 1496 (1993)), the final 1α-hydroxyvitamin D product can be contaminated with 1β-hydroxy- as well as 5,6-trans isomers. If the method consists of C-1 allylic oxidation of the 4-phenyl-1,2,4-triazoline-3,5-dione adduct of the pre-vitamin D compound, followed by cycloreversion of the modified adduct under basic conditions, (see Nevinckx et al., *Tetrahedron* 47, 9419 (1991); Vanmaele et al., *Tetrahedron* 41, 141 (1985) and 40, 1179 (1994); Vanmaele et al., *Tetrahedron Lett.* 23. 995 (1982)), one can expect that the desired 1α-hydroxyvitamin can be contaminated with the pre-vitamin 5(10), 6,8-triene and 1β-hydroxy isomer. One of the most useful C-1 hydroxylation methods, of very broad scope and numerous applications, is the experimentally simple procedure elaborated by Paaren et al., *J. Org. Chem.* 45, 3253 (1980); and *Proc. Natl. Acad. Sci. U.S.A.* 75, 2080 (1978). This method consists of allylic oxidation of 3,5-cyclovitamin D derivatives, readily obtained from the buffered solvolysis of vitamin D tosylates, with $SeO_2$/t-BuOOH and subsequent acid-catalyzed cycloreversion to the desired 1α-hydroxy compounds. Taking into account this synthetic path it is reasonable to assume that the final product can be contaminated with the 1α-hydroxy epimer, the 5,6-trans isomer and the pre-vitamin D form. 1α-hydroxyvitamin $D_4$ is another undesirable contaminant found in 1α-hydroxyvitamin D compounds synthesized from vitamin $D_2$ or from ergosterol. 1α-hydroxyvitamin $D_4$ results from C-1 oxidation of vitamin $D_4$, which in turn is derived from contamination of the commercial ergosterol material. Typically, the final product may contain up to about 1.5% by weight 1α-hydroxyvitamin $D_4$. Thus, a purification technique that would eliminate or substantially reduce the amount of 1α-hydroxyvitamin $D_4$ in the final product to less than about 0.1-0.2% would be highly desirable.

The vitamin D conjugated triene system is not only heat- and light-sensitive but it is also prone to oxidation, leading to the complex mixture of very polar compounds. Oxidation usually happens when a vitamin D compound has been stored for a prolonged time. Other types of processes that can lead to a partial decomposition of vitamin D compounds consist of some water-elimination reactions. The driving force for these reactions is the allylic (1α-) and homoallylic (3β-) position of the hydroxy groups. The presence of such above-mentioned oxidation and elimination products can be easily detected by thin-layer chromatography.

Usually, all 1α-hydroxylatation procedures require at least one chromatographic purification. However, even chromatographically purified 1α-hydroxyvitamin D compounds, although showing consistent spectroscopic data that suggests homogeneity, do not meet the purity criteria required for therapeutic agents that can be orally, parenterally or transdermally administered. Therefore, it is evident that a suitable method of purification of the 1α-hydroxylated vitamin D compound 24F2-DM is required.

SUMMARY

Disclosed herein are methods of purifying 24F2-DM by means of crystallization to obtain 24F2-DM in crystalline form. The solvent plays an important role in the crystallization process, and is typically an individual liquid substance or a suitable mixture of different liquids. For crystallizing 24F2-DM, the most appropriate solvent and/or solvent system is characterized by the following factors:

(1) low toxicity;
(2) low boiling point;
(3) significant dependence of solubility properties with regard to temperature (condition necessary for providing satisfactory crystallization yield); and
(4) relatively low cost.

Interestingly, hexane, so frequently used for crystallization purposes, was found less suitable as the sole solvent for crystallization of 24F2-DM. However, it was found that a mixture of 2-propanol and hexane was most useful for the crystallization of 24F2-DM. In particular, it was determined that a mixture of about 10% to about 20% 2-propanol (v/v) with about 90% to about 80% hexane (v/v) (and preferably 15% 2-propanol (v/v) with about 85% hexane (v/v)) performed well. The 2-propanol/hexane solvent mixture also was easy to remove by evaporation or other well-known methods. In all cases, the crystallization process occurred easily and efficiently. The precipitated crystals were sufficiently large to assure their recovery by filtration or other means, and thus were suitable for x-ray analysis.

Accordingly, the present invention provides a compound having the formula:

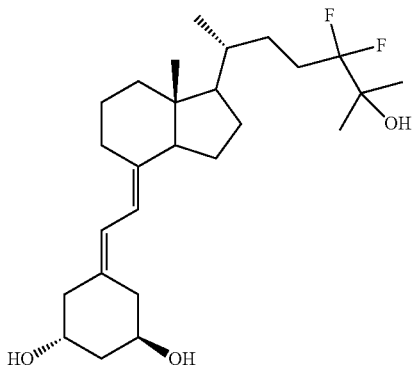 [SMILES: C[C@H](CCC(F)(F)C(C)(C)O)C1CCC2/C(=C/C=C3C[C@@H](O)C[C@H](O)C3)CCC[C@@]21C]

in crystalline form. More specifically, the compound may be referred to as (20R)-19-nor-24-difluoro-1α,25-dihydroxyvitamin $D_3$ or "24F2-DM" in crystalline form.

BRIEF DESCRIPTION OF THE DRAWINGS

FIG. 1 is an illustration of the three dimensional molecular structure for 24F2-DM as defined by the atomic positional parameters discovered and set forth herein.

DETAILED DESCRIPTION

Disclosed herein is the compound (20R)-19-nor-24-difluoro-1α,25-dihydroxyvitamin D3 (24F2-DM) in crystalline form, a pharmacologically important compound, characterized by the formula I shown below:

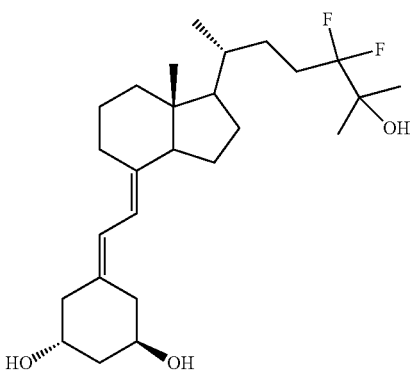 [SMILES: C[C@H](CCC(F)(F)C(C)(C)O)C1CCC2/C(=C/C=C3C[C@@H](O)C[C@H](O)C3)CCC[C@@]21C]

I

Also disclosed are methods of purifying 24F2-DM. The purification technique involves obtaining the 24F2-DM product in crystalline form by utilizing a crystallization procedure wherein the material to be purified is dissolved using as the solvent a mixture comprised of 2-propanol and hexane to obtain 24F2-DM. Preferably the mixture comprises from about 10% to about 20% 2-propanol and about 90% to about 80% hexane, and preferably about 15% 2-propanol and about 85% hexane (by volume). Thereafter, the solvent can be removed by evaporation, with or without vacuum, or other means as is well known, or the resultant crystals may be filtered from the mother liquor. The technique can be used to purify a wide range of final products containing 24F2-DM obtained from any known synthesis thereof, and in varying concentrations, ranging from microgram amounts to kilogram amounts. As is well known to those skilled in this art, the amount of solvent utilized may be modulated according to the amount of 24F2-DM to be purified.

EXAMPLES

The following examples are illustrative and should not be interpreted as limiting the claimed subject matter.

The usefulness and advantages of the present crystallization procedure is shown in the following specific Examples. After crystallization, the precipitated material was observed under a microscope to confirm its crystalline form. Yields of crystals were relatively high and the obtained crystals showed a relatively sharp melting point of 182-183° C. (24F2-DM).

The described crystallization process of the synthetic 24F2-DM product represents a valuable purification method, which can remove most side products derived from the synthetic path. Such impurity is the result of the contamination of starting raw materials. The crystallization process occurred easily and efficiently. The precipitated crystals were sufficiently large to assure their recovery by filtration, or other means, and thus were suitable for x-ray analysis.

Example 1

Crystallization of (20R)-19-nor-24-difluoro-1α25-dihydroxyvitamin $D_3$ (24F2-DM)

Crystallization from 2-Propanol/Hexane.

(20R)-19-nor-24-difluoro-1α,25-dihydroxyvitamin $D_3$ (24F2-DM) (6 mg), was suspended in hexane (3 mL) and then 2-propanol was added dropwise to the suspension. The mixture was heated in a water bath to dissolve the vitamin, then was left at room temperature for about 1 hour, and finally was kept in a refrigerator for about 48 hours. The precipitated crystals were filtered off, washed with a small volume of a cold (0° C.) 2-propanol/hexane (3:1) mixture and dried to give crystalline material. It should be noted that an excess of 2-propanol should be avoided to get the point of saturation, (i.e., only about 1 mole or less of 2-propanol should be added).

Experimental.

A colorless prism-shaped crystal of dimensions 0.56×0.24×0.21 mm was selected for structural analysis. Intensity data were collected using a Bruker AXS Platinum 135 CCD detector controlled with the PROTEUM software suite (Bruker AXS Inc., Madison, Wis.). The x-ray source was CuKα radiation (1.54178 Å) from a Rigaku RU200 x-ray generator equipped with Montel optics, operated at 50 kV and 90 mA. The x-ray data were processed with SAINT version 7.06 A (Bruker AXS Inc.) and internally scaled with SAD-ABS version 2005/1 (Bruker AXS Inc.). The sample was mounted in a quartz capillary and diffraction data collected at 298 K. The intensity data were measured as a series of phi and omega oscillation frames each of 1° for 30-60 sec/frame. The detector was operated in 1024×1024 mode and was positioned 5.0 cm from the sample. Cell parameters were determined from a non-linear least squares fit of 5115 peaks in the range of 3.0<theta<61.5°. The data were merged to form a set of 2949 independent data with R(int)=0.0658.

The monoclinic space group C2 was determined by systematic absences and statistical tests and verified by subsequent refinement. The structure was solved by direct methods and refined by full-matrix least-squares methods on $F^2$, (a) G. M. Sheldrick (1994), SHELXTL Version 5 Reference Manual, Bruker AXS Inc.; (b) *International Tables for Cry-* suallography, Vol. C, Kluwer: Boston (1995). Hydrogen atom positions were determined from difference peaks and ultimately refined by a riding model with idealized geometry. Non-hydrogen atoms were refined with anisotropic displacement parameters. A total of 280 parameters were refined against 1 restraint and 2949 data to give wR2=0.1794 and S=1.027 for weights of $w=1/[s^2(F^2)+(0.1196P)^2]$, where $P=[F_o^2+2F^2]/3$. The final R(F) was 0.0669 for the 2949 observed data. The largest shift/s.u. was 0.001 in the final refinement cycle and the final difference map had maxima and minima of 0.228 and −0.200 e/Å$_3$, respectively. The absolute structure was determined by refinement of the Flack parameter, H. D. Flack, *Acta Cryst. A*, vol. 39, 876-881 (1983).

The three dimensional structure of 24F2-DM as defined by the following physical data and atomic positional parameters described and calculated herein (Tables 1-8) is illustrated in FIG. 1.

TABLE 1

Crystal data and structure refinement for 24F2-DM.

| | |
|---|---|
| Identification code | 2007 feb. 11 |
| Empirical formula | C26H42F2O3 |
| Formula weight | 440.60 |
| Temperature | 298(2) K |
| Wavelength | 1.54178 Å |
| Crystal system | Monoclinic |
| Space group | C2 |
| Unit cell dimensions | a = 23.882(5) Å   α = 90° |
| | b = 6.1654(12) Å   β = 121.83(3)° |
| | c = 19.632(4) Å   γ = 90° |
| Volume | 2456.0(8) Å$^3$ |
| Z | 4 |
| Density (calculated) | 1.192 Mg/m$^3$ |
| Absorption coefficient | 0.696 mm$^{-1}$ |
| F(000) | 960 |
| Crystal size | 0.70 × 0.20 × 0.01 mm |
| Theta range for data collection | 2.65 to 62.79° |
| Limiting indices | −27 < h < 26, −7 < k < 5, −22 < l < 20 |
| Reflections collected | 5115 |
| Independent reflections | 2949 (R(int) = 0.0658) |
| Completeness to Theta = 62.79 | 97.4% |
| Max. and min. transmission | 0.9931 and 0.6415 |
| Refinement method | Full-matrix least-squares on F$^2$ |
| Data/restraints/parameters | 2949/1/280 |
| Goodness-of-fit on F$^2$ | 1.027 |
| Final R indices [I > 2σ(I)] | R1 = 0.0669, wR2 = 0.1794 |
| R indices (all data) | R1 = 0.0812, wR2 = 0.1938 |
| Largest diff. peak and hole | 0.228 and −0.200 e$^-$/Å$^3$ |

TABLE 2

Atomic coordinates (Å$^2$ × 10$^4$) and equivalent isotropic displacement parameters (Å$^2$ × 10$^3$) for 24F2-DM U(eq) is defined as one third of the trace of the orthogonalized Uij tensor.

| | x | y | z | U(eq) |
|---|---|---|---|---|
| O(1) | 7791(2) | 7357(6) | 9362(2) | 65(1) |
| O(2) | 8325(2) | 13611(6) | 10408(2) | 67(1) |
| C(13) | 9071(2) | 14375(7) | 6662(2) | 46(1) |
| F(2) | 7592(1) | 11566(8) | 2797(2) | 85(1) |
| C(5) | 8998(2) | 11683(8) | 9616(2) | 51(1) |
| F(1) | 8124(2) | 8914(7) | 3583(2) | 97(1) |
| C(14) | 8581(2) | 14018(8) | 6948(2) | 50(1) |
| C(3) | 8802(2) | 11904(8) | 10755(2) | 56(1) |
| C(2) | 8472(2) | 9722(8) | 10504(3) | 58(1) |
| O(25) | 8404(2) | 11739(8) | 2212(2) | 75(1) |
| C(4) | 9288(2) | 12202(10) | 10482(5) | 59(1) |
| C(8) | 8875(2) | 14304(8) | 7829(2) | 50(1) |
| C(10) | 8646(3) | 9530(8) | 9360(3) | 60(1) |
| C(11) | 9669(3) | 17024(9) | 7815(2) | 64(1) |
| C(1) | 8146(2) | 9375(8) | 9611(3) | 54(1) |

TABLE 2-continued

Atomic coordinates (Å$^2$ × 10$^4$) and equivalent isotropic displacement parameters (Å$^2$ × 10$^3$) for 24F2-DM U(eq) is defined as one third of the trace of the orthogonalized Uij tensor.

| | x | y | z | U(eq) |
|---|---|---|---|---|
| C(7) | 8823(2) | 12846(8) | 8292(2) | 52(1) |
| C(6) | 9065(2) | 13067(8) | 9137(3) | 54(1) |
| C(12) | 9342(2) | 16680(8) | 6912(2) | 57(1) |
| C(18) | 9627(2) | 12723(8) | 7044(2) | 54(1) |
| C(15) | 8230(2) | 11923(10) | 6537(3) | 61(1) |
| C(17) | 8612(2) | 13954(8) | 5760(2) | 52(1) |
| C(9) | 9199(3) | 16504(9) | 8103(3) | 64(1) |
| C(20) | 8910(2) | 13579(9) | 5242(2) | 57(1) |
| C(27) | 9084(3) | 9004(14) | 3081(3) | 88(2) |
| C(16) | 8177(2) | 12029(10) | 5721(2) | 64(1) |
| C(23) | 8654(2) | 12262(10) | 3874(3) | 68(2) |
| C(24) | 8202(2) | 10696(10) | 3226(3) | 63(1) |
| C(25) | 8401(2) | 9895(10) | 2645(3) | 63(1) |
| C(22) | 8382(2) | 12996(12) | 4384(2) | 71(2) |
| C(26) | 7907(3) | 8192(12) | 2071(3) | 82(2) |
| C(21) | 9300(4) | 15514(14) | 5254(3) | 99(2) |

TABLE 3

Bond lengths [Å] for 24F2-DM.

| | |
|---|---|
| O(1)—C(1) | 1.439(6) |
| O(1)—H(1A) | 0.8200 |
| O(2)—C(3) | 1.432(6) |
| O(2)—H(2A) | 0.8200 |
| C(13)—C(18) | 1.521(6) |
| C(13)—C(17) | 1.537(6) |
| C(13)—C(12) | 1.531(6) |
| C(13)—C(14) | 1.558(6) |
| F(2)—C(24) | 1.353(6) |
| C(5)—C(6) | 1.341(7) |
| C(5)—C(4) | 1.493(6) |
| C(5)—C(10) | 1.508(7) |
| F(1)—C(24) | 1.368(7) |
| C(14)—C(8) | 1.494(6) |
| C(14)—C(15) | 1.519(7) |
| C(14)—H(14A) | 0.9800 |
| C(3)—C(2) | 1.505(7) |
| C(3)—C(4) | 1.524(6) |
| C(3)—H(3A) | 0.9800 |
| C(2)—C(1) | 1.511(6) |
| C(2)—H(2B) | 0.9700 |
| O(2)—H(2C) | 0.9700 |
| O(25)—C(25) | 1.422(7) |
| O(25)—H(25A) | 0.8200 |
| C(4)—H(4A) | 0.9700 |
| C(4)—H(4B) | 0.9700 |
| C(8)—C(7) | 1.330(6) |
| C(8)—C(9) | 1.513(7) |
| C(10)—C(1) | 1.517(6) |
| C(10)—H(10A) | 0.9700 |
| C(10)—H(10B) | 0.9700 |
| C(11)—C(9) | 1.532(7) |
| C(11)—C(12) | 1.529(6) |
| C(11)—H(11A) | 0.9700 |
| C(11)—H(11B) | 0.9700 |
| C(1)—H(1B) | 0.9800 |
| C(7)—C(6) | 1.446(6) |
| C(7)—H(7A) | 0.9300 |
| C(6)—H(6A) | 0.9300 |
| C(12)—H(12A) | 0.9700 |
| C(12)—H(12B) | 0.9700 |
| C(18)—H(18A) | 0.9600 |
| C(18)—H(18B) | 0.9600 |
| C(18)—H(18C) | 0.9600 |
| C(15)—C(16) | 1.541(6) |
| C(15)—H(15A) | 0.9700 |
| C(15)—H(15B) | 0.9700 |
| C(17)—C(20) | 1.536(6) |
| C(17)—C(16) | 1.552(7) |
| C(17)—H(17A) | 0.9800 |

TABLE 3-continued

Bond lengths [Å] for 24F2-DM.

| | |
|---|---|
| C(9)—H(9A) | 0.9700 |
| C(9)—H(9B) | 0.9700 |
| C(20)—C(21) | 1.506(8) |
| C(20)—C(22) | 1.522(6) |
| C(20)—H(20A) | 0.9800 |
| C(27)—C(25) | 1.489(8) |
| C(27)—H(27A) | 0.9600 |
| C(27)—H(27B) | 0.9600 |
| C(27)—H(27C) | 0.9600 |
| C(16)—H(16A) | 0.9700 |
| C(16)—H(16B) | 0.9700 |
| C(23)—C(24) | 1.505(7) |
| C(23)—C(22) | 1.520(6) |
| C(23)—H(23A) | 0.9700 |
| C(23)—H(23B) | 0.9700 |
| C(24)—C(25) | 1.530(7) |
| C(25)—C(26) | 1.537(8) |
| C(22)—H(22A) | 0.9700 |
| C(22)—H(22B) | 0.9700 |
| C(26)—H(26A) | 0.9600 |
| C(26)—H(26B) | 0.9600 |
| C(26)—H(26C) | 0.9600 |
| C(21)—H(21A) | 0.9600 |
| C(21)—H(21B) | 0.9600 |
| C(21)—H(21C) | 0.9600 |

TABLE 4

Bond angles [°] for 24F2-DM.

| | |
|---|---|
| C(1)—O(1)—H(1A) | 109.5 |
| C(3)—O(2)—H(2A) | 109.5 |
| C(18)—C(13)—C(17) | 111.2(4) |
| C(18)—C(13)—C(12) | 110.6(4) |
| C(17)—C(13)—C(12) | 116.8(4) |
| C(18)—C(13)—C(14) | 110.8(3) |
| C(17)—C(13)—C(14) | 100.1(3) |
| C(12)—C(13)—C(14) | 106.6(3) |
| C(6)—C(5)—C(4) | 120.5(5) |
| C(6)—C(5)—C(10) | 125.2(4) |
| C(4)—C(5)—C(10) | 114.3(4) |
| C(8)—C(14)—C(15) | 120.4(4) |
| C(8)—C(14)—C(13) | 114.5(3) |
| C(15)—C(14)—C(13) | 103.7(3) |
| C(8)—C(14)—H(14A) | 105.7 |
| C(15)—C(14)—H(14A) | 105.7 |
| C(13)—C(14)—H(14A) | 105.7 |
| O(2)—C(3)—C(2) | 110.7(3) |
| O(2)—C(3)—C(4) | 107.7(4) |
| C(2)—C(3)—C(4) | 110.9(4) |
| O(2)—C(3)—H(3A) | 109.2 |
| C(2)—C(3)—H(3A) | 109.2 |
| C(4)—C(3)—H(3A) | 109.2 |
| C(1)—C(2)—C(3) | 111.5(4) |
| C(1)—C(2)—H(2B) | 109.3 |
| C(3)—C(2)—H(2B) | 109.3 |
| C(1)—C(2)—H(2C) | 109.3 |
| C(3)—C(2)—H(2C) | 109.3 |
| H(2B)—C(2)—H(2C) | 108.0 |
| C(25)—O(25)—H(25A) | 109.5 |
| C(5)—C(4)—C(3) | 113.2(4) |
| C(5)—C(4)—H(4A) | 108.9 |
| C(3)—C(4)—H(4A) | 108.9 |
| C(5)—C(4)—H(4B) | 108.9 |
| C(3)—C(4)—H(4B) | 108.9 |
| H(4A)—C(4)—H(4B) | 107.8 |
| C(7)—C(8)—C(14) | 123.7(4) |
| C(7)—C(8)—C(9) | 125.2(4) |
| C(14)—C(8)—C(9) | 111.0(4) |
| C(5)—C(10)—C(1) | 110.0(4) |
| C(5)—C(10)—H(10A) | 109.7 |
| C(1)—C(10)—H(10A) | 109.7 |
| C(5)—C(10)—H(10B) | 109.7 |
| C(1)—C(10)—H(10B) | 109.7 |
| H(10A)—C(10)—H(10B) | 108.2 |

TABLE 4-continued

Bond angles [°] for 24F2-DM.

| | |
|---|---|
| C(9)—C(11)—C(12) | 111.8(4) |
| C(9)—C(11)—H(11A) | 109.3 |
| C(12)—C(11)—H(11A) | 109.3 |
| C(9)—C(11)—H(11B) | 109.2 |
| C(12)—C(11)—H(11B) | 109.3 |
| H(11A)—C(11)—H(11B) | 107.9 |
| O(1)—C(1)—C(2) | 111.6(4) |
| O(1)—C(1)—C(10) | 111.5(4) |
| C(2)—C(1)—C(10) | 110.9(4) |
| O(1)—C(1)—H(1B) | 107.5 |
| C(2)—C(1)—H(1B) | 107.5 |
| C(10)—C(1)—H(1B) | 107.5 |
| C(8)—C(7)—C(6) | 126.6(5) |
| C(8)—C(7)—H(7A) | 116.7 |
| C(6)—C(7)—H(7A) | 116.7 |
| C(5)—C(6)—C(7) | 128.4(5) |
| C(5)—C(6)—H(6A) | 115.8 |
| C(7)—C(6)—H(6A) | 115.8 |
| C(11)—C(12)—C(13) | 111.8(4) |
| C(11)—C(12)—H(12A) | 109.2 |
| C(13)—C(12)—H(12A) | 109.2 |
| C(11)—C(12)—H(12B) | 109.2 |
| C(13)—C(12)—H(12B) | 109.2 |
| H(12A)—C(12)—H(12B) | 107.9 |
| C(13)—C(18)—H(18A) | 109.5 |
| C(13)—C(18)—H(18B) | 109.5 |
| H(18A)—C(18)—H(18B) | 109.5 |
| C(13)—C(18)—H(18C) | 109.5 |
| H(18A)—C(18)—H(18C) | 109.5 |
| H(18B)—C(18)—H(18C) | 109.5 |
| C(14)—C(15)—C(16) | 103.7(4) |
| C(14)—C(15)—H(15A) | 111.0 |
| C(16)—C(15)—H(15A) | 111.0 |
| C(14)—C(15)—H(15B) | 111.0 |
| C(16)—C(15)—H(15B) | 111.0 |
| H(15A)—C(15)—H(15B) | 109.0 |
| C(13)—C(17)—C(20) | 119.4(4) |
| C(13)—C(17)—C(16) | 103.8(3) |
| C(20)—C(17)—C(16) | 112.6(4) |
| C(13)—C(17)—H(17A) | 106.8 |
| C(20)—C(17)—H(17A) | 106.8 |
| C(16)—C(17)—H(17A) | 106.8 |
| C(8)—C(9)—C(11) | 113.2(4) |
| C(8)—C(9)—H(9A) | 108.9 |
| C(11)—C(9)—H(9A) | 108.9 |
| C(8)—C(9)—H(9B) | 108.9 |
| C(11)—C(9)—H(9B) | 108.9 |
| H(9A)—C(9)—H(9B) | 107.8 |
| C(21)—C(20)—C(22) | 110.4(4) |
| C(21)—C(20)—C(17) | 111.7(4) |
| C(22)—C(20)—C(17) | 111.5(4) |
| C(21)—C(20)—H(20A) | 107.7 |
| C(22)—C(20)—H(20A) | 107.7 |
| C(17)—C(20)—H(20A) | 107.7 |
| C(25)—C(27)—H(27A) | 109.5 |
| C(25)—C(27)—H(27B) | 109.5 |
| H(27A)—C(27)—H(27B) | 109.5 |
| C(25)—C(27)—H(27C) | 109.5 |
| H(27A)—C(27)—H(27C) | 109.5 |
| H(27B)—C(27)—H(27C) | 109.5 |
| C(15)—C(16)—C(17) | 107.2(4) |
| C(15)—C(16)—H(16A) | 110.3 |
| C(17)—C(16)—H(16A) | 110.3 |
| C(15)—C(16)—H(16B) | 110.3 |
| C(17)—C(16)—H(16B) | 110.3 |
| H(16A)—C(16)—H(16B) | 108.5 |
| C(24)—C(23)—C(22) | 112.5(4) |
| C(24)—C(23)—H(23A) | 109.1 |
| C(22)—C(23)—H(23A) | 109.1 |
| C(24)—C(23)—H(23B) | 109.1 |
| C(22)—C(23)—H(23B) | 109.1 |
| H(23A)—C(23)—H(23B) | 107.8 |
| F(2)—C(24)—F(1) | 104.1(4) |
| F(2)—C(24)—C(23) | 109.2(5) |
| F(1)—C(24)—C(23) | 108.2(4) |
| F(2)—C(24)—C(25) | 108.7(3) |
| F(1)—C(24)—C(25) | 107.6(5) |
| C(23)—C(24)—C(25) | 118.1(4) |

TABLE 4-continued

Bond angles [°] for 24F2-DM.

| | |
|---|---|
| O(25)—C(25)—C(27) | 106.9(5) |
| O(25)—C(25)—C(24) | 106.8(5) |
| C(27)—C(25)—C(24) | 111.5(4) |
| O(25)—C(25)—C(26) | 110.6(4) |
| C(27)—C(25)—C(26) | 110.8(5) |
| C(24)—C(25)—C(26) | 110.2(4) |
| C(23)—C(22)—C(20) | 114.0(4) |
| C(23)—C(22)—H(22A) | 108.7 |
| C(20)—C(22)—H(22A) | 108.7 |
| C(23)—C(22)—H(22B) | 108.7 |
| C(20)—C(22)—H(22B) | 108.7 |
| H(22A)—C(22)—H(22B) | 107.6 |
| C(25)—C(26)—H(26A) | 109.5 |
| C(25)—C(26)—H(26B) | 109.5 |
| H(26A)—C(26)—H(26B) | 109.5 |
| C(25)—C(26)—H(26C) | 109.5 |
| H(26A)—C(26)—H(26C) | 109.5 |
| H(26B)—C(26)—H(26C) | 109.5 |
| C(20)—C(21)—H(21A) | 109.5 |
| C(20)—C(21)—H(21B) | 109.5 |
| H(21A)—C(21)—H(21B) | 109.5 |
| C(20)—C(21)—H(21C) | 109.5 |
| H(21A)—C(21)—H(21C) | 109.5 |
| H(21B)—C(21)—H(21C) | 109.5 |

TABLE 5

Anisotropic displacement parameters ($Å^2 \times 10^3$) for 24F2-DM. The anisotropic displacement factor exponent takes the form: $-2\pi^2[h^2 a^{*2} U_{11} + \ldots + 2hka^*b^*U_{12}]$.

| | U11 | U22 | U33 | U23 | U13 | U12 |
|---|---|---|---|---|---|---|
| O(1) | 75 (2) | 56 (2) | 64 (2) | 0 (2) | 37 (2) | −12 (2) |
| O(2) | 85 (2) | 55 (2) | 82 (2) | 4 (2) | 57 (2) | 1 (2) |
| C(13) | 53 (2) | 40 (2) | 49 (2) | 2 (2) | 30 (2) | 3 (2) |
| F(2) | 60 (2) | 125 (3) | 63 (2) | −17 (2) | 28 (1) | 1 (2) |
| C(5) | 55 (2) | 52 (3) | 58 (2) | −1 (2) | 37 (2) | −4 (2) |
| F(1) | 127 (3) | 100 (3) | 91 (2) | 3 (2) | 75 (2) | −28 (2) |
| C(14) | 54 (2) | 44 (2) | 58 (2) | 2 (2) | 34 (2) | 0 (2) |
| C(3) | 62 (2) | 56 (3) | 54 (2) | 4 (2) | 34 (2) | −1 (2) |
| C(2) | 63 (2) | 54 (3) | 58 (2) | 11 (2) | 38 (2) | −1 (2) |
| O(25) | 90 (2) | 83 (3) | 60 (2) | 6 (2) | 45 (2) | −5 (2) |
| C(4) | 56 (2) | 72 (3) | 49 (2) | 2 (2) | 28 (2) | −4 (2) |
| C(8) | 57 (2) | 47 (3) | 59 (2) | 1 (2) | 38 (2) | 3 (2) |
| C(10) | 80 (2) | 54 (3) | 62 (2) | −1 (2) | 48 (2) | −1 (3) |
| C(11) | 90 (3) | 49 (3) | 56 (2) | −4 (2) | 40 (2) | −17 (2) |
| C(1) | 63 (2) | 45 (3) | 61 (2) | 8 (2) | 37 (2) | 0 (2) |
| C(7) | 62 (2) | 50 (3) | 58 (2) | −2 (2) | 42 (2) | −3 (2) |
| C(6) | 56 (2) | 52 (3) | 62 (2) | −1 (2) | 36 (2) | 0 (2) |
| C(12) | 71 (3) | 42 (3) | 63 (2) | 0 (2) | 40 (2) | −9 (3) |
| C(18) | 55 (2) | 53 (3) | 52 (2) | −1 (2) | 26 (2) | 3 (2) |
| C(15) | 63 (2) | 66 (3) | 67 (2) | −6 (3) | 42 (2) | −12 (3) |
| C(17) | 57 (2) | 52 (3) | 50 (2) | 1 (2) | 31 (2) | 5 (2) |
| C(9) | 94 (3) | 46 (3) | 59 (2) | −9 (2) | 44 (2) | −6 (3) |
| C(20) | 58 (2) | 67 (3) | 52 (2) | −5 (2) | 32 (2) | −5 (2) |
| C(27) | 81 (3) | 109 (6) | 76 (3) | 6 (4) | 43 (3) | 8 (4) |
| C(16) | 69 (2) | 66 (3) | 59 (2) | −3 (2) | 35 (2) | −6 (3) |
| C(23) | 70 (3) | 89 (4) | 53 (2) | −11 (2) | 39 (2) | −10 (3) |
| C(24) | 61 (3) | 85 (4) | 46 (2) | 1 (2) | 30 (2) | −7 (3) |
| C(25) | 64 (3) | 73 (4) | 55 (2) | 3 (3) | 33 (2) | −4 (3) |
| C(22) | 66 (3) | 98 (4) | 49 (2) | −8 (3) | 31 (2) | −1 (3) |
| C(26) | 95 (4) | 80 (4) | 75 (3) | −13 (3) | 48 (3) | −19 (3) |
| C(21) | 122 (5) | 124 (6) | 75 (3) | −26 (4) | 68 (3) | −49 (5) |

TABLE 6

Hydrogen coordinates ($Å^2 \times 10^4$) and isotropic displacement parameters ($Å^2 \times 10^3$) for 24F2-DM.

| | x | y | z | U(eq) |
|---|---|---|---|---|
| H(1A) | 7993 | 6436 | 9709 | 98 |
| H(2A) | 8012 | 13327 | 10455 | 101 |
| H(14A) | 8249 | 15164 | 6691 | 60 |
| H(3A) | 9039 | 12019 | 11341 | 67 |
| H(2B) | 8797 | 8593 | 10787 | 66 |
| H(2C) | 8143 | 9613 | 10650 | 66 |
| H(25A) | 8055 | 11798 | 1779 | 113 |
| H(4A) | 9440 | 13693 | 10577 | 71 |
| H(4B) | 9667 | 11276 | 10802 | 71 |
| H(10A) | 8964 | 8360 | 9604 | 73 |
| H(10B) | 8424 | 9384 | 8782 | 73 |
| H(11A) | 10056 | 16104 | 8096 | 77 |
| H(11B) | 9813 | 18520 | 7945 | 77 |
| H(1B) | 7826 | 10546 | 9341 | 65 |
| H(7A) | 8610 | 11555 | 8049 | 62 |
| H(6A) | 9297 | 14334 | 9379 | 65 |
| H(12A) | 9661 | 16953 | 6760 | 68 |
| H(12B) | 8984 | 17711 | 6630 | 68 |
| H(18A) | 9923 | 12972 | 6860 | 82 |
| H(18B) | 9447 | 11287 | 6895 | 82 |
| H(18C) | 9862 | 12868 | 7616 | 82 |
| H(15A) | 7797 | 11855 | 6468 | 73 |
| H(15B) | 8484 | 10670 | 6843 | 73 |
| H(17A) | 8321 | 15218 | 5536 | 63 |
| H(9A) | 9443 | 16555 | 8684 | 77 |
| H(9B) | 8860 | 17610 | 7905 | 77 |
| H(20A) | 9214 | 12348 | 5470 | 69 |
| H(27A) | 9385 | 10090 | 3436 | 132 |
| H(27B) | 9202 | 8588 | 2702 | 132 |
| H(27C) | 9104 | 7759 | 3387 | 132 |
| H(16A) | 7722 | 12257 | 5293 | 76 |
| H(16B) | 8331 | 10685 | 5618 | 76 |
| H(23A) | 8721 | 13521 | 3629 | 81 |
| H(23B) | 9079 | 11576 | 4216 | 81 |
| H(22A) | 8110 | 11847 | 4395 | 85 |
| H(22B) | 8102 | 14250 | 4132 | 123 |
| H(26A) | 7472 | 8808 | 1788 | 123 |
| H(26B) | 7913 | 6956 | 2373 | 123 |
| H(26C) | 8025 | 7751 | 1695 | 123 |
| H(21A) | 9629 | 15868 | 5799 | 148 |
| H(21B) | 9010 | 16728 | 5007 | 148 |
| H(21C) | 9511 | 15179 | 4964 | 148 |

TABLE 7

Torsion angles [deg] for 24F2-DM.

| | |
|---|---|
| C(18)—C(13)—C(14)—C(8) | 62.4(5) |
| C(17)—C(13)—C(14)—C(8) | 179.8(4) |
| C(12)—C(13)—C(14)—C(8) | −58.1(5) |
| C(18)—C(13)—C(14)—C(15) | −70.8(4) |
| C(17)—C(13)—C(14)—C(15) | 46.7(4) |
| C(12)—C(13)—C(14)—C(15) | 168.7(4) |
| O(2)—C(3)—C(2)—C(1) | 64.7(5) |
| C(4)—C(3)—C(2)—C(1) | −54.8(5) |
| C(6)—C(5)—C(4)—C(3) | 130.9(5) |
| C(10)—C(5)—C(4)—C(3) | −49.6(6) |
| O(2)—C(3)—C(4)—C(5) | −71.4(5) |
| C(2)—C(3)—C(4)—C(5) | 49.9(6) |
| C(15)—C(14)—C(8)—C(7) | −3.6(7) |
| C(13)—C(14)—C(8)—C(7) | −128.4(5) |
| C(15)—C(14)—C(8)—C(9) | 179.7(4) |
| C(13)—C(14)—C(8)—C(9) | 54.9(5) |
| C(6)—C(5)—C(10)—C(1) | −128.4(5) |
| C(4)—C(5)—C(10)—C(1) | 52.1(5) |
| C(3)—C(2)—C(1)—O(1) | −175.9(4) |
| C(3)—C(2)—C(1)—C(10) | 59.1(6) |
| C(5)—C(10)—C(1)—O(1) | 178.8(3) |
| C(5)—C(10)—C(1)—C(2) | −56.1(5) |
| C(14)—C(8)—C(7)—C(6) | −176.5(4) |
| C(9)—C(8)—C(7)—C(6) | −0.3(7) |
| C(4)—C(5)—C(6)—C(7) | 179.8(4) |

TABLE 7-continued

Torsion angles [deg] for 24F2-DM.

| | |
|---|---|
| C(10)—C(5)—C(6)—C(7) | 0.3(8) |
| C(8)—C(7)—C(6)—C(5) | 176.8(5) |
| C(9)—C(11)—C(12)—C(13) | −56.0(6) |
| C(18)—C(13)—C(12)—C(11) | −63.4(5) |
| C(17)—C(13)—C(12)—C(11) | 168.1(4) |
| C(14)—C(13)—C(12)—C(11) | 57.2(5) |
| C(8)—C(14)—C(15)—C(16) | −164.9(4) |
| C(13)—C(14)—C(15)—C(16) | −35.2(5) |
| C(18)—C(13)—C(17)—C(20) | −48.2(6) |
| C(12)—C(13)—C(17)—C(20) | 80.1(5) |
| C(14)—C(13)—C(17)—C(20) | −165.3(4) |
| C(18)—C(13)—C(17)—C(16) | 78.2(4) |
| C(12)—C(13)—C(17)—C(16) | −153.6(4) |
| C(14)—C(13)—C(17)—C(16) | −39.0(4) |
| C(7)—C(8)—C(9)—C(11) | 133.5(5) |
| C(14)—C(8)—C(9)—C(11) | −49.9(5) |
| C(12)—C(11)—C(9)—C(8) | 51.1(6) |
| C(13)—C(17)—C(20)—C(21) | −61.0(6) |
| C(16)—C(17)—C(20)—C(21) | 177.0(4) |
| C(13)—C(17)—C(20)—C(22) | 175.0(5) |
| C(16)—C(17)—C(20)—C(22) | 53.0(6) |
| C(14)—C(15)—C(16)—C(17) | 10.4(5) |
| C(13)—C(17)—C(16)—C(15) | 18.5(5) |
| C(20)—C(17)—C(16)—C(15) | 149.0(4) |
| C(22)—C(23)—C(24)—F(2) | 52.8(6) |
| C(22)—C(23)—C(24)—F(1) | −60.0(6) |
| C(22)—C(23)—C(24)—C(25) | 177.5(5) |
| F(2)—C(24)—C(25)—O(25) | 61.0(5) |
| F(1)—C(24)—C(25)—O(25) | 173.2(4) |
| C(23)—C(24)—C(25)—O(25) | −64.0(5) |
| F(2)—C(24)—C(25)—C(27) | 177.4(5) |
| F(1)—C(24)—C(25)—C(27) | −70.4(6) |
| C(23)—C(24)—C(25)—C(27) | 52.4(7) |
| F(2)—C(24)—C(25)—C(26) | −59.1(6) |
| F(1)—C(24)—C(25)—C(26) | 53.1(5) |
| C(23)—C(24)—C(25)—C(26) | 175.9(5) |
| C(24)—C(23)—C(22)—C(20) | 150.8(5) |
| C(21)—C(20)—C(22)—C(23) | 64.3(7) |
| C(17)—C(20)—C(22)—C(23) | −170.9(5) |

TABLE 8

Observed and calculated structure factors for 24F2-DM.

| h | k | l | 10Fo | 10Fc | 10s |
|---|---|---|---|---|---|
| 1 | −7 | 0 | 41 | 42 | 4 |
| 3 | −7 | 0 | 38 | 34 | 6 |
| 0 | −6 | 0 | 53 | 41 | 8 |
| 2 | −6 | 0 | 43 | 53 | 10 |
| 4 | −6 | 0 | 11 | 27 | 10 |
| 6 | −6 | 0 | 63 | 68 | 4 |
| 10 | −6 | 0 | 0 | 31 | 1 |
| 1 | −5 | 0 | 65 | 57 | 6 |
| 3 | −5 | 0 | 310 | 315 | 8 |
| 5 | −5 | 0 | 131 | 133 | 8 |
| 7 | −5 | 0 | 143 | 185 | 7 |
| 9 | −5 | 0 | 23 | 18 | 23 |
| 11 | −5 | 0 | 36 | 47 | 8 |
| 13 | −5 | 0 | 91 | 67 | 10 |
| 15 | −5 | 0 | 82 | 62 | 10 |
| 0 | −4 | 0 | 683 | 673 | 48 |
| 2 | −4 | 0 | 87 | 87 | 4 |
| 4 | −4 | 0 | 282 | 277 | 6 |
| 6 | −4 | 0 | 31 | 27 | 8 |
| 8 | −4 | 0 | 0 | 13 | 1 |
| 10 | −4 | 0 | 59 | 60 | 8 |
| 12 | −4 | 0 | 81 | 99 | 10 |
| 14 | −4 | 0 | 14 | 30 | 14 |
| 16 | −4 | 0 | 64 | 55 | 5 |
| 18 | −4 | 0 | 55 | 51 | 16 |
| 1 | −3 | 0 | 313 | 323 | 15 |
| 3 | −3 | 0 | 73 | 82 | 5 |
| 7 | −3 | 0 | 185 | 179 | 6 |
| 9 | −3 | 0 | 258 | 262 | 7 |
| 11 | −3 | 0 | 211 | 177 | 6 |
| 13 | −3 | 0 | 88 | 89 | 6 |
| 15 | −3 | 0 | 55 | 68 | 7 |
| 17 | −3 | 0 | 78 | 92 | 5 |
| 19 | −3 | 0 | 71 | 65 | 6 |
| 21 | −3 | 0 | 28 | 28 | 8 |
| 0 | −2 | 0 | 1114 | 1129 | 40 |
| 2 | −2 | 0 | 208 | 206 | 13 |
| 4 | −2 | 0 | 795 | 756 | 34 |
| 6 | −2 | 0 | 512 | 529 | 28 |
| 8 | −2 | 0 | 210 | 179 | 11 |
| 10 | −2 | 0 | 246 | 231 | 8 |
| 12 | −2 | 0 | 174 | 177 | 6 |
| 14 | −2 | 0 | 85 | 84 | 5 |
| 16 | −2 | 0 | 87 | 99 | 7 |
| 18 | −2 | 0 | 41 | 48 | 14 |
| 20 | −2 | 0 | 114 | 102 | 8 |
| 22 | −2 | 0 | 31 | 33 | 14 |
| 1 | −1 | 0 | 1222 | 1167 | 35 |
| 3 | −1 | 0 | 1786 | 1655 | 83 |
| 5 | −1 | 0 | 1028 | 1026 | 42 |
| 7 | −1 | 0 | 657 | 823 | 39 |
| 9 | −1 | 0 | 202 | 252 | 11 |
| 11 | −1 | 0 | 128 | 136 | 10 |
| 13 | −1 | 0 | 46 | 36 | 12 |
| 15 | −1 | 0 | 225 | 216 | 7 |
| 17 | −1 | 0 | 149 | 139 | 5 |
| 19 | −1 | 0 | 41 | 51 | 17 |
| 21 | −1 | 0 | 42 | 40 | 14 |
| 2 | 0 | 0 | 866 | 876 | 44 |
| 4 | 0 | 0 | 2245 | 2228 | 115 |
| 6 | 0 | 0 | 185 | 242 | 10 |
| 8 | 0 | 0 | 305 | 354 | 16 |
| 10 | 0 | 0 | 38 | 24 | 21 |
| 12 | 0 | 0 | 306 | 301 | 11 |
| 14 | 0 | 0 | 213 | 215 | 6 |
| 16 | 0 | 0 | 62 | 62 | 15 |
| 18 | 0 | 0 | 0 | 5 | 1 |
| 20 | 0 | 0 | 27 | 30 | 26 |
| 1 | 1 | 0 | 1218 | 1167 | 63 |
| 3 | 1 | 0 | 1655 | 1656 | 94 |
| 5 | 1 | 0 | 989 | 1026 | 55 |
| 9 | 1 | 0 | 210 | 231 | 11 |
| 11 | 1 | 0 | 138 | 136 | 11 |
| 13 | 1 | 0 | 35 | 36 | 29 |
| 15 | 1 | 0 | 219 | 216 | 11 |
| 17 | 1 | 0 | 126 | 140 | 10 |
| 19 | 1 | 0 | 39 | 51 | 32 |
| 21 | 1 | 0 | 53 | 41 | 16 |
| 2 | 2 | 0 | 224 | 209 | 11 |
| 4 | 2 | 0 | 758 | 755 | 41 |
| 6 | 2 | 0 | 550 | 532 | 26 |
| 8 | 2 | 0 | 204 | 180 | 12 |
| 10 | 2 | 0 | 242 | 328 | 14 |
| 12 | 2 | 0 | 183 | 176 | 13 |
| 14 | 2 | 0 | 91 | 84 | 12 |
| 16 | 2 | 0 | 89 | 99 | 12 |
| 18 | 2 | 0 | 44 | 47 | 25 |
| −6 | 2 | 2 | 749 | 742 | 35 |
| −4 | 2 | 2 | 169 | 161 | 9 |
| −2 | 2 | 2 | 211 | 214 | 9 |
| 0 | 2 | 2 | 489 | 463 | 25 |
| 2 | 2 | 2 | 576 | 530 | 25 |
| 4 | 2 | 2 | 467 | 442 | 24 |
| 6 | 2 | 2 | 234 | 218 | 13 |
| 8 | 2 | 2 | 170 | 152 | 13 |
| 10 | 2 | 2 | 142 | 130 | 7 |
| 12 | 2 | 2 | 209 | 212 | 13 |
| 14 | 2 | 2 | 104 | 96 | 10 |
| 16 | 2 | 2 | 100 | 107 | 10 |
| 20 | 2 | 2 | 49 | 49 | 15 |
| −21 | 3 | 2 | 18 | 33 | 18 |
| −19 | 3 | 2 | 178 | 160 | 12 |
| −17 | 3 | 2 | 65 | 59 | 17 |
| −15 | 3 | 2 | 153 | 162 | 10 |
| −13 | 3 | 2 | 101 | 125 | 12 |

TABLE 8-continued

Observed and calculated structure factors for 24F2-DM.

| h | k | l | 10Fc | 10Fc | 10s |
|---|---|---|------|------|-----|
| 9 | 3 | 2 | 189 | 167 | 11 |
| 11 | 3 | 2 | 93 | 78 | 11 |
| 13 | 3 | 2 | 0 | 30 | 1 |
| 15 | 3 | 2 | 41 | 64 | 35 |
| 19 | 3 | 2 | 43 | 35 | 20 |
| 16 | 4 | 2 | 41 | 37 | 26 |
| −3 | −7 | 3 | 41 | 44 | 4 |
| −1 | −7 | 3 | 20 | 15 | 20 |
| −12 | −6 | 3 | 44 | 44 | 6 |
| −10 | −6 | 3 | 34 | 29 | 9 |
| −8 | −6 | 3 | 30 | 19 | 11 |
| −6 | −6 | 3 | 57 | 59 | 5 |
| −4 | −6 | 3 | 84 | 79 | 4 |
| −2 | −6 | 3 | 80 | 81 | 4 |
| 0 | −6 | 3 | 70 | 69 | 4 |
| 2 | −6 | 3 | 19 | 13 | 18 |
| 4 | −6 | 3 | 25 | 28 | 24 |
| 6 | −6 | 3 | 0 | 18 | 1 |
| 8 | −6 | 3 | 0 | 15 | 1 |
| −17 | −5 | 3 | 28 | 24 | 10 |
| −15 | −5 | 3 | 39 | 35 | 9 |
| −13 | −5 | 3 | 50 | 64 | 7 |
| −11 | −5 | 3 | 66 | 72 | 20 |
| −9 | −5 | 3 | 87 | 82 | 7 |
| −7 | −5 | 3 | 288 | 270 | 8 |
| −5 | −5 | 3 | 155 | 129 | 9 |
| −3 | −5 | 3 | 106 | 88 | 7 |
| −1 | −5 | 3 | 156 | 154 | 5 |
| 1 | −5 | 3 | 153 | 160 | 6 |
| 3 | −5 | 3 | 162 | 160 | 6 |
| 5 | −5 | 3 | 75 | 69 | 10 |
| 7 | −5 | 3 | 78 | 93 | 10 |
| 9 | −5 | 3 | 1 | 48 | 1 |
| 11 | −5 | 3 | 27 | 8 | 27 |
| 13 | −5 | 3 | 22 | 9 | 22 |
| −20 | −4 | 3 | 35 | 23 | 10 |
| −18 | −4 | 3 | 0 | 24 | 1 |
| −16 | −4 | 3 | 59 | 75 | 13 |
| −14 | −4 | 3 | 103 | 134 | 12 |
| −12 | −4 | 3 | 33 | 32 | 14 |
| −10 | −4 | 3 | 83 | 82 | 5 |
| −8 | −4 | 3 | 140 | 136 | 4 |
| −6 | −4 | 3 | 104 | 102 | 3 |
| −4 | −4 | 3 | 470 | 447 | 9 |
| −2 | −4 | 3 | 140 | 128 | 3 |
| 0 | −4 | 3 | 329 | 319 | 8 |
| 2 | −4 | 3 | 83 | 78 | 4 |
| 4 | −4 | 3 | 209 | 203 | 6 |
| 6 | −4 | 3 | 209 | 203 | 9 |
| 8 | −4 | 3 | 139 | 143 | 9 |
| 10 | −4 | 3 | 111 | 120 | 10 |
| 12 | −4 | 3 | 0 | 46 | 1 |
| 14 | −4 | 3 | 28 | 21 | 27 |
| 16 | −4 | 3 | 27 | 40 | 27 |
| −21 | −3 | 3 | 53 | 52 | 8 |
| −19 | −3 | 3 | 66 | 60 | 7 |
| −17 | −3 | 3 | 54 | 12 | 16 |
| −15 | −3 | 3 | 95 | 92 | 5 |
| −13 | −3 | 3 | 51 | 62 | 7 |
| −11 | −3 | 3 | 73 | 77 | 6 |
| −9 | −3 | 3 | 3 | 329 | 7 |
| −7 | −3 | 3 | 191 | 185 | 11 |
| −5 | −3 | 3 | 213 | 213 | 12 |
| −3 | −3 | 3 | 169 | 199 | 10 |
| −1 | −3 | 3 | 309 | 290 | 16 |
| 1 | −3 | 3 | 155 | 167 | 11 |
| 3 | −3 | 3 | 258 | 237 | 15 |
| 5 | −3 | 3 | 406 | 389 | 14 |
| 7 | −3 | 3 | 264 | 260 | 7 |
| −7 | −3 | 5 | 281 | 266 | 10 |
| −5 | −3 | 5 | 242 | 228 | 13 |
| −3 | −3 | 5 | 289 | 263 | 10 |
| −1 | −3 | 5 | 229 | 180 | 13 |
| 1 | −3 | 5 | 131 | 106 | 12 |
| 3 | −3 | 5 | 268 | 265 | 10 |
| 5 | −3 | 5 | 218 | 195 | 8 |
| 7 | −3 | 5 | 119 | 121 | 9 |
| 9 | −3 | 5 | 98 | 80 | 10 |
| 11 | −3 | 5 | 92 | 91 | 5 |
| 13 | −3 | 5 | 47 | 28 | 8 |
| −24 | −2 | 5 | 60 | 50 | 8 |
| −22 | −2 | 5 | 51 | 61 | 10 |
| −20 | −2 | 5 | 150 | 133 | 5 |
| −18 | −2 | 5 | 355 | 342 | 9 |
| −16 | −2 | 5 | 268 | 264 | 7 |
| −14 | −2 | 5 | 386 | 397 | 8 |
| −12 | −2 | 5 | 117 | 119 | 5 |
| −10 | −2 | 5 | 72 | 33 | 11 |
| −8 | −2 | 5 | 252 | 257 | 14 |
| −6 | −2 | 5 | 352 | 405 | 18 |
| −4 | −2 | 5 | 451 | 472 | 25 |
| −2 | −2 | 5 | 447 | 420 | 22 |
| 0 | −2 | 5 | 309 | 277 | 16 |
| 2 | −2 | 5 | 514 | 461 | 25 |
| 4 | −2 | 5 | 377 | 363 | 20 |
| 6 | −2 | 5 | 177 | 197 | 8 |
| 8 | −2 | 5 | 0 | 31 | 1 |
| 10 | −2 | 5 | 164 | 167 | 8 |
| 12 | −2 | 5 | 36 | 53 | 12 |
| 14 | −2 | 5 | 66 | 77 | 7 |
| 16 | −2 | 5 | 87 | 90 | 6 |
| 18 | −2 | 5 | 61 | 78 | 5 |
| −23 | −1 | 5 | 140 | 113 | 10 |
| −21 | −1 | 5 | 89 | 84 | 10 |
| −19 | −1 | 5 | 102 | 99 | 10 |
| −17 | −1 | 5 | 82 | 97 | 8 |
| −15 | −1 | 5 | 188 | 189 | 6 |
| −13 | −1 | 5 | 195 | 180 | 12 |
| −11 | −1 | 5 | 390 | 359 | 20 |
| −9 | −1 | 5 | 693 | 706 | 37 |
| −7 | −1 | 5 | 126 | 122 | 9 |
| −5 | −1 | 5 | 135 | 140 | 9 |
| −3 | −1 | 5 | 180 | 183 | 7 |
| −1 | −1 | 5 | 968 | 916 | 28 |
| 1 | −1 | 5 | 688 | 665 | 24 |
| 3 | −1 | 5 | 648 | 628 | 23 |
| 5 | −1 | 5 | 148 | 155 | 9 |
| 7 | −1 | 5 | 370 | 391 | 12 |
| 9 | −1 | 5 | 198 | 199 | 7 |
| 11 | −1 | 5 | 108 | 121 | 6 |
| 13 | −1 | 5 | 119 | 109 | 7 |
| 15 | −1 | 5 | 84 | 99 | 7 |
| 17 | −1 | 5 | 70 | 72 | 8 |
| 19 | −1 | 5 | 92 | 80 | 6 |
| −24 | 0 | 5 | 170 | 140 | 11 |
| −22 | 0 | 5 | 0 | 2 | 1 |
| −20 | 0 | 5 | 217 | 238 | 12 |
| −18 | 0 | 5 | 47 | 62 | 33 |
| −16 | 0 | 5 | 157 | 161 | 8 |
| −14 | 0 | 5 | 369 | 353 | 13 |
| −12 | 0 | 5 | 321 | 281 | 17 |
| −10 | 0 | 5 | 723 | 638 | 37 |
| −8 | 0 | 5 | 812 | 757 | 42 |
| −6 | 0 | 5 | 1403 | 1332 | 50 |
| −4 | 0 | 5 | 72 | 72 | 5 |
| −2 | 0 | 5 | 388 | 436 | 16 |
| 0 | 0 | 5 | 253 | 285 | 13 |
| 2 | 0 | 5 | 164 | 180 | 13 |
| 4 | 0 | 5 | 186 | 200 | 10 |
| 6 | 0 | 5 | 310 | 343 | 16 |
| 8 | 0 | 5 | 211 | 238 | 8 |
| 10 | 0 | 5 | 128 | 116 | 4 |
| 12 | 0 | 5 | 260 | 264 | 11 |
| 14 | 0 | 5 | 207 | 181 | 10 |
| 16 | 0 | 5 | 27 | 1 | 26 |
| 18 | 0 | 5 | 0 | 10 | 1 |
| −25 | 1 | 5 | 39 | 39 | 23 |
| −23 | 1 | 5 | 109 | 113 | 11 |
| −21 | 1 | 5 | 68 | 83 | 13 |
| −19 | 1 | 5 | 106 | 98 | 11 |
| −17 | 1 | 5 | 105 | 96 | 9 |
| −15 | 1 | 5 | 181 | 190 | 9 |

TABLE 8-continued

Observed and calculated structure factors for 24F2-DM.

| h | k | l | 10Fo | 10Fc | 10s |
|---|---|---|------|------|-----|
| −13 | 1 | 5 | 192 | 181 | 13 |
| −11 | 1 | 5 | 374 | 359 | 20 |
| −9 | 1 | 5 | 721 | 706 | 35 |
| −7 | 1 | 5 | 133 | 119 | 7 |
| 5 | 1 | 7 | 494 | 492 | 16 |
| 7 | 1 | 7 | 283 | 274 | 10 |
| 9 | 1 | 7 | 145 | 141 | 9 |
| 11 | 1 | 7 | 297 | 270 | 13 |
| 13 | 1 | 7 | 17 | 22 | 16 |
| 15 | 1 | 7 | 33 | 51 | 16 |
| −24 | 2 | 7 | 33 | 33 | 33 |
| −22 | 2 | 7 | 35 | 47 | 34 |
| −20 | 2 | 7 | 149 | 127 | 10 |
| −18 | 2 | 7 | 59 | 57 | 19 |
| −16 | 2 | 7 | 197 | 181 | 11 |
| −4 | 2 | 7 | 281 | 252 | 13 |
| −2 | 2 | 7 | 211 | 191 | 12 |
| 0 | 2 | 7 | 182 | 158 | 11 |
| 2 | 2 | 7 | 367 | 352 | 19 |
| 4 | 2 | 7 | 79 | 83 | 8 |
| 6 | 2 | 7 | 192 | 206 | 9 |
| 8 | 2 | 7 | 0 | 15 | 1 |
| 10 | 2 | 7 | 179 | 210 | 11 |
| 12 | 2 | 7 | 68 | 73 | 11 |
| 14 | 2 | 7 | 137 | 118 | 7 |
| 16 | 2 | 7 | 54 | 58 | 7 |
| −23 | 3 | 7 | 49 | 44 | 19 |
| −21 | 3 | 7 | 165 | 150 | 11 |
| 1 | 3 | 7 | 154 | 166 | 12 |
| 3 | 3 | 7 | 225 | 233 | 12 |
| 5 | 3 | 7 | 139 | 133 | 10 |
| 7 | 3 | 7 | 235 | 227 | 13 |
| 9 | 3 | 7 | 59 | 58 | 11 |
| 11 | 3 | 7 | 23 | 35 | 23 |
| 13 | 3 | 7 | 77 | 75 | 8 |
| 15 | 3 | 7 | 27 | 25 | 27 |
| 4 | 4 | 7 | 172 | 188 | 11 |
| 6 | 4 | 7 | 104 | 95 | 10 |
| 8 | 4 | 7 | 101 | 100 | 9 |
| 10 | 4 | 7 | 67 | 67 | 13 |
| 12 | 4 | 7 | 27 | 4 | 27 |
| −14 | −6 | 8 | 0 | 16 | 1 |
| −12 | −6 | 8 | 0 | 31 | 1 |
| −10 | −6 | 8 | 0 | 4 | 1 |
| −8 | −6 | 8 | 43 | 42 | 18 |
| −6 | −6 | 8 | 97 | 96 | 5 |
| −4 | −6 | 8 | 70 | 70 | 8 |
| −2 | −6 | 8 | 57 | 50 | 10 |
| 0 | −6 | 8 | 15 | 29 | 14 |
| 2 | −6 | 8 | 42 | 42 | 14 |
| −19 | −5 | 8 | 57 | 50 | 7 |
| −17 | −5 | 8 | 0 | 31 | 1 |
| −15 | −5 | 8 | 40 | 37 | 19 |
| −13 | −5 | 8 | 6 | 19 | 6 |
| −11 | −5 | 8 | 153 | 144 | 13 |
| −9 | −5 | 8 | 116 | 120 | 4 |
| −7 | −5 | 8 | 185 | 198 | 9 |
| −5 | −5 | 8 | 90 | 88 | 5 |
| −3 | −5 | 8 | 140 | 159 | 10 |
| −1 | −5 | 8 | 29 | 32 | 29 |
| 1 | −5 | 8 | 72 | 77 | 9 |
| 3 | −5 | 8 | 42 | 43 | 16 |
| 5 | −5 | 8 | 33 | 33 | 32 |
| 7 | −5 | 8 | 32 | 38 | 32 |
| 9 | −5 | 8 | 34 | 24 | 21 |
| −22 | −4 | 8 | 29 | 25 | 16 |
| −20 | −4 | 8 | 59 | 66 | 8 |
| −18 | −4 | 8 | 38 | 50 | 13 |
| −16 | −4 | 8 | 85 | 94 | 6 |
| −14 | −4 | 8 | 152 | 140 | 6 |
| −12 | −4 | 8 | 161 | 151 | 4 |
| −10 | −4 | 8 | 133 | 133 | 4 |
| −8 | −4 | 8 | 0 | 31 | 1 |
| −6 | −4 | 8 | 84 | 69 | 5 |
| −4 | −4 | 8 | 95 | 89 | 5 |
| −2 | −4 | 8 | 80 | 62 | 5 |
| 0 | −4 | 8 | 163 | 143 | 12 |
| 2 | −4 | 8 | 111 | 110 | 9 |
| 4 | −4 | 8 | 165 | 161 | 11 |
| 6 | −4 | 8 | 87 | 108 | 10 |
| 8 | −4 | 8 | 45 | 39 | 21 |
| 10 | −4 | 8 | 65 | 65 | 12 |
| −23 | −3 | 8 | 29 | 19 | 18 |
| −21 | −3 | 8 | 77 | 85 | 6 |
| −19 | −3 | 8 | 64 | 55 | 6 |
| −17 | −3 | 8 | 272 | 264 | 7 |
| −15 | −3 | 8 | 274 | 246 | 6 |
| −13 | −3 | 8 | 390 | 386 | 10 |
| −11 | −3 | 8 | 144 | 145 | 5 |
| −9 | −3 | 8 | 225 | 220 | 5 |
| −7 | −3 | 8 | 178 | 180 | 5 |
| −25 | −1 | 10 | 0 | 26 | 1 |
| −23 | −1 | 10 | 113 | 107 | 16 |
| −21 | −1 | 10 | 79 | 77 | 8 |
| −19 | −1 | 10 | 150 | 163 | 7 |
| −17 | −1 | 10 | 94 | 100 | 5 |
| −15 | −1 | 10 | 278 | 271 | 7 |
| −13 | −1 | 10 | 405 | 423 | 9 |
| −11 | −1 | 10 | 284 | 298 | 16 |
| −9 | −1 | 10 | 282 | 278 | 16 |
| −3 | −1 | 10 | 238 | 249 | 15 |
| −1 | −1 | 10 | 112 | 94 | 4 |
| 1 | −1 | 10 | 318 | 308 | 8 |
| 3 | −1 | 10 | 239 | 236 | 10 |
| 5 | −1 | 10 | 49 | 60 | 9 |
| 7 | −1 | 10 | 217 | 242 | 9 |
| 9 | −1 | 10 | 55 | 71 | 8 |
| 11 | −1 | 10 | 93 | 103 | 7 |
| 13 | −1 | 10 | 30 | 29 | 15 |
| −26 | 0 | 10 | 54 | 28 | 15 |
| −24 | 0 | 10 | 39 | 29 | 26 |
| −22 | 0 | 10 | 134 | 156 | 9 |
| −20 | 0 | 10 | 151 | 132 | 10 |
| −18 | 0 | 10 | 73 | 74 | 14 |
| −16 | 0 | 10 | 33 | 46 | 31 |
| −14 | 0 | 10 | 45 | 66 | 11 |
| −8 | 0 | 10 | 672 | 620 | 35 |
| −6 | 0 | 10 | 391 | 499 | 20 |
| −4 | 0 | 10 | 147 | 167 | 10 |
| −2 | 0 | 10 | 459 | 449 | 24 |
| 0 | 0 | 10 | 226 | 214 | 8 |
| 2 | 0 | 10 | 220 | 244 | 5 |
| 4 | 0 | 10 | 94 | 87 | 4 |
| 6 | 0 | 10 | 140 | 133 | 5 |
| 8 | 0 | 10 | 55 | 64 | 7 |
| 10 | 0 | 10 | 88 | 81 | 8 |
| 12 | 0 | 10 | 86 | 83 | 7 |
| 14 | 0 | 10 | 32 | 28 | 14 |
| −27 | 1 | 10 | 32 | 28 | 31 |
| −25 | 1 | 10 | 0 | 27 | 1 |
| −23 | 1 | 10 | 114 | 107 | 10 |
| −21 | 1 | 10 | 77 | 77 | 14 |
| −19 | 1 | 10 | 176 | 163 | 11 |
| −17 | 1 | 10 | 105 | 101 | 10 |
| −15 | 1 | 10 | 249 | 270 | 15 |
| −11 | 1 | 10 | 287 | 299 | 16 |
| −9 | 1 | 10 | 297 | 278 | 15 |
| −7 | 1 | 10 | 220 | 210 | 13 |
| −5 | 1 | 10 | 332 | 301 | 18 |
| −3 | 1 | 10 | 277 | 250 | 13 |
| −1 | 1 | 10 | 109 | 94 | 5 |
| 1 | 1 | 10 | 305 | 308 | 9 |
| 3 | 1 | 10 | 237 | 236 | 8 |
| 5 | 1 | 10 | 51 | 58 | 11 |
| 7 | 1 | 10 | 201 | 242 | 12 |
| 9 | 1 | 10 | 81 | 71 | 8 |
| 11 | 1 | 10 | 119 | 103 | 5 |
| −26 | 2 | 10 | 91 | 68 | 9 |
| −24 | 2 | 10 | 63 | 56 | 15 |
| −22 | 2 | 10 | 30 | 45 | 30 |
| −6 | 2 | 10 | 281 | 250 | 14 |
| −4 | 2 | 10 | 152 | 144 | 8 |

TABLE 8-continued

Observed and calculated structure factors for 24F2-DM.

| h | k | l | 10Fo | 10Fc | 10s |
|---|---|---|------|------|-----|
| -2 | 2 | 10 | 86 | 81 | 11 |
| 0 | 2 | 10 | 175 | 173 | 6 |
| 2 | 2 | 10 | 156 | 157 | 6 |
| 4 | 2 | 10 | 111 | 110 | 7 |
| 6 | 2 | 10 | 58 | 60 | 9 |
| 8 | 2 | 10 | 42 | 34 | 12 |
| 10 | 2 | 10 | 114 | 105 | 17 |
| 12 | 2 | 10 | 0 | 25 | 1 |
| -5 | 3 | 10 | 147 | 173 | 13 |
| -3 | 3 | 10 | 158 | 163 | 12 |
| -1 | 3 | 10 | 110 | 95 | 8 |
| 1 | 3 | 10 | 257 | 237 | 13 |
| 3 | 3 | 10 | 371 | 377 | 12 |
| 5 | 3 | 10 | 96 | 100 | 7 |
| 7 | 3 | 10 | 252 | 263 | 11 |
| 9 | 3 | 10 | 103 | 93 | 12 |
| 11 | 3 | 10 | 121 | 88 | 13 |
| 0 | 4 | 10 | 143 | 141 | 10 |
| 2 | 4 | 10 | 184 | 173 | 10 |
| 4 | 4 | 10 | 33 | 45 | 33 |
| 6 | 4 | 10 | 44 | 43 | 20 |
| 8 | 4 | 10 | 85 | 78 | 6 |
| -10 | -6 | 11 | 85 | 75 | 5 |
| -6 | -6 | 11 | 59 | 67 | 9 |
| -4 | -6 | 11 | 76 | 73 | 8 |
| -17 | -6 | 11 | 0 | 20 | 1 |
| -11 | -1 | 13 | 141 | 156 | 4 |
| -9 | -1 | 13 | 291 | 293 | 7 |
| -7 | -1 | 13 | 140 | 129 | 5 |
| -5 | -1 | 13 | 118 | 114 | 4 |
| -3 | -1 | 13 | 114 | 109 | 5 |
| -1 | -1 | 13 | 162 | 161 | 6 |
| 1 | -1 | 13 | 126 | 122 | 7 |
| 3 | -1 | 13 | 113 | 122 | 6 |
| 5 | -1 | 13 | 74 | 89 | 7 |
| 7 | -1 | 13 | 132 | 136 | 7 |
| 9 | -1 | 13 | 0 | 25 | 1 |
| -26 | 0 | 13 | 111 | 100 | 10 |
| -24 | 0 | 13 | 104 | 88 | 7 |
| -22 | 0 | 13 | 78 | 67 | 8 |
| -20 | 0 | 13 | 70 | 76 | 10 |
| -18 | 0 | 13 | 5 | 7 | 5 |
| -16 | 0 | 13 | 29 | 40 | 29 |
| -14 | 0 | 13 | 342 | 363 | 14 |
| -12 | 0 | 13 | 431 | 434 | 14 |
| -10 | 0 | 13 | 362 | 375 | 13 |
| -8 | 0 | 13 | 158 | 155 | 6 |
| -6 | 0 | 13 | 296 | 272 | 7 |
| -4 | 0 | 13 | 47 | 48 | 7 |
| -2 | 0 | 13 | 461 | 431 | 12 |
| 0 | 0 | 13 | 91 | 82 | 7 |
| 2 | 0 | 13 | 17 | 26 | 17 |
| 4 | 0 | 13 | 57 | 50 | 7 |
| 6 | 0 | 13 | 34 | 7 | 17 |
| 8 | 0 | 13 | 170 | 144 | 8 |
| 10 | 0 | 13 | 57 | 43 | 7 |
| -25 | 1 | 13 | 83 | 82 | 11 |
| -23 | 1 | 13 | 100 | 89 | 10 |
| -21 | 1 | 13 | 83 | 90 | 11 |
| -19 | 1 | 13 | 124 | 124 | 9 |
| -17 | 1 | 13 | 242 | 247 | 14 |
| -15 | 1 | 13 | 169 | 189 | 13 |
| -13 | 1 | 13 | 41 | 39 | 30 |
| -11 | 1 | 13 | 142 | 156 | 14 |
| -9 | 1 | 13 | 291 | 292 | 10 |
| -7 | 1 | 13 | 141 | 129 | 7 |
| -5 | 1 | 13 | 117 | 115 | 5 |
| -3 | 1 | 13 | 97 | 107 | 7 |
| -1 | 1 | 13 | 171 | 163 | 7 |
| 1 | 1 | 13 | 129 | 123 | 14 |
| 3 | 1 | 13 | 116 | 121 | 8 |
| 5 | 1 | 13 | 91 | 89 | 11 |
| 7 | 1 | 13 | 149 | 136 | 8 |
| -14 | 2 | 13 | 66 | 87 | 15 |
| -12 | 2 | 13 | 286 | 283 | 16 |
| -10 | 2 | 13 | 138 | 141 | 10 |
| -8 | 2 | 13 | 113 | 123 | 9 |
| -6 | 2 | 13 | 242 | 232 | 11 |
| -4 | 2 | 13 | 112 | 122 | 6 |
| -2 | 2 | 13 | 195 | 186 | 8 |
| 0 | 2 | 13 | 104 | 85 | 6 |
| 2 | 2 | 13 | 48 | 54 | 10 |
| 4 | 2 | 13 | 43 | 46 | 11 |
| 6 | 2 | 13 | 155 | 146 | 13 |
| 8 | 2 | 13 | 61 | 54 | 6 |
| -9 | 3 | 13 | 75 | 80 | 12 |
| -7 | 3 | 13 | 291 | 279 | 15 |
| -5 | 3 | 13 | 153 | 159 | 11 |
| -1 | 3 | 13 | 110 | 103 | 6 |
| 1 | 3 | 13 | 90 | 81 | 6 |
| 3 | 3 | 13 | 0 | 25 | 1 |
| 5 | 3 | 13 | 87 | 80 | 6 |
| 7 | 3 | 13 | 43 | 42 | 12 |
| -4 | 4 | 13 | 51 | 41 | 17 |
| -2 | 4 | 13 | 34 | 54 | 33 |
| 0 | 4 | 13 | 95 | 85 | 8 |
| 2 | 4 | 13 | 71 | 70 | 10 |
| 4 | 4 | 13 | 35 | 3 | 35 |
| -15 | -5 | 14 | 150 | 136 | 6 |
| -13 | -5 | 14 | 170 | 139 | 6 |
| -11 | -5 | 14 | 143 | 124 | 7 |
| -9 | -5 | 14 | 30 | 36 | 29 |
| -7 | -5 | 14 | 58 | 64 | 13 |
| -5 | -5 | 14 | 63 | 57 | 11 |
| -1 | -5 | 14 | 3 | 24 | 3 |
| -20 | -4 | 14 | 36 | 16 | 22 |
| -18 | -4 | 14 | 74 | 76 | 6 |
| -16 | -4 | 14 | 156 | 143 | 7 |
| -14 | -4 | 14 | 76 | 99 | 11 |
| -12 | -4 | 14 | 200 | 198 | 19 |
| -10 | -4 | 14 | 23 | 20 | 22 |
| -8 | -4 | 14 | 125 | 138 | 5 |
| -6 | -4 | 14 | 104 | 104 | 5 |
| -13 | -3 | 17 | 88 | 77 | 7 |
| -11 | -3 | 17 | 93 | 92 | 6 |
| -9 | -3 | 17 | 93 | 97 | 6 |
| -7 | -3 | 17 | 45 | 62 | 8 |
| -5 | -3 | 17 | 107 | 101 | 6 |
| -24 | -2 | 17 | 23 | 20 | 22 |
| -22 | -2 | 17 | 15 | 23 | 14 |
| -20 | -2 | 17 | 92 | 92 | 5 |
| -18 | -2 | 17 | 179 | 186 | 8 |
| -16 | -2 | 17 | 96 | 93 | 5 |
| -14 | -2 | 17 | 126 | 115 | 6 |
| -12 | -2 | 17 | 88 | 88 | 8 |
| -10 | -2 | 17 | 153 | 154 | 8 |
| -8 | -2 | 17 | 214 | 217 | 9 |
| -6 | -2 | 17 | 97 | 101 | 6 |
| -4 | -2 | 17 | 81 | 86 | 6 |
| -2 | -2 | 17 | 18 | 29 | 17 |
| 0 | -2 | 17 | 19 | 25 | 19 |
| -25 | 1 | 17 | 31 | 49 | 16 |
| -23 | 1 | 17 | 47 | 43 | 10 |
| -21 | 1 | 17 | 127 | 137 | 5 |
| -19 | 1 | 17 | 67 | 81 | 6 |
| -17 | 1 | 17 | 112 | 136 | 5 |
| -15 | 1 | 17 | 25 | 25 | 24 |
| -13 | 1 | 17 | 43 | 42 | 12 |
| -11 | 1 | 17 | 187 | 169 | 9 |
| -9 | 1 | 17 | 190 | 169 | 5 |
| -5 | 1 | 17 | 49 | 34 | 10 |
| -3 | 1 | 17 | 28 | 37 | 27 |
| -1 | 1 | 17 | 65 | 61 | 8 |
| 1 | 1 | 17 | 48 | 44 | 10 |
| 3 | 1 | 17 | 91 | 80 | 6 |
| -24 | 0 | 17 | 78 | 67 | 7 |
| -22 | 0 | 17 | 28 | 1 | 28 |
| -20 | 0 | 17 | 55 | 57 | 10 |
| -18 | 0 | 17 | 30 | 19 | 29 |
| -16 | 0 | 17 | 236 | 284 | 12 |
| -14 | 0 | 17 | 210 | 197 | 11 |
| -12 | 0 | 17 | 517 | 573 | 17 |

TABLE 8-continued

Observed and calculated structure factors for 24F2-DM.

| h | k | l | 10Fo | 10Fc | 10s |
|---|---|---|---|---|---|
| −10 | 0 | 17 | 109 | 126 | 6 |
| −8 | 0 | 17 | 137 | 154 | 11 |
| −6 | 0 | 17 | 47 | 49 | 9 |
| −4 | 0 | 17 | 0 | 18 | 1 |
| −2 | 0 | 17 | 108 | 109 | 5 |
| 0 | 0 | 17 | 14 | 1 | 13 |
| 2 | 0 | 17 | 12 | 20 | 12 |
| 4 | 0 | 17 | 60 | 58 | 7 |
| −25 | 1 | 17 | 53 | 49 | 13 |
| −23 | 1 | 17 | 52 | 42 | 17 |
| −21 | 1 | 17 | 125 | 136 | 9 |
| −19 | 1 | 17 | 68 | 82 | 12 |
| −17 | 1 | 17 | 121 | 136 | 6 |
| −15 | 1 | 17 | 32 | 26 | 31 |
| −13 | 1 | 17 | 31 | 41 | 30 |
| −11 | 1 | 17 | 182 | 169 | 12 |
| −9 | 1 | 17 | 159 | 169 | 14 |
| −7 | 1 | 17 | 111 | 130 | 6 |
| −5 | 1 | 17 | 32 | 33 | 24 |
| −3 | 1 | 17 | 18 | 36 | 17 |
| −1 | 1 | 17 | 65 | 62 | 8 |
| 1 | 1 | 17 | 33 | 43 | 32 |
| −20 | 2 | 17 | 75 | 93 | 12 |
| −18 | 2 | 17 | 190 | 186 | 10 |
| −16 | 2 | 17 | 91 | 92 | 12 |
| −14 | 2 | 17 | 103 | 113 | 11 |
| −12 | 2 | 17 | 80 | 89 | 9 |
| −10 | 2 | 17 | 144 | 155 | 23 |
| −8 | 2 | 17 | 199 | 217 | 16 |
| 20 | 2 | 0 | 121 | 101 | 9 |
|  | 3 | 0 | 194 | 176 | 15 |
| 13 | 3 | 0 | 82 | 87 | 13 |
| 15 | 3 | 0 | 68 | 61 | 17 |
| 17 | 3 | 0 | 80 | 92 | 14 |
| −3 | −7 | 1 | 69 | 70 | 3 |
| −1 | −7 | 1 | 13 | 28 | 13 |
| 1 | −7 | 1 | 55 | 50 | 3 |
| −8 | −6 | 1 | 48 | 49 | 5 |
| −6 | −6 | 1 | 57 | 66 | 15 |
| −4 | −6 | 1 | 24 | 25 | 14 |
| −2 | −6 | 1 | 57 | 53 | 5 |
| 0 | −6 | 1 | 103 | 101 | 4 |
| 2 | −6 | 1 | 110 | 132 | 6 |
| 4 | −6 | 1 | 205 | 208 | 6 |
| 8 | −6 | 1 | 86 | 92 | 8 |
| 10 | −6 | 1 | 84 | 81 | 8 |
| −17 | −5 | 1 | 50 | 52 | 14 |
| −15 | −5 | 1 | 72 | 47 | 11 |
| −13 | −5 | 1 | 43 | 42 | 12 |
| −11 | −5 | 1 | 11 | 31 | 10 |
| −9 | −5 | 1 | 90 | 122 | 5 |
| −7 | −5 | 1 | 84 | 95 | 6 |
| −5 | −5 | 1 | 92 | 112 | 6 |
| −3 | −5 | 1 | 343 | 329 | 10 |
| −1 | −5 | 1 | 28 | 31 | 16 |
| 1 | −5 | 1 | 160 | 164 | 6 |
| 3 | −5 | 1 | 96 | 93 | 5 |
| 5 | −5 | 1 | 163 | 168 | 20 |
| 7 | −5 | 1 | 37 | 30 | 7 |
| 9 | −5 | 1 | 25 | 29 | 25 |
| 11 | −5 | 1 | 10 | 27 | 10 |
| 13 | −5 | 1 | 41 | 41 | 24 |
| 15 | −5 | 1 | 16 | 28 | 16 |
| −18 | −4 | 1 | 50 | 46 | 6 |
| −16 | −4 | 1 | 75 | 86 | 14 |
| −14 | −4 | 1 | 61 | 67 | 9 |
| −12 | −4 | 1 | 46 | 50 | 15 |
| −10 | −4 | 1 | 137 | 129 | 6 |
| −8 | −4 | 1 | 50 | 46 | 8 |
| −6 | −4 | 1 | 138 | 131 | 4 |
| −4 | −4 | 1 | 137 | 125 | 3 |
| −2 | −4 | 1 | 221 | 211 | 4 |
| 0 | −4 | 1 | 210 | 196 | 5 |
| 2 | −4 | 1 | 155 | 132 | 5 |
| 4 | −4 | 1 | 101 | 91 | 6 |
| 6 | −4 | 1 | 250 | 247 | 7 |

TABLE 8-continued

Observed and calculated structure factors for 24F2-DM.

| h | k | l | 10Fo | 10Fc | 10s |
|---|---|---|---|---|---|
| 8 | −4 | 1 | 150 | 142 | 5 |
| 10 | −4 | 1 | 34 | 51 | 33 |
| 12 | −4 | 1 | 144 | 163 | 5 |
| 14 | −4 | 1 | 67 | 64 | 5 |
| 16 | −4 | 1 | 66 | 74 | 14 |
| 18 | −4 | 1 | 33 | 19 | 33 |
| −21 | −3 | 1 | 33 | 22 | 12 |
| −19 | −3 | 1 | 78 | 81 | 7 |
| −17 | −3 | 1 | 59 | 63 | 9 |
| −15 | −3 | 1 | 31 | 42 | 27 |
| −13 | −3 | 1 | 49 | 35 | 23 |
| −11 | −3 | 1 | 106 | 101 | 4 |
| −9 | −3 | 1 | 108 | 108 | 4 |
| −7 | −3 | 1 | 499 | 448 | 25 |
| −5 | −3 | 1 | 752 | 678 | 38 |
| −3 | −3 | 1 | 301 | 295 | 18 |
| −1 | −3 | 1 | 424 | 447 | 16 |
| 1 | −3 | 1 | 457 | 428 | 30 |
| 3 | −3 | 1 | 394 | 438 | 21 |
| 7 | −3 | 1 | 116 | 98 | 6 |
| 9 | −3 | 1 | 271 | 270 | 7 |
| 11 | −3 | 1 | 72 | 54 | 5 |
| 13 | −3 | 1 | 112 | 129 | 18 |
| 15 | −3 | 1 | 150 | 157 | 22 |
| 17 | −3 | 1 | 70 | 71 | 15 |
| 19 | −3 | 1 | 47 | 56 | 7 |
| −22 | −2 | 1 | 50 | 71 | 7 |
| −20 | −2 | 1 | 127 | 106 | 7 |
| −18 | −2 | 1 | 36 | 43 | 18 |
| −16 | −2 | 1 | 141 | 132 | 6 |
| −14 | −2 | 1 | 77 | 83 | 8 |
| −12 | −2 | 1 | 134 | 135 | 5 |
| −10 | −2 | 1 | 263 | 250 | 12 |
| −8 | −2 | 1 | 258 | 209 | 13 |
| −6 | −2 | 1 | 351 | 372 | 19 |
| −4 | −2 | 1 | 287 | 302 | 12 |
| −2 | −2 | 1 | 361 | 353 | 19 |
| 0 | −2 | 1 | 225 | 229 | 8 |
| 2 | −2 | 1 | 366 | 330 | 19 |
| 8 | −2 | 1 | 343 | 330 | 18 |
| 9 | −3 | 3 | 163 | 160 | 6 |
| 11 | −3 | 3 | 250 | 287 | 8 |
| 13 | −3 | 3 | 218 | 244 | 9 |
| 15 | −3 | 3 | 89 | 93 | 5 |
| 17 | −3 | 3 | 42 | 43 | 8 |
| −22 | −2 | 3 | 72 | 74 | 8 |
| −20 | −2 | 3 | 63 | 42 | 10 |
| −18 | −2 | 3 | 147 | 148 | 7 |
| −16 | −2 | 3 | 76 | 74 | 7 |
| −14 | −2 | 3 | 177 | 174 | 5 |
| −12 | −2 | 3 | 186 | 176 | 6 |
| −10 | −2 | 3 | 222 | 187 | 12 |
| −8 | −2 | 3 | 696 | 768 | 36 |
| −6 | −2 | 3 | 160 | 167 | 9 |
| −4 | −2 | 3 | 368 | 415 | 21 |
| −2 | −2 | 3 | 32 | 31 | 9 |
| 0 | −2 | 3 | 406 | 375 | 21 |
| 2 | −2 | 3 | 497 | 479 | 26 |
| 8 | −2 | 3 | 333 | 350 | 14 |
| 10 | −2 | 3 | 142 | 150 | 6 |
| 12 | −2 | 3 | 131 | 124 | 7 |
| 14 | −2 | 3 | 155 | 168 | 8 |
| 16 | −2 | 3 | 164 | 189 | 8 |
| 18 | −2 | 3 | 92 | 98 | 6 |
| 20 | −2 | 3 | 45 | 43 | 7 |
| −21 | −1 | 3 | 70 | 74 | 17 |
| −19 | −1 | 3 | 221 | 209 | 7 |
| −17 | −1 | 3 | 81 | 81 | 7 |
| −15 | −1 | 3 | 157 | 160 | 6 |
| −13 | −1 | 3 | 474 | 478 | 18 |
| −11 | −1 | 3 | 218 | 255 | 14 |
| −9 | −1 | 3 | 304 | 304 | 16 |
| −7 | −1 | 3 | 151 | 177 | 9 |
| −5 | −1 | 3 | 458 | 481 | 25 |
| −3 | −1 | 3 | 636 | 628 | 30 |
| −1 | −1 | 3 | 1352 | 1275 | 47 |

TABLE 8-continued

Observed and calculated structure factors for 24F2-DM.

| h | k | l | 10Fo | 10Fc | 10s |
|---|---|---|------|------|-----|
| 1 | −1 | 3 | 453 | 427 | 23 |
| 3 | −1 | 3 | 360 | 364 | 18 |
| 5 | −1 | 3 | 146 | 137 | 6 |
| 7 | −1 | 3 | 188 | 192 | 11 |
| 9 | −1 | 3 | 85 | 72 | 10 |
| 11 | −1 | 3 | 217 | 221 | 7 |
| 13 | −1 | 3 | 256 | 254 | 18 |
| 15 | −1 | 3 | 35 | 23 | 24 |
| 17 | −1 | 3 | 127 | 118 | 8 |
| 19 | −1 | 3 | 36 | 36 | 17 |
| −24 | 0 | 3 | 54 | 55 | 11 |
| −22 | 0 | 3 | 277 | 230 | 14 |
| −20 | 0 | 3 | 85 | 92 | 10 |
| −18 | 0 | 3 | 154 | 172 | 10 |
| −16 | 0 | 3 | 24 | 31 | 24 |
| −14 | 0 | 3 | 158 | 162 | 7 |
| −12 | 0 | 3 | 267 | 218 | 15 |
| −10 | 0 | 3 | 161 | 161 | 11 |
| −8 | 0 | 3 | 1323 | 1304 | 68 |
| −6 | 0 | 3 | 715 | 675 | 37 |
| −4 | 0 | 3 | 1082 | 1021 | 39 |
| −2 | 0 | 3 | 413 | 433 | 15 |
| 0 | 0 | 3 | 1456 | 1433 | 86 |
| 2 | 0 | 3 | 685 | 671 | 35 |
| 4 | 0 | 3 | 393 | 493 | 20 |
| 6 | 0 | 3 | 67 | 68 | 8 |
| 8 | 0 | 3 | 91 | 101 | 9 |
| 10 | 0 | 3 | 72 | 70 | 7 |
| 12 | 0 | 3 | 230 | 232 | 6 |
| 14 | 0 | 3 | 208 | 204 | 7 |
| 16 | 0 | 3 | 58 | 45 | 12 |
| 18 | 0 | 3 | 54 | 60 | 12 |
| 20 | 0 | 3 | 39 | 60 | 15 |
| −23 | 1 | 3 | 149 | 126 | 11 |
| −21 | 1 | 3 | 61 | 75 | 13 |
| −19 | 1 | 3 | 194 | 210 | 13 |
| −17 | 1 | 3 | 80 | 60 | 11 |
| −15 | 1 | 3 | 161 | 159 | 7 |
| −13 | 1 | 3 | 463 | 478 | 25 |
| −11 | 1 | 3 | 257 | 257 | 12 |
| −9 | 1 | 3 | 312 | 301 | 16 |
| −5 | 1 | 3 | 482 | 482 | 17 |
| −3 | 1 | 3 | 607 | 628 | 22 |
| −1 | 1 | 3 | 1313 | 1274 | 70 |
| 1 | 1 | 3 | 454 | 425 | 23 |
| 3 | 1 | 3 | 365 | 365 | 19 |
| 5 | 1 | 3 | 132 | 139 | 10 |
| 7 | 1 | 3 | 196 | 192 | 11 |
| 9 | 1 | 3 | 82 | 72 | 13 |
| 11 | 1 | 3 | 219 | 227 | 8 |
| 13 | 1 | 3 | 249 | 254 | 11 |
| −5 | 1 | 5 | 131 | 141 | 6 |
| −3 | 1 | 5 | 185 | 183 | 10 |
| −1 | 1 | 5 | 945 | 915 | 50 |
| 3 | 1 | 5 | 646 | 629 | 33 |
| 5 | 1 | 5 | 147 | 153 | 10 |
| 7 | 1 | 5 | 383 | 390 | 16 |
| 9 | 1 | 5 | 202 | 199 | 8 |
| 11 | 1 | 5 | 125 | 121 | 7 |
| 17 | 1 | 5 | 50 | 71 | 6 |
| −24 | 2 | 5 | 47 | 50 | 21 |
| −22 | 2 | 5 | 69 | 61 | 15 |
| −20 | 2 | 5 | 126 | 133 | 12 |
| −18 | 2 | 5 | 356 | 342 | 18 |
| −16 | 2 | 5 | 262 | 263 | 14 |
| −14 | 2 | 5 | 348 | 398 | 20 |
| −4 | 2 | 5 | 489 | 472 | 23 |
| −2 | 2 | 5 | 432 | 419 | 23 |
| 0 | 2 | 5 | 297 | 275 | 16 |
| 2 | 2 | 5 | 492 | 480 | 27 |
| 4 | 2 | 5 | 386 | 364 | 20 |
| 6 | 2 | 5 | 192 | 199 | 8 |
| 8 | 2 | 5 | 27 | 31 | 26 |
| 16 | 2 | 5 | 93 | 90 | 10 |
| 18 | 2 | 5 | 87 | 79 | 8 |
| −23 | 3 | 5 | 9 | 51 | 9 |
| −21 | 3 | 5 | 45 | 64 | 28 |
| −19 | 3 | 5 | 211 | 190 | 11 |
| 5 | 3 | 5 | 197 | 194 | 12 |
| 11 | 3 | 5 | 86 | 91 | 12 |
| 13 | 3 | 5 | 37 | 27 | 36 |
| 15 | 3 | 5 | 48 | 36 | 20 |
| 17 | 3 | 5 | 19 | 19 | 19 |
| 8 | 4 | 5 | 83 | 81 | 11 |
| 10 | 4 | 5 | 43 | 46 | 28 |
| 12 | 4 | 5 | 29 | 42 | 29 |
| 14 | 4 | 5 | 23 | 23 | 23 |
| −14 | −6 | 6 | 46 | 62 | 8 |
| −12 | −6 | 6 | 68 | 64 | 5 |
| −10 | −6 | 6 | 40 | 41 | 9 |
| −8 | −6 | 6 | 17 | 12 | 17 |
| −6 | −6 | 6 | 121 | 118 | 5 |
| −4 | −6 | 6 | 106 | 102 | 4 |
| 0 | −6 | 6 | 35 | 41 | 20 |
| 2 | −6 | 6 | 71 | 72 | 9 |
| 4 | −6 | 6 | 33 | 28 | 26 |
| 6 | −6 | 6 | 34 | 32 | 20 |
| −19 | −5 | 6 | 49 | 42 | 7 |
| −17 | −5 | 6 | 99 | 102 | 5 |
| −15 | −5 | 6 | 143 | 132 | 12 |
| −13 | −5 | 6 | 151 | 148 | 6 |
| −11 | −5 | 6 | 82 | 94 | 8 |
| −9 | −5 | 6 | 34 | 38 | 15 |
| −7 | −5 | 6 | 132 | 132 | 6 |
| −5 | −5 | 6 | 179 | 173 | 7 |
| −3 | −5 | 6 | 106 | 93 | 5 |
| −1 | −5 | 6 | 167 | 167 | 6 |
| 1 | −5 | 6 | 115 | 129 | 8 |
| 3 | −5 | 6 | 126 | 136 | 8 |
| 5 | −5 | 6 | 65 | 91 | 11 |
| 7 | −5 | 6 | 4 | 29 | 3 |
| 9 | −5 | 6 | 0 | 39 | 1 |
| 11 | −5 | 6 | 0 | 14 | 1 |
| −22 | −4 | 6 | 43 | 35 | 7 |
| −20 | −4 | 6 | 61 | 61 | 7 |
| −18 | −4 | 6 | 55 | 66 | 7 |
| −16 | −4 | 6 | 188 | 198 | 6 |
| −14 | −4 | 6 | 59 | 61 | 8 |
| −12 | −4 | 6 | 362 | 354 | 8 |
| −10 | −4 | 6 | 209 | 193 | 5 |
| −8 | −4 | 6 | 368 | 368 | 7 |
| −6 | −4 | 6 | 57 | 58 | 4 |
| −4 | −4 | 6 | 269 | 248 | 6 |
| −2 | −4 | 6 | 243 | 228 | 7 |
| 0 | −4 | 6 | 255 | 227 | 7 |
| 2 | −4 | 6 | 33 | 19 | 32 |
| 4 | −4 | 6 | 198 | 185 | 12 |
| 6 | −4 | 6 | 149 | 161 | 11 |
| 8 | −4 | 6 | 19 | 12 | 18 |
| 10 | −4 | 6 | 6 | 19 | 5 |
| 12 | −4 | 6 | 27 | 22 | 27 |
| −23 | −3 | 6 | 96 | 92 | 5 |
| −21 | −3 | 6 | 131 | 119 | 6 |
| −19 | −3 | 6 | 27 | 33 | 26 |
| −17 | −3 | 6 | 244 | 221 | 7 |
| −15 | −3 | 6 | 188 | 174 | 5 |
| −13 | −3 | 6 | 241 | 239 | 5 |
| −11 | −3 | 6 | 196 | 198 | 4 |
| −5 | −3 | 8 | 335 | 316 | 9 |
| −3 | −3 | 8 | 156 | 163 | 5 |
| −1 | −3 | 8 | 296 | 270 | 8 |
| 1 | −3 | 8 | 128 | 131 | 10 |
| 3 | −3 | 8 | 231 | 223 | 12 |
| 5 | −3 | 8 | 171 | 162 | 11 |
| 7 | −3 | 8 | 4 | 19 | 3 |
| −24 | −2 | 8 | 101 | 101 | 10 |
| −22 | −2 | 8 | 134 | 115 | 13 |
| −20 | −2 | 8 | 352 | 327 | 12 |
| −18 | −2 | 8 | 390 | 372 | 11 |
| −16 | −2 | 8 | 325 | 326 | 8 |
| −14 | −2 | 8 | 302 | 296 | 7 |
| −12 | −2 | 8 | 165 | 162 | 5 |

TABLE 8-continued

Observed and calculated structure factors for 24F2-DM.

| h | k | l | 10Fc | 10Fc | 10s |
|---|---|---|------|------|-----|
| −10 | −2 | 8 | 382 | 351 | 20 |
| −8 | −2 | 8 | 410 | 387 | 21 |
| −6 | −2 | 8 | 320 | 283 | 16 |
| −4 | −2 | 8 | 166 | 145 | 11 |
| −2 | −2 | 8 | 215 | 198 | 13 |
| 2 | −2 | 8 | 226 | 235 | 10 |
| 4 | −2 | 8 | 226 | 232 | 9 |
| 6 | −2 | 8 | 328 | 307 | 12 |
| 8 | −2 | 8 | 174 | 172 | 8 |
| 10 | −2 | 8 | 55 | 60 | 6 |
| 12 | −2 | 8 | 73 | 91 | 6 |
| 14 | −2 | 8 | 15 | 7 | 15 |
| −25 | −1 | 8 | 77 | 70 | 10 |
| −23 | −1 | 8 | 36 | 34 | 35 |
| −21 | −1 | 8 | 16 | 24 | 16 |
| −19 | −1 | 8 | 102 | 89 | 7 |
| −17 | −1 | 8 | 222 | 220 | 9 |
| −15 | −1 | 8 | 225 | 235 | 7 |
| −13 | −1 | 8 | 417 | 397 | 22 |
| −11 | −1 | 8 | 315 | 282 | 17 |
| −9 | −1 | 8 | 1151 | 1082 | 60 |
| −7 | −1 | 8 | 210 | 216 | 12 |
| −5 | −1 | 8 | 140 | 152 | 10 |
| −3 | −1 | 8 | 618 | 660 | 32 |
| −1 | −1 | 8 | 642 | 598 | 34 |
| 1 | −1 | 8 | 188 | 203 | 11 |
| 3 | −1 | 8 | 187 | 200 | 8 |
| 5 | −1 | 8 | 104 | 96 | 6 |
| 7 | −1 | 8 | 234 | 236 | 10 |
| 9 | −1 | 8 | 155 | 143 | 8 |
| 11 | −1 | 8 | 155 | 165 | 8 |
| 13 | −1 | 8 | 82 | 85 | 7 |
| 15 | −1 | 8 | 40 | 43 | 11 |
| −26 | 0 | 8 | 47 | 33 | 17 |
| −24 | 0 | 8 | 43 | 54 | 21 |
| −22 | 0 | 8 | 61 | 68 | 14 |
| −20 | 0 | 8 | 18 | 50 | 18 |
| −18 | 0 | 8 | 0 | 13 | 1 |
| −16 | 0 | 8 | 233 | 238 | 7 |
| −14 | 0 | 8 | 659 | 627 | 34 |
| −12 | 0 | 8 | 75 | 81 | 14 |
| −10 | 0 | 8 | 120 | 111 | 11 |
| −8 | 0 | 8 | 419 | 407 | 15 |
| −6 | 0 | 8 | 180 | 190 | 7 |
| −4 | 0 | 8 | 30 | 15 | 29 |
| −2 | 0 | 8 | 188 | 184 | 11 |
| 0 | 0 | 8 | 1184 | 1393 | 61 |
| 2 | 0 | 8 | 206 | 195 | 12 |
| 4 | 0 | 8 | 550 | 544 | 12 |
| 6 | 0 | 8 | 0 | 8 | 1 |
| 8 | 0 | 8 | 46 | 41 | 8 |
| 10 | 0 | 8 | 0 | 19 | 1 |
| 12 | 0 | 8 | 64 | 54 | 9 |
| 14 | 0 | 8 | 73 | 78 | 7 |
| 16 | 0 | 8 | 0 | 14 | 1 |
| −25 | 1 | 8 | 53 | 70 | 11 |
| −23 | 1 | 8 | 20 | 54 | 20 |
| −21 | 1 | 8 | 16 | 24 | 16 |
| −19 | 1 | 8 | 109 | 88 | 11 |
| −17 | 1 | 8 | 240 | 219 | 12 |
| −15 | 1 | 8 | 229 | 236 | 12 |
| −9 | 1 | 8 | 1168 | 1081 | 59 |
| −7 | 1 | 8 | 219 | 215 | 12 |
| −5 | 1 | 8 | 151 | 158 | 10 |
| −3 | 1 | 8 | 659 | 658 | 31 |
| −1 | 1 | 8 | 669 | 598 | 33 |
| 1 | 1 | 8 | 210 | 204 | 11 |
| 3 | 1 | 8 | 182 | 199 | 7 |
| 5 | 1 | 8 | 108 | 97 | 6 |
| 7 | 1 | 8 | 224 | 237 | 10 |
| 9 | 1 | 8 | 143 | 141 | 11 |
| 11 | 1 | 8 | 165 | 164 | 20 |
| 13 | 1 | 8 | 107 | 86 | 10 |
| −15 | −5 | 11 | 22 | 23 | 22 |
| −13 | −5 | 11 | 60 | 45 | 16 |
| −11 | −5 | 11 | 46 | 33 | 10 |
| −9 | −5 | 11 | 5 | 8 | 5 |
| −7 | −5 | 11 | 197 | 202 | 7 |
| −5 | −5 | 11 | 81 | 85 | 9 |
| −3 | −5 | 11 | 136 | 152 | 9 |
| −1 | −5 | 11 | 85 | 77 | 9 |
| 1 | −5 | 11 | 15 | 30 | 14 |
| 3 | −5 | 11 | 65 | 49 | 10 |
| −22 | −4 | 11 | 35 | 37 | 29 |
| −20 | −4 | 11 | 41 | 34 | 40 |
| −18 | −4 | 11 | 0 | 12 | 1 |
| −16 | −4 | 11 | 100 | 97 | 4 |
| −14 | −4 | 11 | 83 | 83 | 5 |
| −12 | −4 | 11 | 35 | 91 | 17 |
| −10 | −4 | 11 | 109 | 110 | 10 |
| −8 | −4 | 11 | 161 | 189 | 10 |
| −6 | −4 | 11 | 108 | 123 | 5 |
| −4 | −4 | 11 | 252 | 249 | 8 |
| −2 | −4 | 11 | 129 | 121 | 9 |
| 0 | −4 | 11 | 197 | 191 | 12 |
| 2 | −4 | 11 | 67 | 58 | 12 |
| 4 | −4 | 11 | 94 | 102 | 10 |
| 6 | −4 | 11 | 18 | 33 | 17 |
| −23 | −3 | 11 | 18 | 8 | 18 |
| −21 | −3 | 11 | 11 | 15 | 10 |
| −19 | −3 | 11 | 81 | 81 | 6 |
| −17 | −3 | 11 | 124 | 150 | 6 |
| −15 | −3 | 11 | 60 | 64 | 7 |
| −13 | −3 | 11 | 186 | 172 | 5 |
| −11 | −3 | 11 | 74 | 58 | 7 |
| −9 | −3 | 11 | 83 | 75 | 9 |
| −7 | −3 | 11 | 182 | 160 | 9 |
| −5 | −3 | 11 | 290 | 281 | 9 |
| −3 | −3 | 11 | 251 | 235 | 8 |
| −1 | −3 | 11 | 236 | 226 | 8 |
| 1 | −3 | 11 | 126 | 112 | 9 |
| 3 | −3 | 11 | 0 | 40 | 1 |
| −26 | −2 | 11 | 43 | 47 | 20 |
| −24 | −2 | 11 | 99 | 87 | 7 |
| −22 | −2 | 11 | 43 | 59 | 10 |
| −20 | −2 | 11 | 39 | 56 | 13 |
| −18 | −2 | 11 | 124 | 150 | 6 |
| −16 | −2 | 11 | 200 | 191 | 7 |
| −14 | −2 | 11 | 89 | 108 | 8 |
| −12 | −2 | 11 | 46 | 51 | 12 |
| −10 | −2 | 11 | 192 | 174 | 5 |
| −8 | −2 | 11 | 241 | 244 | 5 |
| −6 | −2 | 11 | 129 | 130 | 4 |
| −4 | −2 | 11 | 270 | 288 | 8 |
| −2 | −2 | 11 | 176 | 173 | 7 |
| 0 | −2 | 11 | 93 | 74 | 5 |
| 2 | −2 | 11 | 99 | 95 | 5 |
| 4 | −2 | 11 | 289 | 298 | 12 |
| 6 | −2 | 11 | 25 | 24 | 17 |
| 8 | −2 | 11 | 135 | 130 | 6 |
| 10 | −2 | 11 | 12 | 26 | 12 |
| −27 | −1 | 11 | 18 | 9 | 18 |
| −25 | −1 | 11 | 63 | 56 | 10 |
| −23 | −1 | 11 | 33 | 48 | 23 |
| −21 | −1 | 11 | 100 | 99 | 8 |
| −19 | −1 | 11 | 56 | 63 | 12 |
| −17 | −1 | 11 | 210 | 219 | 7 |
| −15 | −1 | 11 | 47 | 49 | 9 |
| −13 | −1 | 11 | 260 | 259 | 7 |
| −11 | −1 | 11 | 78 | 91 | 6 |
| −9 | −1 | 11 | 383 | 337 | 13 |
| −7 | −1 | 11 | 314 | 311 | 16 |
| −5 | −1 | 11 | 111 | 88 | 7 |
| −3 | −1 | 11 | 132 | 140 | 5 |
| −1 | −1 | 11 | 100 | 93 | 4 |
| 1 | −1 | 11 | 21 | 41 | 20 |
| 3 | −1 | 11 | 120 | 108 | 6 |
| 5 | −1 | 11 | 76 | 77 | 6 |
| 7 | −1 | 11 | 18 | 14 | 17 |
| 9 | −1 | 11 | 59 | 72 | 7 |
| 11 | −1 | 11 | 117 | 108 | 7 |
| 13 | −1 | 11 | 4 | 9 | 4 |

TABLE 8-continued

Observed and calculated structure factors for 24F2-DM.

| h | k | l | 10Fo | 10Fc | 10s |
|---|---|---|------|------|-----|
| −26 | 0 | 11 | 33 | 14 | 32 |
| −24 | 0 | 11 | 94 | 104 | 10 |
| −22 | 0 | 11 | 37 | 27 | 23 |
| −20 | 0 | 11 | 130 | 127 | 7 |
| −18 | 0 | 11 | 113 | 111 | 7 |
| −16 | 0 | 11 | 106 | 120 | 6 |
| −14 | 0 | 11 | 205 | 227 | 6 |
| −12 | 0 | 11 | 119 | 108 | 8 |
| −4 | −4 | 14 | 80 | 87 | 11 |
| −2 | −4 | 14 | 129 | 117 | 9 |
| 0 | −4 | 14 | 61 | 67 | 12 |
| 2 | −4 | 14 | 0 | 32 | 1 |
| −23 | −3 | 14 | 48 | 38 | 9 |
| −21 | −3 | 14 | 123 | 107 | 5 |
| −19 | −3 | 14 | 9 | 30 | 9 |
| −17 | −3 | 14 | 221 | 251 | 8 |
| −15 | −3 | 14 | 62 | 68 | 7 |
| −13 | −3 | 14 | 96 | 97 | 12 |
| −11 | −3 | 14 | 280 | 268 | 9 |
| −9 | −3 | 14 | 181 | 174 | 24 |
| −7 | −3 | 14 | 109 | 109 | 10 |
| −5 | −3 | 14 | 256 | 251 | 14 |
| −3 | −3 | 14 | 212 | 224 | 7 |
| −26 | −2 | 14 | 46 | 19 | 16 |
| −24 | −2 | 14 | 61 | 53 | 7 |
| −22 | −2 | 14 | 22 | 35 | 21 |
| −20 | −2 | 14 | 116 | 134 | 5 |
| −18 | −2 | 14 | 161 | 162 | 7 |
| −16 | −2 | 14 | 110 | 119 | 7 |
| −14 | −2 | 14 | 273 | 260 | 7 |
| −12 | −2 | 14 | 244 | 229 | 6 |
| −10 | −2 | 14 | 92 | 82 | 4 |
| −8 | −2 | 14 | 338 | 342 | 9 |
| −6 | −2 | 14 | 204 | 194 | 9 |
| −4 | −2 | 14 | 337 | 382 | 16 |
| −2 | −2 | 14 | 130 | 141 | 6 |
| 0 | −2 | 14 | 119 | 127 | 7 |
| 2 | −2 | 14 | 41 | 51 | 9 |
| 4 | −2 | 14 | 77 | 71 | 6 |
| −27 | −1 | 14 | 37 | 25 | 22 |
| −25 | −1 | 14 | 68 | 62 | 8 |
| −23 | −1 | 14 | 35 | 57 | 17 |
| −21 | −1 | 14 | 48 | 60 | 10 |
| −19 | −1 | 14 | 96 | 93 | 6 |
| −17 | −1 | 14 | 84 | 95 | 6 |
| −15 | −1 | 14 | 130 | 127 | 5 |
| −13 | −1 | 14 | 159 | 150 | 5 |
| −11 | −1 | 14 | 115 | 112 | 4 |
| −9 | −1 | 14 | 229 | 217 | 6 |
| −7 | −1 | 14 | 114 | 115 | 4 |
| −5 | −1 | 14 | 188 | 188 | 6 |
| −3 | −1 | 14 | 34 | 21 | 11 |
| −1 | −1 | 14 | 45 | 42 | 11 |
| 1 | −1 | 14 | 23 | 34 | 22 |
| 3 | −1 | 14 | 30 | 36 | 17 |
| 5 | −1 | 14 | 65 | 80 | 7 |
| 7 | −1 | 14 | 68 | 58 | 7 |
| 9 | −1 | 14 | 48 | 37 | 6 |
| −26 | −1 | 14 | 40 | 39 | 15 |
| −24 | −1 | 14 | 90 | 83 | 10 |
| −22 | 0 | 14 | 63 | 49 | 10 |
| −20 | 0 | 14 | 27 | 34 | 27 |
| −18 | 0 | 14 | 70 | 84 | 7 |
| −16 | 0 | 14 | 0 | 4 | 1 |
| −14 | 0 | 14 | 97 | 35 | 7 |
| −12 | 0 | 14 | 360 | 349 | 14 |
| −10 | 0 | 14 | 87 | 94 | 6 |
| −8 | 0 | 14 | 301 | 284 | 10 |
| −6 | 0 | 14 | 233 | 228 | 6 |
| −4 | 0 | 14 | 218 | 201 | 6 |
| −2 | 0 | 14 | 219 | 215 | 6 |
| 0 | 0 | 14 | 141 | 130 | 5 |
| 2 | 0 | 14 | 91 | 72 | 5 |
| 4 | 0 | 14 | 53 | 54 | 10 |
| 6 | 0 | 14 | 0 | 8 | 1 |
| 8 | 0 | 14 | 0 | 3 | 1 |
| −25 | 1 | 14 | 63 | 62 | 12 |
| −23 | 1 | 14 | 59 | 57 | 15 |
| −21 | 1 | 14 | 65 | 60 | 13 |
| −19 | 1 | 14 | 95 | 94 | 10 |
| −17 | 1 | 14 | 88 | 96 | 11 |
| −15 | 1 | 14 | 126 | 128 | 9 |
| −13 | 1 | 14 | 141 | 149 | 7 |
| −11 | 1 | 14 | 110 | 111 | 6 |
| −9 | 1 | 14 | 227 | 218 | 9 |
| −7 | 1 | 14 | 113 | 115 | 6 |
| −5 | 1 | 14 | 183 | 190 | 6 |
| −3 | 1 | 14 | 25 | 19 | 24 |
| −1 | 1 | 14 | 41 | 42 | 23 |
| 1 | 1 | 14 | 28 | 33 | 27 |
| 3 | 1 | 14 | 34 | 37 | 34 |
| 5 | 1 | 14 | 76 | 80 | 6 |
| −16 | 2 | 14 | 106 | 118 | 10 |
| −14 | 2 | 14 | 264 | 260 | 11 |
| −12 | 2 | 14 | 238 | 229 | 11 |
| −6 | 2 | 17 | 83 | 101 | 7 |
| −4 | 2 | 17 | 72 | 86 | 7 |
| −2 | 2 | 17 | 14 | 30 | 14 |
| 0 | 2 | 17 | 42 | 25 | 11 |
| 2 | 2 | 17 | 15 | 32 | 14 |
| −15 | 3 | 17 | 67 | 83 | 15 |
| −13 | 3 | 17 | 97 | 78 | 10 |
| −11 | 3 | 17 | 92 | 91 | 11 |
| −9 | 3 | 17 | 103 | 97 | 9 |
| −7 | 3 | 17 | 50 | 62 | 20 |
| −5 | 3 | 17 | 103 | 101 | 6 |
| −3 | 3 | 17 | 142 | 124 | 7 |
| −1 | 3 | 17 | 46 | 36 | 9 |
| −10 | 4 | 17 | 18 | 48 | 17 |
| −8 | 4 | 17 | 20 | 52 | 20 |
| −6 | 4 | 17 | 50 | 51 | 14 |
| −4 | 4 | 17 | 36 | 42 | 19 |
| −16 | −4 | 18 | 31 | 23 | 14 |
| −14 | −4 | 18 | 43 | 45 | 8 |
| −12 | −4 | 18 | 82 | 80 | 5 |
| −10 | −4 | 18 | 75 | 50 | 9 |
| −8 | −4 | 18 | 0 | 30 | 1 |
| −21 | −3 | 18 | 20 | 22 | 20 |
| −19 | −3 | 18 | 50 | 49 | 19 |
| −17 | −3 | 18 | 29 | 47 | 23 |
| −15 | −3 | 18 | 135 | 123 | 6 |
| −13 | −3 | 18 | 19 | 27 | 16 |
| −11 | −3 | 18 | 154 | 137 | 8 |
| −9 | −3 | 18 | 88 | 78 | 9 |
| −7 | −3 | 18 | 89 | 86 | 6 |
| −24 | −2 | 18 | 0 | 8 | 1 |
| −22 | −2 | 18 | 131 | 107 | 8 |
| −20 | −2 | 18 | 43 | 42 | 10 |
| −18 | −2 | 18 | 22 | 23 | 22 |
| −16 | −2 | 18 | 54 | 44 | 6 |
| −14 | −2 | 18 | 78 | 104 | 12 |
| −12 | −2 | 18 | 64 | 68 | 10 |
| −10 | −2 | 18 | 102 | 96 | 7 |
| −8 | −2 | 18 | 42 | 45 | 12 |
| −6 | −2 | 18 | 121 | 136 | 7 |
| −4 | −2 | 18 | 40 | 43 | 12 |
| −2 | −2 | 18 | 79 | 76 | 6 |
| −25 | −1 | 18 | 56 | 62 | 7 |
| −23 | −1 | 18 | 138 | 113 | 7 |
| −21 | −1 | 18 | 111 | 108 | 5 |
| −19 | −1 | 18 | 0 | 17 | 1 |
| −17 | −1 | 18 | 128 | 125 | 19 |
| −15 | −1 | 18 | 119 | 134 | 9 |
| −13 | −1 | 18 | 187 | 204 | 10 |
| −11 | −1 | 18 | 174 | 160 | 10 |
| −9 | −1 | 18 | 109 | 88 | 5 |
| −7 | −1 | 18 | 150 | 139 | 8 |
| −5 | −1 | 18 | 78 | 67 | 7 |
| −3 | −1 | 18 | 40 | 37 | 14 |
| −1 | 0 | 18 | 69 | 61 | 8 |
| 1 | 0 | 18 | 36 | 31 | 13 |
| −24 | 0 | 18 | 81 | 79 | 6 |

TABLE 8-continued

Observed and calculated structure factors for 24F2-DM.

| h | k | l | 10Fo | 10Fc | 10s |
|---|---|---|------|------|-----|
| −20 | 0 | 18 | 56 | 51 | 10 |
| −18 | 0 | 18 | 48 | 51 | 11 |
| −16 | 0 | 18 | 71 | 86 | 11 |
| −14 | 0 | 18 | 81 | 100 | 8 |
| −12 | 0 | 18 | 123 | 135 | 6 |
| −10 | 0 | 18 | 186 | 221 | 11 |
| −8 | 0 | 18 | 182 | 223 | 11 |
| −6 | 0 | 18 | 153 | 140 | 5 |
| −4 | 0 | 18 | 55 | 61 | 7 |
| −2 | 0 | 18 | 44 | 17 | 12 |
| 0 | 0 | 18 | 44 | 41 | 11 |
| 10 | −2 | 1 | 444 | 448 | 14 |
| 12 | −2 | 1 | 213 | 219 | 6 |
| 14 | −2 | 1 | 66 | 68 | 9 |
| 16 | −2 | 1 | 111 | 111 | 7 |
| 18 | −2 | 1 | 26 | 51 | 25 |
| 20 | −2 | 1 | 24 | 13 | 24 |
| −23 | −1 | 1 | 42 | 29 | 12 |
| −21 | −1 | 1 | 76 | 65 | 8 |
| −19 | −1 | 1 | 58 | 59 | 8 |
| −17 | −1 | 1 | 66 | 68 | 8 |
| −15 | −1 | 1 | 66 | 74 | 6 |
| −13 | −1 | 1 | 93 | 95 | 5 |
| −11 | −1 | 1 | 727 | 708 | 37 |
| −9 | −1 | 1 | 342 | 398 | 18 |
| −7 | −1 | 1 | 436 | 450 | 16 |
| −5 | −1 | 1 | 1157 | 1181 | 41 |
| −3 | −1 | 1 | 1214 | 1185 | 47 |
| −1 | −1 | 1 | 773 | 738 | 21 |
| 3 | −1 | 1 | 556 | 514 | 19 |
| 5 | −1 | 1 | 602 | 581 | 30 |
| 7 | −1 | 1 | 149 | 182 | 9 |
| 9 | −1 | 1 | 197 | 196 | 11 |
| 11 | −1 | 1 | 289 | 283 | 9 |
| 13 | −1 | 1 | 143 | 142 | 6 |
| 15 | −1 | 1 | 98 | 97 | 6 |
| 17 | −1 | 1 | 78 | 88 | 9 |
| 19 | −1 | 1 | 117 | 92 | 7 |
| 21 | −1 | 1 | 44 | 47 | 12 |
| −22 | 0 | 1 | 70 | 67 | 10 |
| −20 | 0 | 1 | 75 | 56 | 11 |
| −18 | 0 | 1 | 0 | 50 | 1 |
| −16 | 0 | 1 | 65 | 74 | 11 |
| −14 | 0 | 1 | 68 | 53 | 9 |
| −12 | 0 | 1 | 52 | 67 | 21 |
| −10 | 0 | 1 | 460 | 501 | 24 |
| −8 | 0 | 1 | 114 | 127 | 9 |
| −6 | 0 | 1 | 486 | 469 | 25 |
| −4 | 0 | 1 | 1594 | 1546 | 32 |
| −2 | 0 | 1 | 314 | 326 | 16 |
| 0 | 0 | 1 | 229 | 229 | 8 |
| 2 | 0 | 1 | 495 | 493 | 25 |
| 4 | 0 | 1 | 1308 | 1448 | 67 |
| 6 | 0 | 1 | 94 | 111 | 7 |
| 8 | 0 | 1 | 218 | 255 | 12 |
| 10 | 0 | 1 | 132 | 149 | 9 |
| 12 | 0 | 1 | 203 | 207 | 8 |
| 14 | 0 | 1 | 200 | 204 | 6 |
| 16 | 0 | 1 | 128 | 121 | 6 |
| 18 | 0 | 1 | 99 | 91 | 10 |
| −21 | 1 | 1 | 77 | 46 | 12 |
| −19 | 1 | 1 | 65 | 58 | 13 |
| −17 | 1 | 1 | 53 | 68 | 19 |
| −15 | 1 | 1 | 80 | 73 | 10 |
| −13 | 1 | 1 | 106 | 94 | 12 |
| −11 | 1 | 1 | 726 | 709 | 37 |
| −7 | 1 | 1 | 457 | 447 | 22 |
| −5 | 1 | 1 | 1142 | 1182 | 59 |
| −3 | 1 | 1 | 1172 | 1188 | 43 |
| −1 | 1 | 1 | 736 | 735 | 28 |
| 1 | 1 | 1 | 2044 | 1952 | 105 |
| 3 | 1 | 1 | 540 | 517 | 29 |
| 5 | 1 | 1 | 582 | 584 | 31 |
| 7 | 1 | 1 | 166 | 182 | 9 |
| 9 | 1 | 1 | 209 | 197 | 11 |
| 11 | 1 | 1 | 293 | 283 | 10 |
| 13 | 1 | 1 | 160 | 141 | 7 |
| 15 | 1 | 1 | 87 | 96 | 11 |
| 17 | 1 | 1 | 78 | 88 | 11 |
| 19 | 1 | 1 | 92 | 91 | 11 |
| −22 | 2 | 1 | 99 | 77 | 9 |
| −20 | 2 | 1 | 98 | 106 | 11 |
| −18 | 2 | 1 | 40 | 43 | 37 |
| −16 | 2 | 1 | 141 | 131 | 10 |
| −14 | 2 | 1 | 90 | 82 | 11 |
| −12 | 2 | 1 | 131 | 136 | 9 |
| −10 | 2 | 1 | 237 | 250 | 15 |
| −8 | 2 | 1 | 236 | 209 | 14 |
| −6 | 2 | 1 | 378 | 371 | 18 |
| −4 | 2 | 1 | 305 | 301 | 14 |
| −2 | 2 | 1 | 365 | 353 | 18 |
| 0 | 2 | 1 | 240 | 231 | 12 |
| 2 | 2 | 1 | 371 | 331 | 19 |
| 4 | 2 | 1 | 258 | 257 | 14 |
| 6 | 2 | 1 | 1148 | 1115 | 59 |
| 8 | 2 | 1 | 351 | 830 | 18 |
| 10 | 2 | 1 | 444 | 449 | 15 |
| 12 | 2 | 1 | 213 | 220 | 10 |
| 15 | 1 | 3 | 0 | 23 | 1 |
| 19 | 1 | 3 | 56 | 36 | 12 |
| −24 | 2 | 3 | 31 | 50 | 31 |
| −22 | 2 | 3 | 91 | 74 | 11 |
| −20 | 2 | 3 | 61 | 43 | 16 |
| −18 | 2 | 3 | 153 | 148 | 10 |
| −16 | 2 | 3 | 79 | 74 | 15 |
| −14 | 2 | 3 | 171 | 176 | 12 |
| −4 | 2 | 3 | 408 | 415 | 19 |
| −2 | 2 | 3 | 33 | 33 | 23 |
| 0 | 2 | 3 | 400 | 377 | 21 |
| 2 | 2 | 3 | 500 | 477 | 26 |
| 4 | 2 | 3 | 961 | 390 | 49 |
| 6 | 2 | 3 | 530 | 505 | 27 |
| 8 | 2 | 3 | 333 | 531 | 12 |
| 10 | 2 | 3 | 156 | 150 | 8 |
| 12 | 2 | 3 | 129 | 125 | 15 |
| 14 | 2 | 3 | 154 | 167 | 10 |
| 20 | 2 | 3 | 56 | 43 | 10 |
| −21 | 3 | 3 | 63 | 52 | 15 |
| −19 | 3 | 3 | 35 | 61 | 34 |
| −17 | 3 | 3 | 0 | 12 | 1 |
| −15 | 3 | 3 | 76 | 92 | 15 |
| 7 | 3 | 3 | 252 | 250 | 14 |
| 9 | 3 | 3 | 168 | 160 | 12 |
| 11 | 3 | 3 | 243 | 236 | 14 |
| 17 | 3 | 3 | 53 | 43 | 17 |
| 19 | 3 | 3 | 0 | 11 | 1 |
| 10 | 4 | 3 | 123 | 120 | 9 |
| 12 | 4 | 3 | 41 | 46 | 92 |
| 14 | 4 | 3 | 0 | 20 | 1 |
| 16 | 4 | 3 | 29 | 40 | 29 |
| −14 | −6 | 4 | 20 | 21 | 17 |
| −12 | −6 | 4 | 55 | 58 | 7 |
| −10 | −6 | 4 | 56 | 46 | 5 |
| −8 | −6 | 4 | 35 | 38 | 10 |
| −6 | −6 | 4 | 96 | 95 | 4 |
| −4 | −6 | 4 | 37 | 30 | 7 |
| −2 | −6 | 4 | 54 | 51 | 4 |
| 0 | −6 | 4 | 59 | 53 | 4 |
| 2 | −6 | 4 | 157 | 144 | 9 |
| 4 | −6 | 4 | 47 | 52 | 13 |
| 6 | −6 | 4 | 33 | 32 | 27 |
| 8 | −6 | 4 | 44 | 49 | 13 |
| −17 | −5 | 4 | 35 | 42 | 9 |
| −15 | −5 | 4 | 39 | 54 | 17 |
| −13 | −5 | 4 | 51 | 57 | 8 |
| −11 | −5 | 4 | 120 | 256 | 8 |
| −9 | −5 | 4 | 125 | 212 | 7 |
| −7 | −5 | 4 | 44 | 37 | 9 |
| −5 | −5 | 4 | 55 | 52 | 7 |
| −3 | −5 | 4 | 204 | 189 | 14 |
| −1 | −5 | 4 | 137 | 127 | 4 |
| 1 | −5 | 4 | 83 | 75 | 4 |

TABLE 8-continued

Observed and calculated structure factors for 24F2-DM.

| h | k | l | 10Fo | 10Fc | 10s |
|---|---|---|------|------|-----|
| 3 | −5 | 4 | 89 | 99 | 9 |
| 5 | −5 | 4 | 30 | 38 | 29 |
| 7 | −5 | 4 | 45 | 50 | 16 |
| 9 | −5 | 4 | 34 | 28 | 33 |
| 11 | −5 | 4 | 20 | 17 | 20 |
| 13 | −5 | 4 | 17 | 11 | 17 |
| −20 | −4 | 4 | 58 | 51 | 12 |
| −18 | −4 | 4 | 51 | 54 | 8 |
| −16 | −4 | 4 | 58 | 58 | 7 |
| −14 | −4 | 4 | 98 | 104 | 6 |
| −12 | −4 | 4 | 38 | 49 | 11 |
| −10 | −4 | 4 | 163 | 158 | 5 |
| −8 | −4 | 4 | 232 | 225 | 5 |
| −6 | −4 | 4 | 187 | 192 | 4 |
| −4 | −4 | 4 | 146 | 129 | 4 |
| −2 | −4 | 4 | 150 | 144 | 4 |
| 0 | −4 | 4 | 80 | 77 | 4 |
| 2 | −4 | 4 | 85 | 73 | 8 |
| 4 | −4 | 4 | 158 | 143 | 7 |
| 6 | −4 | 4 | 0 | 16 | 1 |
| 8 | −4 | 4 | 73 | 59 | 12 |
| 10 | −4 | 4 | 78 | 95 | 12 |
| 12 | −4 | 4 | 37 | 31 | 37 |
| 14 | −4 | 4 | 25 | 14 | 25 |
| −23 | −3 | 4 | 40 | 34 | 10 |
| −21 | −3 | 4 | 66 | 59 | 6 |
| −19 | −3 | 4 | 36 | 22 | 15 |
| −17 | −3 | 4 | 169 | 269 | 10 |
| −15 | −3 | 4 | 233 | 223 | 7 |
| −13 | −3 | 4 | 333 | 349 | 8 |
| −11 | −3 | 4 | 102 | 112 | 4 |
| −9 | −3 | 4 | 167 | 169 | 4 |
| −7 | −3 | 4 | 181 | 169 | 11 |
| −9 | −3 | 6 | 93 | 91 | 3 |
| −7 | −3 | 6 | 292 | 283 | 8 |
| −5 | −3 | 6 | 308 | 270 | 16 |
| −3 | −3 | 6 | 86 | 54 | 12 |
| −1 | −3 | 6 | 144 | 134 | 7 |
| 1 | −3 | 6 | 52 | 65 | 12 |
| 3 | −3 | 6 | 147 | 226 | 7 |
| 5 | −3 | 6 | 260 | 271 | 13 |
| 7 | −3 | 6 | 192 | 179 | 11 |
| 9 | −3 | 6 | 115 | 114 | 10 |
| −24 | −2 | 6 | 38 | 18 | 16 |
| −22 | −2 | 6 | 58 | 60 | 9 |
| −20 | −2 | 6 | 108 | 208 | 5 |
| −18 | −2 | 6 | 84 | 84 | 5 |
| −16 | −2 | 6 | 61 | 61 | 6 |
| −14 | −2 | 6 | 310 | 324 | 6 |
| −12 | −2 | 6 | 234 | 244 | 7 |
| −10 | −2 | 6 | 52 | 38 | 19 |
| −8 | −2 | 6 | 243 | 225 | 13 |
| −6 | −2 | 6 | 304 | 520 | 16 |
| −4 | −2 | 6 | 502 | 502 | 27 |
| −2 | −2 | 6 | 433 | 368 | 22 |
| 0 | −2 | 6 | 301 | 267 | 17 |
| 2 | −2 | 6 | 287 | 258 | 16 |
| 6 | −2 | 6 | 94 | 81 | 5 |
| 8 | −2 | 6 | 112 | 119 | 7 |
| 10 | −2 | 6 | 165 | 166 | 8 |
| 12 | −2 | 6 | 28 | 23 | 16 |
| 14 | −2 | 6 | 50 | 52 | 7 |
| 16 | −2 | 6 | 15 | 35 | 15 |
| −23 | −1 | 6 | 119 | 117 | 8 |
| −21 | −1 | 6 | 87 | 65 | 10 |
| −19 | −1 | 6 | 99 | 93 | 7 |
| −17 | −1 | 6 | 121 | 121 | 6 |
| −15 | −1 | 6 | 235 | 239 | 7 |
| −13 | −1 | 6 | 90 | 88 | 14 |
| −11 | −1 | 6 | 245 | 219 | 13 |
| −9 | −1 | 6 | 0 | 13 | 1 |
| −7 | −1 | 6 | 353 | 345 | 16 |
| −5 | −1 | 6 | 645 | 606 | 23 |
| −3 | −1 | 6 | 493 | 472 | 18 |
| −1 | −1 | 6 | 581 | 572 | 19 |
| 1 | −1 | 6 | 488 | 464 | 17 |
| 3 | −1 | 6 | 483 | 519 | 25 |
| 5 | −1 | 6 | 157 | 158 | 10 |
| 7 | −1 | 6 | 149 | 159 | 5 |
| 9 | −1 | 6 | 191 | 184 | 6 |
| 11 | −1 | 6 | 112 | 106 | 7 |
| 13 | −1 | 6 | 151 | 149 | 8 |
| 15 | −1 | 6 | 45 | 44 | 12 |
| 17 | −1 | 6 | 40 | 17 | 11 |
| −26 | 0 | 6 | 11 | 17 | 10 |
| −24 | 0 | 6 | 0 | 3 | 1 |
| −22 | 0 | 6 | 61 | 66 | 13 |
| −20 | 0 | 6 | 92 | 110 | 10 |
| −18 | 0 | 6 | 55 | 34 | 15 |
| −16 | 0 | 6 | 42 | 67 | 24 |
| −14 | 0 | 6 | 17 | 19 | 16 |
| −12 | 0 | 6 | 573 | 520 | 30 |
| −10 | 0 | 6 | 1062 | 977 | 54 |
| −8 | 0 | 6 | 1553 | 1406 | 80 |
| −6 | 0 | 6 | 592 | 550 | 21 |
| −4 | 0 | 6 | 276 | 283 | 10 |
| −2 | 0 | 6 | 85 | 103 | 5 |
| 0 | 0 | 6 | 205 | 181 | 8 |
| 2 | 0 | 6 | 615 | 731 | 31 |
| 4 | 0 | 6 | 99 | 105 | 9 |
| 6 | 0 | 6 | 184 | 162 | 11 |
| 8 | 0 | 6 | 86 | 86 | 6 |
| 10 | 0 | 6 | 88 | 91 | 10 |
| 12 | 0 | 6 | 102 | 99 | 5 |
| 14 | 0 | 6 | 160 | 149 | 6 |
| 16 | 0 | 6 | 134 | 119 | 9 |
| 18 | 0 | 6 | 25 | 16 | 25 |
| −25 | 1 | 6 | 0 | 13 | 1 |
| −23 | 1 | 6 | 100 | 116 | 10 |
| −21 | 1 | 6 | 92 | 85 | 11 |
| −19 | 1 | 6 | 102 | 93 | 12 |
| −17 | 1 | 6 | 123 | 119 | 10 |
| −15 | 1 | 6 | 249 | 138 | 12 |
| −13 | 1 | 6 | 88 | 89 | 14 |
| −11 | 1 | 6 | 236 | 220 | 14 |
| −9 | 1 | 6 | 24 | 11 | 24 |
| −7 | 1 | 6 | 344 | 345 | 13 |
| −5 | 1 | 6 | 655 | 606 | 33 |
| −3 | 1 | 6 | 523 | 473 | 25 |
| −1 | 1 | 6 | 513 | 572 | 31 |
| 15 | 1 | 8 | 43 | 43 | 12 |
| −24 | 2 | 8 | 99 | 100 | 11 |
| −22 | 2 | 8 | 99 | 114 | 15 |
| −20 | 2 | 8 | 370 | 327 | 17 |
| −18 | 2 | 8 | 395 | 372 | 19 |
| −6 | 2 | 8 | 302 | 282 | 17 |
| −4 | 2 | 8 | 166 | 145 | 12 |
| −2 | 2 | 8 | 215 | 197 | 13 |
| 0 | 2 | 8 | 253 | 238 | 15 |
| 2 | 2 | 8 | 238 | 235 | 9 |
| 4 | 2 | 8 | 216 | 231 | 7 |
| 6 | 2 | 8 | 308 | 308 | 9 |
| 8 | 2 | 8 | 173 | 272 | 7 |
| 10 | 2 | 8 | 52 | 60 | 10 |
| 12 | 2 | 8 | 84 | 91 | 7 |
| 14 | 2 | 8 | 17 | 7 | 17 |
| −23 | 3 | 8 | 34 | 19 | 33 |
| −1 | 3 | 8 | 275 | 269 | 15 |
| 1 | 3 | 8 | 135 | 131 | 9 |
| 3 | 3 | 8 | 223 | 224 | 12 |
| 5 | 3 | 8 | 159 | 161 | 12 |
| 7 | 3 | 8 | 32 | 17 | 31 |
| 9 | 3 | 8 | 45 | 50 | 14 |
| 11 | 3 | 8 | 152 | 147 | 8 |
| 13 | 3 | 8 | 0 | 19 | 1 |
| 4 | 4 | 8 | 159 | 162 | 11 |
| 6 | 4 | 8 | 109 | 108 | 9 |
| 8 | 4 | 8 | 51 | 38 | 17 |
| 10 | 4 | 8 | 75 | 45 | 20 |
| 12 | 4 | 8 | 45 | 18 | 25 |
| −12 | −6 | 9 | 0 | 25 | 1 |
| −10 | −6 | 9 | 78 | 92 | 7 |

TABLE 8-continued

Observed and calculated structure factors for 24F2-DM.

| h | k | l | 10Fc | 10Fc | 10s |
|---|---|---|------|------|-----|
| −8 | −6 | 9 | 56 | 55 | 6 |
| −4 | −6 | 9 | 92 | 91 | 7 |
| −2 | −6 | 9 | 30 | 23 | 29 |
| 0 | −6 | 9 | 35 | 32 | 19 |
| 2 | −6 | 9 | 26 | 33 | 25 |
| −19 | −5 | 9 | 18 | 19 | 18 |
| −17 | −5 | 9 | 0 | 15 | 1 |
| −15 | −5 | 9 | 0 | 25 | 1 |
| −13 | −5 | 9 | 23 | 41 | 22 |
| −11 | −5 | 9 | 137 | 132 | 5 |
| −9 | −5 | 9 | 138 | 142 | 6 |
| −7 | −5 | 9 | 60 | 64 | 13 |
| −5 | −5 | 9 | 114 | 125 | 5 |
| −3 | −5 | 9 | 200 | 232 | 11 |
| −1 | −5 | 9 | 49 | 45 | 13 |
| 1 | −5 | 9 | 62 | 80 | 10 |
| 3 | −5 | 9 | 70 | 57 | 10 |
| 5 | −5 | 9 | 78 | 72 | 9 |
| 7 | −5 | 9 | 30 | 29 | 30 |
| −22 | −4 | 9 | 38 | 31 | 15 |
| −20 | −4 | 9 | 29 | 42 | 21 |
| −18 | −4 | 9 | 64 | 68 | 7 |
| −16 | −4 | 9 | 220 | 206 | 7 |
| −14 | −4 | 9 | 204 | 197 | 5 |
| −12 | −4 | 9 | 165 | 167 | 6 |
| −10 | −4 | 9 | 108 | 94 | 6 |
| −8 | −4 | 9 | 73 | 65 | 7 |
| −6 | −4 | 9 | 79 | 74 | 6 |
| −4 | −4 | 9 | 0 | 16 | 1 |
| −2 | −4 | 9 | 93 | 76 | 10 |
| 0 | −4 | 9 | 92 | 95 | 10 |
| 2 | −4 | 9 | 133 | 141 | 9 |
| 4 | −4 | 9 | 93 | 96 | 10 |
| 6 | −4 | 9 | 0 | 21 | 1 |
| 8 | −4 | 9 | 64 | 72 | 13 |
| 10 | −4 | 9 | 60 | 55 | 12 |
| −23 | −3 | 9 | 46 | 40 | 14 |
| −21 | −3 | 9 | 61 | 63 | 7 |
| −19 | −3 | 9 | 112 | 119 | 10 |
| −17 | −3 | 9 | 88 | 79 | 6 |
| −15 | −3 | 9 | 92 | 96 | 10 |
| −13 | −3 | 9 | 58 | 87 | 8 |
| −11 | −3 | 9 | 44 | 48 | 8 |
| −9 | −3 | 9 | 165 | 158 | 5 |
| −7 | −3 | 9 | 225 | 222 | 6 |
| −5 | −3 | 9 | 234 | 234 | 7 |
| −3 | −3 | 9 | 116 | 114 | 5 |
| −1 | −3 | 9 | 377 | 362 | 11 |
| 1 | −3 | 9 | 303 | 293 | 15 |
| 3 | −3 | 9 | 378 | 364 | 18 |
| 5 | −3 | 9 | 191 | 206 | 13 |
| −24 | −2 | 9 | 46 | 50 | 19 |
| −22 | −2 | 9 | 41 | 30 | 17 |
| −20 | −2 | 9 | 234 | 226 | 7 |
| −18 | −2 | 9 | 132 | 124 | 5 |
| −10 | 0 | 11 | 36 | 46 | 36 |
| −8 | 0 | 11 | 402 | 406 | 21 |
| −6 | 0 | 11 | 227 | 226 | 13 |
| −4 | 0 | 11 | 656 | 677 | 34 |
| −2 | 0 | 11 | 66 | 80 | 5 |
| 0 | 0 | 11 | 332 | 331 | 7 |
| 2 | 0 | 11 | 116 | 119 | 4 |
| 4 | 0 | 11 | 42 | 43 | 8 |
| 6 | 0 | 11 | 113 | 108 | 5 |
| 8 | 0 | 11 | 8 | 11 | 8 |
| 10 | 0 | 11 | 31 | 27 | 21 |
| 12 | 0 | 11 | 48 | 27 | 9 |
| −27 | 1 | 11 | 0 | 9 | 1 |
| −25 | 1 | 11 | 38 | 56 | 37 |
| −23 | 1 | 11 | 2 | 48 | 2 |
| −21 | 1 | 11 | 101 | 100 | 11 |
| −19 | 1 | 11 | 64 | 64 | 15 |
| −17 | 1 | 11 | 203 | 218 | 8 |
| −15 | 1 | 11 | 40 | 48 | 25 |
| −13 | 1 | 11 | 256 | 260 | 14 |
| −11 | 1 | 11 | 83 | 90 | 8 |
| −9 | 1 | 11 | 414 | 386 | 20 |
| −7 | 1 | 11 | 329 | 312 | 17 |
| −5 | 1 | 11 | 102 | 89 | 6 |
| −3 | 1 | 11 | 131 | 140 | 6 |
| −1 | 1 | 11 | 95 | 92 | 6 |
| 1 | 1 | 11 | 31 | 41 | 18 |
| 3 | 1 | 11 | 107 | 106 | 6 |
| 5 | 1 | 11 | 76 | 77 | 7 |
| 7 | 1 | 11 | 0 | 13 | 1 |
| 9 | 1 | 11 | 78 | 72 | 6 |
| 11 | 1 | 11 | 125 | 107 | 7 |
| −24 | 2 | 11 | 109 | 87 | 9 |
| −22 | 2 | 11 | 65 | 58 | 14 |
| −12 | 2 | 11 | 38 | 52 | 29 |
| −10 | 2 | 11 | 160 | 172 | 12 |
| −8 | 2 | 11 | 228 | 246 | 13 |
| −6 | 2 | 11 | 133 | 130 | 7 |
| −4 | 2 | 11 | 272 | 288 | 8 |
| −2 | 2 | 11 | 170 | 174 | 7 |
| 0 | 2 | 11 | 86 | 74 | 11 |
| 2 | 2 | 11 | 94 | 96 | 10 |
| 4 | 2 | 11 | 288 | 298 | 15 |
| 6 | 2 | 11 | 44 | 24 | 11 |
| 8 | 2 | 11 | 131 | 131 | 12 |
| 10 | 2 | 11 | 30 | 25 | 22 |
| 12 | 2 | 11 | 29 | 13 | 28 |
| −7 | 3 | 11 | 166 | 160 | 12 |
| −5 | 3 | 11 | 264 | 280 | 15 |
| −3 | 3 | 11 | 245 | 235 | 13 |
| −1 | 3 | 11 | 248 | 227 | 12 |
| 1 | 3 | 11 | 144 | 113 | 10 |
| 3 | 3 | 11 | 39 | 40 | 17 |
| 5 | 3 | 11 | 137 | 147 | 16 |
| 7 | 3 | 11 | 108 | 91 | 12 |
| 9 | 3 | 11 | 72 | 55 | 9 |
| −2 | 4 | 11 | 135 | 122 | 9 |
| 0 | 4 | 11 | 209 | 190 | 11 |
| 2 | 4 | 11 | 65 | 58 | 12 |
| 4 | 4 | 11 | 113 | 102 | 8 |
| 6 | 4 | 11 | 44 | 32 | 16 |
| 8 | 4 | 11 | 63 | 47 | 7 |
| −17 | −5 | 12 | 26 | 39 | 26 |
| −15 | −5 | 12 | 65 | 39 | 11 |
| −13 | −5 | 12 | 43 | 48 | 11 |
| −11 | −5 | 12 | 113 | 99 | 8 |
| −9 | −5 | 12 | 74 | 70 | 7 |
| −7 | −5 | 12 | 122 | 116 | 5 |
| −5 | −5 | 12 | 56 | 58 | 12 |
| −3 | −5 | 12 | 91 | 79 | 9 |
| −1 | −5 | 12 | 89 | 81 | 9 |
| 1 | −5 | 12 | 54 | 45 | 11 |
| 3 | −5 | 12 | 42 | 49 | 14 |
| −20 | −4 | 12 | 0 | 17 | 1 |
| −18 | −4 | 12 | 154 | 134 | 9 |
| −16 | −4 | 12 | 48 | 43 | 9 |
| −14 | −4 | 12 | 202 | 200 | 13 |
| −12 | −4 | 12 | 115 | 144 | 9 |
| −10 | −4 | 12 | 122 | 136 | 13 |
| −8 | −4 | 12 | 33 | 43 | 15 |
| −6 | −4 | 12 | 23 | 36 | 22 |
| −4 | −4 | 12 | 54 | 66 | 16 |
| −2 | −4 | 12 | 49 | 58 | 17 |
| 0 | −4 | 12 | 93 | 88 | 10 |
| 2 | −4 | 12 | 82 | 84 | 10 |
| 4 | −4 | 12 | 50 | 48 | 14 |
| −23 | −3 | 12 | 28 | 30 | 21 |
| −10 | 2 | 14 | 98 | 82 | 9 |
| −8 | 2 | 14 | 341 | 341 | 11 |
| −6 | 2 | 14 | 206 | 194 | 8 |
| −4 | 2 | 14 | 366 | 382 | 12 |
| −2 | 2 | 14 | 101 | 141 | 8 |
| 0 | 2 | 14 | 122 | 128 | 6 |
| 2 | 2 | 14 | 44 | 51 | 10 |
| 4 | 2 | 14 | 73 | 71 | 8 |
| 6 | 2 | 14 | 0 | 14 | 1 |
| −11 | 3 | 14 | 279 | 267 | 14 |

TABLE 8-continued

Observed and calculated structure factors for 24F2-DM.

| h | k | l | 10Fc | 10Fc | 10s |
|---|---|---|------|------|-----|
| -9 | 3 | 14 | 198 | 174 | 11 |
| -7 | 3 | 14 | 105 | 109 | 9 |
| -5 | 3 | 14 | 266 | 251 | 13 |
| -3 | 3 | 14 | 233 | 223 | 8 |
| -1 | 3 | 14 | 40 | 49 | 15 |
| 1 | 3 | 14 | 71 | 66 | 15 |
| 3 | 3 | 14 | 47 | 37 | 11 |
| 5 | 3 | 14 | 0 | 25 | 1 |
| -6 | 4 | 14 | 92 | 104 | 10 |
| -4 | 4 | 14 | 82 | 88 | 10 |
| -2 | 4 | 14 | 115 | 117 | 9 |
| 0 | 4 | 14 | 74 | 67 | 9 |
| 2 | 4 | 14 | 36 | 32 | 14 |
| -15 | -5 | 15 | 105 | 94 | 7 |
| -13 | -5 | 15 | 66 | 62 | 5 |
| -11 | -5 | 15 | 173 | 149 | 6 |
| -9 | -5 | 15 | 5 | 13 | 5 |
| -7 | -5 | 15 | 25 | 35 | 24 |
| -5 | -5 | 15 | 54 | 52 | 11 |
| -20 | -4 | 15 | 36 | 36 | 20 |
| -18 | -4 | 15 | 0 | 22 | 1 |
| -16 | -4 | 15 | 68 | 48 | 7 |
| -14 | -4 | 15 | 108 | 100 | 8 |
| -12 | -4 | 15 | 0 | 10 | 1 |
| -10 | -4 | 15 | 114 | 114 | 6 |
| -8 | -4 | 15 | 151 | 143 | 10 |
| -6 | -4 | 15 | 95 | 92 | 10 |
| -4 | -4 | 15 | 65 | 42 | 12 |
| -2 | -4 | 15 | 0 | 5 | 1 |
| 0 | -4 | 15 | 46 | 48 | 15 |
| -23 | -3 | 15 | 41 | 29 | 10 |
| -21 | -3 | 15 | 108 | 99 | 5 |
| -19 | -3 | 15 | 69 | 83 | 6 |
| -17 | -3 | 15 | 189 | 182 | 10 |
| -15 | -3 | 15 | 274 | 264 | 8 |
| -13 | -3 | 15 | 168 | 155 | 7 |
| -11 | -3 | 15 | 299 | 273 | 10 |
| -9 | -3 | 15 | 119 | 115 | 14 |
| -7 | -3 | 15 | 135 | 128 | 23 |
| -5 | -3 | 15 | 66 | 78 | 6 |
| -3 | -3 | 15 | 32 | 28 | 15 |
| -24 | -2 | 15 | 102 | 96 | 6 |
| -22 | -2 | 15 | 15 | 12 | 14 |
| -20 | -2 | 15 | 198 | 215 | 6 |
| -18 | -2 | 15 | 58 | 56 | 8 |
| -16 | -2 | 15 | 184 | 181 | 11 |
| -14 | -2 | 15 | 211 | 190 | 6 |
| -12 | -2 | 15 | 137 | 133 | 4 |
| -10 | -2 | 15 | 114 | 122 | 4 |
| -8 | -2 | 15 | 130 | 126 | 8 |
| -6 | -2 | 15 | 252 | 272 | 11 |
| -4 | -2 | 15 | 177 | 194 | 9 |
| -2 | -2 | 15 | 173 | 188 | 8 |
| 0 | -2 | 15 | 117 | 127 | 6 |
| 2 | -2 | 15 | 57 | 61 | 7 |
| 4 | -2 | 15 | 54 | 39 | 6 |
| -25 | -1 | 15 | 44 | 33 | 11 |
| -23 | -1 | 15 | 46 | 48 | 11 |
| -21 | -1 | 15 | 104 | 210 | 5 |
| -19 | -1 | 15 | 12 | 17 | 12 |
| -17 | -1 | 15 | 142 | 149 | 11 |
| -15 | -1 | 15 | 152 | 158 | 11 |
| -13 | -1 | 15 | 143 | 128 | 15 |
| -11 | -1 | 15 | 384 | 355 | 10 |
| -9 | -1 | 15 | 267 | 242 | 7 |
| -7 | -1 | 15 | 338 | 316 | 9 |
| -5 | -1 | 15 | 130 | 120 | 6 |
| -3 | -1 | 15 | 208 | 197 | 9 |
| -1 | -1 | 15 | 60 | 57 | 8 |
| 1 | -1 | 15 | 164 | 164 | 9 |
| 3 | -1 | 15 | 45 | 51 | 9 |
| 5 | -1 | 15 | 45 | 37 | 10 |
| 7 | -1 | 15 | 64 | 47 | 6 |
| -26 | 0 | 15 | 111 | 88 | 6 |
| -24 | 0 | 15 | 104 | 93 | 7 |
| -22 | 0 | 15 | 66 | 66 | 10 |
| -20 | 0 | 15 | 46 | 53 | 11 |
| 2 | 0 | 18 | 78 | 81 | 6 |
| -21 | 1 | 18 | 102 | 108 | 20 |
| -19 | 1 | 18 | 6 | 17 | 5 |
| -17 | 1 | 18 | 101 | 125 | 7 |
| -15 | 1 | 18 | 134 | 135 | 16 |
| -13 | 1 | 18 | 173 | 204 | 8 |
| -11 | 1 | 18 | 151 | 160 | 8 |
| -9 | 1 | 18 | 82 | 87 | 8 |
| -7 | 1 | 18 | 132 | 139 | 11 |
| -5 | 1 | 18 | 58 | 67 | 12 |
| -3 | 1 | 18 | 47 | 36 | 11 |
| -1 | 1 | 18 | 68 | 61 | 10 |
| -20 | 2 | 18 | 40 | 42 | 29 |
| -18 | 2 | 18 | 0 | 23 | 1 |
| -16 | 2 | 18 | 34 | 45 | 99 |
| -14 | 2 | 18 | 97 | 104 | 7 |
| -12 | 2 | 18 | 66 | 67 | 25 |
| -10 | 2 | 18 | 87 | 96 | 7 |
| -8 | 2 | 18 | 39 | 46 | 16 |
| -6 | 2 | 18 | 131 | 136 | 15 |
| -4 | 2 | 18 | 46 | 43 | 13 |
| -2 | 2 | 18 | 81 | 76 | 6 |
| 0 | 2 | 18 | 61 | 50 | 6 |
| -17 | 3 | 18 | 44 | 46 | 22 |
| -15 | 3 | 18 | 119 | 122 | 10 |
| -13 | 3 | 18 | 15 | 27 | 15 |
| -11 | 3 | 18 | 158 | 138 | 10 |
| -9 | 3 | 18 | 79 | 78 | 8 |
| -7 | 3 | 18 | 81 | 86 | 7 |
| -5 | 3 | 18 | 21 | 27 | 21 |
| -3 | 3 | 18 | 47 | 44 | 9 |
| -12 | 4 | 18 | 79 | 79 | 10 |
| -10 | 4 | 18 | 40 | 50 | 24 |
| -8 | 4 | 18 | 32 | 31 | 32 |
| -19 | -3 | 19 | 29 | 37 | 28 |
| -17 | -3 | 19 | 85 | 83 | 5 |
| -15 | -3 | 19 | 32 | 44 | 17 |
| -13 | -3 | 19 | 16 | 24 | 16 |
| -11 | -3 | 19 | 28 | 27 | 27 |
| -9 | -3 | 19 | 125 | 105 | 6 |
| -7 | -2 | 19 | 64 | 66 | 5 |
| -22 | -2 | 19 | 24 | 37 | 24 |
| -20 | -2 | 19 | 41 | 49 | 10 |
| -18 | -2 | 19 | 77 | 64 | 11 |
| -16 | -2 | 19 | 44 | 48 | 27 |
| -14 | -2 | 19 | 56 | 43 | 11 |
| -12 | -2 | 19 | 37 | 20 | 19 |
| -10 | -2 | 19 | 60 | 63 | 9 |
| -8 | -2 | 19 | 57 | 61 | 9 |
| -6 | -2 | 19 | 48 | 52 | 10 |
| -4 | -2 | 19 | 92 | 76 | 6 |
| -2 | -2 | 19 | 62 | 64 | 5 |
| -23 | -1 | 19 | 132 | 114 | 5 |
| -21 | -1 | 19 | 51 | 38 | 8 |
| -19 | -1 | 19 | 138 | 123 | 7 |
| -17 | -1 | 19 | 105 | 104 | 15 |
| -15 | -1 | 19 | 0 | 27 | 1 |
| -13 | -1 | 19 | 62 | 58 | 6 |
| -11 | -1 | 19 | 56 | 68 | 7 |
| -9 | -1 | 19 | 133 | 117 | 8 |
| -7 | -1 | 19 | 15 | 24 | 15 |
| -5 | -1 | 19 | 71 | 57 | 8 |
| -3 | -1 | 19 | 42 | 34 | 12 |
| -1 | -1 | 19 | 114 | 101 | 6 |
| -24 | 0 | 19 | 124 | 100 | 14 |
| -22 | 0 | 19 | 186 | 164 | 11 |
| -20 | 0 | 19 | 55 | 62 | 10 |
| -18 | 0 | 19 | 64 | 63 | 8 |
| 14 | 2 | 1 | 62 | 68 | 14 |
| 16 | 2 | 1 | 104 | 110 | 11 |
| 18 | 2 | 1 | 41 | 51 | 26 |
| -19 | 3 | 1 | 100 | 61 | 19 |
| -17 | 3 | 1 | 54 | 63 | 21 |
| -15 | 3 | 1 | 0 | 41 | 1 |
| -13 | 3 | 1 | 0 | 34 | 1 |

TABLE 8-continued

Observed and calculated structure factors for 24F2-DM.

| h | k | l | 10Fc | 10Fc | 10s |
|---|---|---|------|------|-----|
| 9 | 3 | 1 | 255 | 271 | 14 |
| 11 | 3 | 1 | 50 | 54 | 22 |
| 13 | 3 | 1 | 134 | 128 | 9 |
| 15 | 3 | 1 | 161 | 157 | 10 |
| 17 | 3 | 1 | 64 | 71 | 17 |
|  | 4 | 1 | 60 | 19 | 12 |
| -3 | -7 | 2 | 61 | 59 | 3 |
| -1 | -7 | 2 | 80 | 75 | 3 |
| 1 | -7 | 2 | 85 | 86 | 5 |
| -10 | -6 | 2 | 73 | 74 | 5 |
| -8 | -6 | 2 | 49 | 54 | 6 |
| -6 | -6 | 2 | 63 | 56 | 10 |
| -4 | -6 | 2 | 14 | 8 | 14 |
| -2 | -6 | 2 | 90 | 100 | 10 |
| 0 | -6 | 2 | 56 | 64 | 12 |
| 2 | -6 | 2 | 128 | 133 | 5 |
| 4 | -6 | 2 | 174 | 172 | 8 |
| 6 | -6 | 2 | 140 | 131 | 9 |
| 8 | -6 | 2 | 55 | 63 | 11 |
| 10 | -6 | 2 | 0 | 39 | 1 |
| -17 | -5 | 2 | 10 | 12 | 10 |
| -15 | -5 | 2 | 11 | 12 | 11 |
| -13 | -5 | 2 | 117 | 115 | 18 |
| -11 | -5 | 2 | 70 | 82 | 13 |
| -9 | -5 | 2 | 51 | 52 | 10 |
| -7 | -5 | 2 | 96 | 114 | 6 |
| -5 | -5 | 2 | 96 | 107 | 4 |
| -3 | -5 | 2 | 188 | 158 | 9 |
| -1 | -5 | 2 | 301 | 293 | 11 |
| 1 | -5 | 2 | 416 | 410 | 10 |
| 3 | -5 | 2 | 174 | 167 | 4 |
| 5 | -5 | 2 | 252 | 248 | 6 |
| 7 | -5 | 2 | 32 | 15 | 32 |
| 9 | -5 | 2 | 63 | 74 | 11 |
| 11 | -5 | 2 | 0 | 19 | 1 |
| 13 | -5 | 2 | 0 | 21 | 1 |
| 15 | -5 | 2 | 56 | 47 | 11 |
| -20 | -4 | 2 | 40 | 22 | 9 |
| -18 | -4 | 2 | 63 | 65 | 6 |
| -16 | -4 | 2 | 104 | 119 | 5 |
| -14 | -4 | 2 | 119 | 149 | 7 |
| -12 | -4 | 2 | 156 | 178 | 7 |
| -10 | -4 | 2 | 254 | 249 | 8 |
| -8 | -4 | 2 | 54 | 61 | 6 |
| -6 | -4 | 2 | 373 | 359 | 7 |
| -4 | -4 | 2 | 51 | 47 | 7 |
| -2 | -4 | 2 | 281 | 271 | 6 |
| 0 | -4 | 2 | 151 | 135 | 5 |
| 2 | -4 | 2 | 183 | 173 | 4 |
| 4 | -4 | 2 | 153 | 142 | 5 |
| 6 | -4 | 2 | 12 | 7 | 11 |
| 8 | -4 | 2 | 59 | 60 | 5 |
| 10 | -4 | 2 | 149 | 160 | 5 |
| 12 | -4 | 2 | 174 | 162 | 7 |
| 14 | -4 | 2 | 128 | 119 | 10 |
| 16 | -4 | 2 | 32 | 37 | 32 |
| -21 | -3 | 2 | 22 | 33 | 21 |
| -19 | -3 | 2 | 175 | 161 | 7 |
| -17 | -3 | 2 | 59 | 60 | 13 |
| -15 | -3 | 2 | 139 | 161 | 9 |
| -13 | -3 | 2 | 129 | 125 | 5 |
| -11 | -3 | 2 | 128 | 109 | 5 |
| -9 | -3 | 2 | 123 | 119 | 4 |
| -7 | -3 | 2 | 194 | 164 | 11 |
| -5 | -3 | 2 | 581 | 537 | 30 |
| -3 | -3 | 2 | 394 | 441 | 20 |
| -1 | -3 | 2 | 435 | 392 | 22 |
| 1 | -3 | 2 | 279 | 288 | 15 |
| 3 | -3 | 2 | 797 | 694 | 41 |
| 5 | -3 | 2 | 328 | 309 | 18 |
| 7 | -3 | 2 | 150 | 141 | 6 |
| 9 | -3 | 2 | 173 | 166 | 7 |
| 11 | -3 | 2 | 76 | 78 | 6 |
| 13 | -3 | 2 | 22 | 31 | 22 |
| 15 | -3 | 2 | 61 | 65 | 14 |
| 17 | -3 | 2 | 35 | 25 | 12 |
| 19 | -3 | 2 | 44 | 34 | 6 |
| -22 | -2 | 2 | 42 | 43 | 13 |
| -20 | -2 | 2 | 42 | 34 | 15 |
| -18 | -2 | 2 | 88 | 90 | 8 |
| -5 | -3 | 4 | 522 | 507 | 21 |
| -3 | -3 | 4 | 259 | 276 | 14 |
| -1 | -3 | 4 | 158 | 143 | 11 |
| 1 | -3 | 4 | 184 | 159 | 12 |
| 3 | -3 | 4 | 202 | 201 | 9 |
| 5 | -3 | 4 | 178 | 174 | 8 |
| 7 | -3 | 4 | 301 | 285 | 15 |
| 9 | -3 | 4 | 242 | 240 | 8 |
| 11 | -3 | 4 | 52 | 56 | 7 |
| 13 | -3 | 4 | 35 | 17 | 10 |
| 15 | -3 | 4 | 104 | 98 | 6 |
| -24 | -2 | 4 | 19 | 23 | 18 |
| -22 | -2 | 4 | 29 | 31 | 28 |
| -20 | -2 | 4 | 229 | 215 | 8 |
| -18 | -2 | 4 | 298 | 273 | 8 |
| -16 | -2 | 4 | 175 | 177 | 6 |
| -14 | -2 | 4 | 162 | 172 | 5 |
| -12 | -2 | 4 | 210 | 209 | 1 |
| -10 | -2 | 4 | 112 | 124 | 10 |
| -8 | -2 | 4 | 61 | 56 | 11 |
| -6 | -2 | 4 | 414 | 453 | 21 |
| -4 | -2 | 4 | 104 | 120 | 9 |
| -2 | -2 | 4 | 260 | 262 | 9 |
| 0 | -2 | 4 | 212 | 196 | 12 |
| 2 | -2 | 4 | 230 | 219 | 13 |
| 4 | -2 | 4 | 593 | 539 | 30 |
| 8 | -2 | 4 | 107 | 98 | 7 |
| 10 | -2 | 4 | 34 | 42 | 14 |
| 12 | -2 | 4 | 72 | 65 | 7 |
| 14 | -2 | 4 | 100 | 118 | 6 |
| 16 | -2 | 4 | 0 | 15 | 1 |
| 18 | -2 | 4 | 66 | 63 | 6 |
| -21 | -1 | 4 | 69 | 53 | 12 |
| -19 | -1 | 4 | 237 | 210 | 11 |
| -17 | -1 | 4 | 125 | 123 | 5 |
| -15 | -1 | 4 | 176 | 185 | 5 |
| -13 | -1 | 4 | 461 | 465 | 22 |
| -11 | -1 | 4 | 147 | 146 | 11 |
| -9 | -1 | 4 | 184 | 192 | 12 |
| -7 | -1 | 4 | 287 | 317 | 17 |
| -5 | -1 | 4 | 181 | 185 | 10 |
| -3 | -1 | 4 | 676 | 659 | 23 |
| -1 | -1 | 4 | 694 | 679 | 25 |
| 1 | -1 | 4 | 454 | 408 | 24 |
| 3 | -1 | 4 | 527 | 521 | 18 |
| 5 | -1 | 4 | 226 | 222 | 11 |
| 7 | -1 | 4 | 237 | 240 | 13 |
| 9 | -1 | 4 | 71 | 76 | 5 |
| 11 | -1 | 4 | 145 | 148 | 6 |
| 13 | -1 | 4 | 236 | 217 | 11 |
| 15 | -1 | 4 | 216 | 184 | 10 |
| 17 | -1 | 4 | 228 | 129 | 8 |
| 19 | -1 | 4 | 163 | 147 | 8 |
| -24 | 0 | 4 | 153 | 123 | 10 |
| -22 | 0 | 4 | 157 | 127 | 11 |
| -20 | 0 | 4 | 0 | 17 | 1 |
| -18 | 0 | 4 | 171 | 162 | 12 |
| -16 | 0 | 4 | 5 | 21 | 5 |
| -14 | 0 | 4 | 0 | 34 | 1 |
| -12 | 0 | 4 | 64 | 55 | 18 |
| -10 | 0 | 4 | 194 | 179 | 12 |
| -6 | 0 | 4 | 241 | 221 | 13 |
| -4 | 0 | 4 | 145 | 118 | 6 |
| -2 | 0 | 4 | 298 | 297 | 13 |
| 0 | 0 | 4 | 698 | 710 | 25 |
| 2 | 0 | 4 | 358 | 394 | 28 |
| 4 | 0 | 4 | 318 | 377 | 16 |
| 6 | 0 | 4 | 324 | 382 | 17 |
| 8 | 0 | 4 | 130 | 127 | 10 |
| 10 | 0 | 4 | 257 | 263 | 7 |
| 12 | 0 | 4 | 172 | 175 | 6 |
| 14 | 0 | 4 | 101 | 101 | 8 |

TABLE 8-continued

Observed and calculated structure factors for 24F2-DM.

| h | k | l | 10Fc | 10Fc | 10s |
|---|---|---|------|------|-----|
| 16 | 0 | 4 | 148 | 121 | 9 |
| 18 | 0 | 4 | 196 | 176 | 9 |
| 20 | 0 | 4 | 47 | 56 | 10 |
| −25 | 1 | 4 | 77 | 78 | 9 |
| −23 | 1 | 4 | 61 | 42 | 14 |
| −21 | 1 | 4 | 48 | 53 | 20 |
| −19 | 1 | 4 | 209 | 210 | 14 |
| −17 | 1 | 4 | 129 | 124 | 20 |
| −15 | 1 | 4 | 176 | 134 | 8 |
| −13 | 1 | 4 | 428 | 456 | 24 |
| −11 | 1 | 4 | 170 | 146 | 10 |
| −9 | 1 | 4 | 213 | 192 | 11 |
| −7 | 1 | 4 | 323 | 318 | 16 |
| −5 | 1 | 4 | 178 | 185 | 7 |
| −3 | 1 | 4 | 650 | 663 | 35 |
| 1 | 1 | 6 | 486 | 463 | 25 |
| 3 | 1 | 6 | 491 | 520 | 25 |
| 5 | 1 | 6 | 180 | 160 | 10 |
| 7 | 1 | 6 | 164 | 160 | 10 |
| 9 | 1 | 6 | 178 | 183 | 13 |
| 13 | 1 | 6 | 147 | 149 | 10 |
| 15 | 1 | 6 | 42 | 43 | 12 |
| 17 | 1 | 6 | 46 | 16 | 13 |
| −24 | 2 | 6 | 7 | 18 | 7 |
| −22 | 2 | 6 | 61 | 60 | 17 |
| −20 | 2 | 6 | 126 | 108 | 10 |
| −18 | 2 | 6 | 70 | 64 | 16 |
| −16 | 2 | 6 | 0 | 61 | 1 |
| −4 | 2 | 6 | 529 | 501 | 26 |
| −2 | 2 | 6 | 428 | 366 | 22 |
| 0 | 2 | 6 | 313 | 269 | 16 |
| 2 | 2 | 6 | 296 | 259 | 16 |
| 4 | 2 | 6 | 164 | 161 | 12 |
| 6 | 2 | 6 | 89 | 80 | 14 |
| 8 | 2 | 6 | 103 | 120 | 15 |
| 12 | 2 | 6 | 0 | 23 | 1 |
| 14 | 2 | 6 | 50 | 52 | 14 |
| 16 | 2 | 6 | 30 | 36 | 30 |
| −23 | 3 | 6 | 84 | 92 | 11 |
| −21 | 3 | 6 | 129 | 118 | 10 |
| −19 | 3 | 6 | 57 | 33 | 19 |
| 3 | 3 | 6 | 131 | 126 | 10 |
| 5 | 3 | 6 | 253 | 270 | 13 |
| 7 | 3 | 6 | 168 | 180 | 12 |
| 9 | 3 | 6 | 114 | 114 | 10 |
| 11 | 3 | 6 | 10 | 51 | 10 |
| 13 | 3 | 6 | 13 | 26 | 13 |
| 15 | 3 | 6 | 0 | 8 | 1 |
| 6 | 4 | 6 | 144 | 150 | 11 |
| 8 | 4 | 6 | 0 | 12 | 1 |
| 10 | 4 | 6 | 0 | 19 | 1 |
| 10 | 4 | 6 | 29 | 22 | 28 |
| 14 | 4 | 6 | 9 | 12 | 9 |
| −14 | −6 | 7 | 42 | 59 | 10 |
| −12 | −6 | 7 | 20 | 7 | 20 |
| −10 | −6 | 7 | 58 | 61 | 6 |
| −8 | −6 | 7 | 59 | 67 | 13 |
| −6 | −6 | 7 | 83 | 76 | 11 |
| −4 | −6 | 7 | 154 | 141 | 7 |
| −2 | −6 | 7 | 43 | 47 | 14 |
| 0 | −6 | 7 | 42 | 26 | 14 |
| 2 | −6 | 7 | 36 | 38 | 19 |
| 4 | −6 | 7 | 45 | 41 | 13 |
| −17 | −5 | 7 | 80 | 94 | 5 |
| −15 | −5 | 7 | 81 | 85 | 6 |
| −13 | −5 | 7 | 66 | 70 | 7 |
| −11 | −5 | 7 | 180 | 163 | 6 |
| −9 | −5 | 7 | 0 | 16 | 1 |
| −7 | −5 | 7 | 78 | 80 | 5 |
| −5 | −5 | 7 | 44 | 53 | 7 |
| −3 | −5 | 7 | 52 | 47 | 15 |
| −1 | −5 | 7 | 26 | 46 | 26 |
| 1 | −5 | 7 | 73 | 82 | 9 |
| 3 | −5 | 7 | 74 | 97 | 9 |
| 5 | −5 | 7 | 71 | 96 | 10 |
| 7 | −5 | 7 | 19 | 35 | 18 |
| 9 | −5 | 7 | 33 | 39 | 32 |
| −22 | −4 | 7 | 111 | 104 | 5 |
| −20 | −4 | 7 | 24 | 24 | 23 |
| −18 | −4 | 7 | 72 | 84 | 6 |
| −16 | −4 | 7 | 67 | 59 | 7 |
| −14 | −4 | 7 | 210 | 216 | 11 |
| −12 | −4 | 7 | 169 | 159 | 5 |
| −10 | −4 | 7 | 205 | 192 | 4 |
| −8 | −4 | 7 | 93 | 96 | 5 |
| −6 | −4 | 7 | 185 | 178 | 6 |
| −4 | −4 | 7 | 197 | 189 | 6 |
| −2 | −4 | 7 | 190 | 183 | 9 |
| 0 | −4 | 7 | 186 | 191 | 12 |
| 2 | −4 | 7 | 222 | 221 | 17 |
| 4 | −4 | 7 | 174 | 187 | 11 |
| 6 | −4 | 7 | 106 | 94 | 10 |
| 8 | −4 | 7 | 100 | 101 | 10 |
| 10 | −4 | 7 | 58 | 68 | 15 |
| 12 | −4 | 7 | 37 | 4 | 29 |
| −23 | −3 | 7 | 50 | 44 | 8 |
| −21 | −3 | 7 | 161 | 150 | 6 |
| −19 | −3 | 7 | 231 | 222 | 11 |
| −17 | −3 | 7 | 194 | 195 | 6 |
| −15 | −3 | 7 | 465 | 447 | 10 |
| −13 | −3 | 7 | 210 | 225 | 5 |
| −11 | −3 | 7 | 102 | 101 | 3 |
| −16 | −2 | 9 | 78 | 85 | 6 |
| −14 | −2 | 9 | 70 | 72 | 6 |
| −12 | −2 | 9 | 158 | 160 | 5 |
| −10 | −2 | 9 | 141 | 139 | 4 |
| −8 | −2 | 9 | 143 | 142 | 11 |
| −6 | −2 | 9 | 457 | 429 | 24 |
| −4 | −2 | 9 | 451 | 452 | 24 |
| −2 | −2 | 9 | 210 | 222 | 9 |
| 0 | −2 | 9 | 64 | 60 | 5 |
| 2 | −2 | 9 | 162 | 166 | 7 |
| 4 | −2 | 9 | 136 | 145 | 7 |
| 6 | −2 | 9 | 555 | 517 | 21 |
| 8 | −2 | 9 | 215 | 235 | 9 |
| 10 | −2 | 9 | 134 | 140 | 6 |
| 12 | −2 | 9 | 60 | 61 | 6 |
| −25 | −1 | 9 | 118 | 108 | 9 |
| −23 | −1 | 9 | 130 | 122 | 26 |
| −21 | −1 | 9 | 191 | 179 | 17 |
| −19 | −1 | 9 | 251 | 243 | 9 |
| −17 | −1 | 9 | 92 | 87 | 11 |
| −15 | −1 | 9 | 205 | 206 | 6 |
| −13 | −1 | 9 | 251 | 270 | 7 |
| −11 | −1 | 9 | 423 | 395 | 22 |
| −9 | −1 | 9 | 442 | 401 | 24 |
| −7 | −1 | 9 | 322 | 303 | 18 |
| −5 | −1 | 9 | 445 | 414 | 21 |
| −3 | −1 | 9 | 474 | 459 | 28 |
| −1 | −1 | 9 | 85 | 90 | 10 |
| 1 | −1 | 9 | 347 | 342 | 11 |
| 3 | −1 | 9 | 188 | 196 | 6 |
| 5 | −1 | 9 | 159 | 168 | 8 |
| 7 | −1 | 9 | 91 | 83 | 6 |
| 9 | −1 | 9 | 46 | 63 | 10 |
| 11 | −1 | 9 | 63 | 77 | 7 |
| 13 | −1 | 9 | 42 | 44 | 10 |
| 15 | −1 | 9 | 0 | 16 | 1 |
| −26 | 0 | 9 | 3 | 29 | 3 |
| −24 | 0 | 9 | 0 | 13 | 1 |
| −22 | 0 | 9 | 41 | 69 | 25 |
| −20 | 0 | 9 | 125 | 141 | 10 |
| −18 | 0 | 9 | 54 | 58 | 13 |
| −16 | 0 | 9 | 388 | 370 | 13 |
| −14 | 0 | 9 | 308 | 276 | 17 |
| −12 | 0 | 9 | 527 | 542 | 27 |
| −10 | 0 | 9 | 356 | 376 | 19 |
| −8 | 0 | 9 | 937 | 380 | 48 |
| −6 | 0 | 9 | 348 | 375 | 18 |
| −4 | 0 | 9 | 0 | 21 | 1 |
| −2 | 0 | 9 | 115 | 141 | 9 |
| 0 | 0 | 9 | 176 | 201 | 11 |

TABLE 8-continued

Observed and calculated structure factors for 24F2-DM.

| h | k | l | 10Fc | 10Fc | 10s |
|---|---|---|---|---|---|
| 2 | 0 | 9 | 360 | 363 | 12 |
| 4 | 0 | 9 | 89 | 84 | 4 |
| 6 | 0 | 9 | 230 | 235 | 6 |
| 8 | 0 | 9 | 0 | 13 | 1 |
| 10 | 0 | 9 | 87 | 92 | 5 |
| 12 | 0 | 9 | 73 | 75 | 7 |
| 14 | 0 | 9 | 40 | 38 | 12 |
| −27 | 1 | 9 | 45 | 37 | 17 |
| −25 | 1 | 9 | 118 | 108 | 10 |
| −23 | 1 | 9 | 132 | 121 | 10 |
| −21 | 1 | 9 | 197 | 178 | 12 |
| −19 | 1 | 9 | 259 | 244 | 14 |
| −17 | 1 | 9 | 78 | 89 | 13 |
| −15 | 1 | 9 | 193 | 205 | 13 |
| −11 | 1 | 9 | 415 | 395 | 22 |
| −9 | 1 | 9 | 458 | 401 | 23 |
| −7 | 1 | 9 | 352 | 303 | 17 |
| −5 | 1 | 9 | 404 | 414 | 23 |
| −3 | 1 | 9 | 550 | 460 | 24 |
| −1 | 1 | 9 | 100 | 90 | 12 |
| 1 | 1 | 9 | 363 | 341 | 12 |
| 3 | 1 | 9 | 194 | 197 | 6 |
| 5 | 1 | 9 | 162 | 169 | 6 |
| 7 | 1 | 9 | 96 | 94 | 6 |
| 9 | 1 | 9 | 67 | 63 | 10 |
| 11 | 1 | 9 | 88 | 77 | 12 |
| 13 | 1 | 9 | 43 | 43 | 16 |
| −26 | 2 | 9 | 49 | 30 | 16 |
| −24 | 2 | 9 | 56 | 50 | 17 |
| −22 | 2 | 9 | 0 | 30 | 1 |
| −20 | 2 | 9 | 227 | 225 | 13 |
| −6 | 2 | 9 | 455 | 429 | 24 |
| −4 | 2 | 9 | 462 | 453 | 24 |
| −2 | 2 | 9 | 236 | 220 | 12 |
| 0 | 2 | 9 | 80 | 61 | 9 |
| 2 | 2 | 9 | 160 | 167 | 6 |
| 4 | 2 | 9 | 147 | 146 | 5 |
| −21 | −3 | 12 | 99 | 93 | 5 |
| −19 | −3 | 12 | 95 | 112 | 5 |
| −17 | −3 | 12 | 53 | 61 | 6 |
| −15 | −3 | 12 | 0 | 12 | 1 |
| −13 | −3 | 12 | 113 | 114 | 5 |
| −11 | −3 | 12 | 33 | 36 | 12 |
| −9 | −3 | 12 | 158 | 150 | 9 |
| −7 | −3 | 12 | 190 | 172 | 9 |
| −5 | −3 | 12 | 61 | 51 | 7 |
| −3 | −3 | 12 | 153 | 142 | 6 |
| −1 | −3 | 12 | 105 | 96 | 5 |
| 1 | −3 | 12 | 148 | 143 | 11 |
| −26 | −2 | 12 | 64 | 45 | 11 |
| −24 | −2 | 12 | 37 | 34 | 14 |
| −22 | −2 | 12 | 35 | 41 | 15 |
| −20 | −2 | 12 | 57 | 78 | 9 |
| −18 | −2 | 12 | 143 | 182 | 11 |
| −16 | −2 | 12 | 225 | 218 | 7 |
| −14 | −2 | 12 | 263 | 256 | 8 |
| −12 | −2 | 12 | 98 | 109 | 4 |
| −10 | −2 | 12 | 70 | 59 | 5 |
| −8 | −2 | 12 | 131 | 135 | 4 |
| −6 | −2 | 12 | 238 | 238 | 6 |
| −4 | −2 | 12 | 220 | 243 | 14 |
| −2 | −2 | 12 | 140 | 134 | 7 |
| 0 | −2 | 12 | 76 | 71 | 6 |
| 2 | −2 | 12 | 277 | 294 | 11 |
| 4 | −2 | 12 | 103 | 112 | 7 |
| 6 | −2 | 12 | 202 | 209 | 8 |
| 8 | −2 | 12 | 99 | 87 | 6 |
| −25 | −1 | 12 | 50 | 40 | 12 |
| −23 | −1 | 12 | 112 | 98 | 17 |
| −21 | −1 | 12 | 138 | 159 | 16 |
| −19 | −1 | 12 | 133 | 123 | 15 |
| −17 | −1 | 12 | 95 | 101 | 5 |
| −15 | −1 | 12 | 69 | 76 | 8 |
| −13 | −1 | 12 | 340 | 351 | 9 |
| −11 | −1 | 12 | 178 | 197 | 5 |
| −9 | −1 | 12 | 164 | 172 | 5 |
| −7 | −1 | 12 | 191 | 218 | 6 |
| −5 | −1 | 12 | 62 | 64 | 6 |
| −3 | −1 | 12 | 249 | 240 | 7 |
| −1 | −1 | 12 | 199 | 193 | 6 |
| 1 | −1 | 12 | 151 | 146 | 7 |
| 3 | −1 | 12 | 117 | 105 | 7 |
| 5 | −1 | 12 | 62 | 75 | 7 |
| 7 | −1 | 12 | 74 | 79 | 7 |
| 9 | −1 | 12 | 51 | 54 | 9 |
| 11 | −1 | 12 | 31 | 35 | 13 |
| −26 | 0 | 12 | 41 | 31 | 28 |
| −24 | 0 | 12 | 127 | 191 | 10 |
| −22 | 0 | 12 | 62 | 67 | 23 |
| −20 | 0 | 12 | 174 | 152 | 9 |
| −18 | 0 | 12 | 0 | 20 | 1 |
| −16 | 0 | 12 | 138 | 148 | 6 |
| −14 | 0 | 12 | 12 | 8 | 11 |
| −12 | 0 | 12 | 92 | 108 | 6 |
| −10 | 0 | 12 | 28 | 29 | 27 |
| −8 | 0 | 12 | 176 | 193 | 7 |
| −6 | 0 | 12 | 280 | 290 | 8 |
| −4 | 0 | 12 | 109 | 115 | 3 |
| −2 | 0 | 12 | 24 | 4 | 20 |
| 0 | 0 | 12 | 269 | 271 | 7 |
| 2 | 0 | 12 | 0 | 14 | 1 |
| 4 | 0 | 12 | 51 | 61 | 6 |
| 6 | 0 | 12 | 76 | 70 | 5 |
| 8 | 0 | 12 | 0 | 23 | 1 |
| 10 | 0 | 12 | 155 | 143 | 8 |
| 12 | 0 | 12 | 36 | 39 | 11 |
| −27 | 1 | 12 | 45 | 41 | 18 |
| −25 | 1 | 12 | 53 | 39 | 18 |
| −23 | 1 | 12 | 98 | 98 | 11 |
| −21 | 1 | 12 | 122 | 123 | 6 |
| −19 | 1 | 12 | 95 | 100 | 10 |
| −17 | 1 | 12 | 73 | 77 | 12 |
| −15 | 1 | 12 | 330 | 351 | 17 |
| −11 | 1 | 12 | 184 | 198 | 7 |
| −9 | 1 | 12 | 173 | 171 | 6 |
| −7 | 1 | 12 | 196 | 217 | 6 |
| −5 | 1 | 12 | 58 | 65 | 8 |
| −3 | 1 | 12 | 236 | 239 | 7 |
| −1 | 1 | 12 | 182 | 192 | 7 |
| 1 | 1 | 12 | 142 | 145 | 8 |
| 3 | 1 | 12 | 111 | 106 | 9 |
| 5 | 1 | 12 | 72 | 75 | 7 |
| 7 | 1 | 12 | 80 | 79 | 8 |
| 9 | 1 | 12 | 41 | 54 | 16 |
| −18 | 0 | 15 | 0 | 19 | 1 |
| −16 | 0 | 15 | 75 | 77 | 9 |
| −14 | 0 | 15 | 252 | 244 | 9 |
| −12 | 0 | 15 | 68 | 41 | 8 |
| −10 | 0 | 15 | 52 | 39 | 18 |
| −8 | 0 | 15 | 278 | 270 | 10 |
| −6 | 0 | 15 | 309 | 278 | 8 |
| −4 | 0 | 15 | 122 | 129 | 4 |
| −2 | 0 | 15 | 99 | 106 | 6 |
| 0 | 0 | 15 | 39 | 36 | 16 |
| 2 | 0 | 15 | 146 | 144 | 8 |
| 4 | 0 | 15 | 19 | 10 | 19 |
| 6 | 0 | 15 | 52 | 43 | 9 |
| −25 | 1 | 15 | 33 | 33 | 33 |
| −23 | 1 | 15 | 63 | 48 | 13 |
| −21 | 1 | 15 | 110 | 111 | 9 |
| −19 | 1 | 15 | 0 | 16 | 1 |
| −17 | 1 | 15 | 139 | 149 | 9 |
| −15 | 1 | 15 | 167 | 158 | 16 |
| −13 | 1 | 15 | 122 | 129 | 7 |
| −11 | 1 | 15 | 376 | 357 | 13 |
| −9 | 1 | 15 | 261 | 241 | 10 |
| −7 | 1 | 15 | 335 | 315 | 11 |
| −5 | 1 | 15 | 116 | 121 | 6 |
| −3 | 1 | 15 | 187 | 199 | 8 |
| −1 | 1 | 15 | 53 | 56 | 9 |
| 1 | 1 | 15 | 183 | 163 | 9 |
| 3 | 1 | 15 | 47 | 51 | 20 |

TABLE 8-continued

Observed and calculated structure factors for 24F2-DM.

| h | k | l | 10Fo | 10Fc | 10s |
|---|---|---|---|---|---|
| −18 | 2 | 15 | 45 | 56 | 24 |
| −16 | 2 | 15 | 185 | 181 | 12 |
| −14 | 2 | 15 | 206 | 189 | 13 |
| −12 | 2 | 15 | 131 | 132 | 10 |
| −10 | 2 | 15 | 121 | 122 | 7 |
| −8 | 2 | 15 | 124 | 125 | 7 |
| −6 | 2 | 15 | 265 | 273 | 13 |
| −4 | 2 | 15 | 189 | 195 | 18 |
| −2 | 2 | 15 | 177 | 188 | 11 |
| 0 | 2 | 15 | 118 | 126 | 14 |
| 2 | 2 | 15 | 60 | 61 | 7 |
| 4 | 2 | 15 | 51 | 39 | 8 |
| 6 | 2 | 15 | 59 | 56 | 9 |
| −13 | 3 | 15 | 151 | 155 | 13 |
| −11 | 3 | 15 | 301 | 272 | 15 |
| −9 | 3 | 15 | 133 | 116 | 9 |
| −7 | 3 | 15 | 131 | 127 | 9 |
| −5 | 3 | 15 | 71 | 78 | 8 |
| −3 | 3 | 15 | 36 | 28 | 17 |
| −1 | 3 | 15 | 70 | 79 | 15 |
| 1 | 3 | 15 | 105 | 96 | 6 |
| 3 | 3 | 15 | 27 | 16 | 21 |
| −8 | 4 | 15 | 140 | 143 | 9 |
| −6 | 4 | 15 | 94 | 92 | 9 |
| −4 | 4 | 15 | 54 | 42 | 13 |
| −2 | 4 | 15 | 0 | 6 | 1 |
| 0 | 4 | 15 | 53 | 48 | 9 |
| −11 | −5 | 16 | 100 | 98 | 7 |
| −18 | −4 | 16 | 103 | 94 | 9 |
| −16 | −4 | 16 | 77 | 66 | 6 |
| −14 | −4 | 16 | 196 | 164 | 7 |
| −12 | −4 | 16 | 64 | 61 | 7 |
| −10 | −4 | 16 | 32 | 27 | 14 |
| −8 | −4 | 16 | 19 | 25 | 19 |
| −6 | −4 | 16 | 16 | 22 | 16 |
| −4 | −4 | 16 | 17 | 30 | 17 |
| −2 | −4 | 16 | 38 | 59 | 21 |
| −23 | −3 | 16 | 41 | 36 | 12 |
| −21 | −3 | 16 | 21 | 17 | 21 |
| −19 | −3 | 16 | 0 | 16 | 1 |
| −17 | −3 | 16 | 39 | 48 | 10 |
| −15 | −3 | 16 | 40 | 51 | 13 |
| −13 | −3 | 16 | 173 | 174 | 16 |
| −11 | −3 | 16 | 48 | 41 | 10 |
| −9 | −3 | 16 | 65 | 68 | 7 |
| −7 | −3 | 16 | 72 | 83 | 6 |
| −5 | −3 | 16 | 116 | 117 | 5 |
| −24 | −2 | 16 | 47 | 44 | 9 |
| −22 | −2 | 16 | 29 | 46 | 28 |
| −20 | −2 | 16 | 31 | 36 | 20 |
| −18 | −2 | 16 | 85 | 95 | 8 |
| −16 | −2 | 16 | 206 | 188 | 8 |
| −14 | −2 | 16 | 202 | 188 | 6 |
| −12 | −2 | 16 | 221 | 194 | 6 |
| −10 | −2 | 16 | 347 | 339 | 10 |
| −8 | −2 | 16 | 77 | 78 | 7 |
| −6 | −2 | 16 | 88 | 98 | 7 |
| −4 | −2 | 16 | 15 | 20 | 14 |
| −2 | −2 | 16 | 56 | 63 | 8 |
| −16 | 0 | 19 | 22 | 24 | 22 |
| −14 | 0 | 19 | 12 | 10 | 11 |
| −12 | 0 | 19 | 58 | 68 | 9 |
| −10 | 0 | 19 | 16 | 39 | 15 |
| −8 | 0 | 19 | 143 | 138 | 6 |
| −6 | 0 | 19 | 69 | 61 | 9 |
| −4 | 0 | 19 | 19 | 24 | 19 |
| −2 | 0 | 19 | 38 | 37 | 13 |
| 0 | 0 | 19 | 94 | 76 | 6 |
| −23 | 1 | 19 | 133 | 114 | 9 |
| −21 | 1 | 19 | 45 | 38 | 19 |
| −19 | 1 | 19 | 118 | 122 | 8 |
| −17 | 1 | 19 | 92 | 104 | 14 |
| −15 | 1 | 19 | 38 | 27 | 16 |
| −13 | 1 | 19 | 31 | 58 | 27 |
| −11 | 1 | 19 | 48 | 68 | 12 |
| −9 | 1 | 19 | 114 | 118 | 9 |
| −7 | 1 | 19 | 0 | 23 | 1 |
| −5 | 1 | 19 | 63 | 57 | 8 |
| −3 | 1 | 19 | 33 | 35 | 33 |
| −22 | 2 | 19 | 56 | 37 | 13 |
| −20 | 2 | 19 | 36 | 49 | 36 |
| −18 | 2 | 19 | 78 | 64 | 11 |
| −16 | 2 | 19 | 31 | 48 | 31 |
| −14 | 2 | 19 | 40 | 44 | 19 |
| −12 | 2 | 19 | 0 | 20 | 1 |
| −10 | 2 | 19 | 62 | 63 | 9 |
| −8 | 2 | 19 | 60 | 61 | 9 |
| −6 | 2 | 19 | 39 | 52 | 14 |
| −4 | 2 | 19 | 85 | 76 | 10 |
| −2 | 2 | 19 | 67 | 64 | 10 |
| −17 | 3 | 19 | 79 | 84 | 10 |
| −15 | 3 | 19 | 51 | 45 | 17 |
| −13 | 3 | 19 | 0 | 24 | 1 |
| −11 | 3 | 19 | 25 | 27 | 24 |
| −9 | 3 | 19 | 113 | 105 | 6 |
| −7 | 3 | 19 | 75 | 66 | 7 |
| −5 | 3 | 19 | 53 | 53 | 8 |
| −15 | −3 | 20 | 30 | 17 | 30 |
| −13 | −3 | 20 | 92 | 84 | 6 |
| −11 | −3 | 20 | 0 | 5 | 1 |
| −9 | −3 | 20 | 31 | 30 | 11 |
| −20 | −2 | 20 | 59 | 60 | 7 |
| −18 | −2 | 20 | 16 | 43 | 16 |
| −16 | −2 | 20 | 59 | 39 | 9 |
| −14 | −2 | 20 | 59 | 54 | 10 |
| −12 | −2 | 20 | 0 | 8 | 1 |
| −10 | −2 | 20 | 62 | 49 | 9 |
| −8 | −2 | 20 | 59 | 55 | 8 |
| −6 | −2 | 20 | 22 | 16 | 22 |
| −23 | −1 | 20 | 10 | 29 | 9 |
| −21 | −1 | 20 | 66 | 47 | 7 |
| −19 | −1 | 20 | 47 | 27 | 20 |
| −17 | −1 | 20 | 0 | 14 | 1 |
| −15 | −1 | 20 | 80 | 78 | 6 |
| −13 | −1 | 20 | 47 | 56 | 9 |
| −11 | −1 | 20 | 62 | 70 | 10 |
| −9 | −1 | 20 | 91 | 89 | 7 |
| −7 | −1 | 20 | 119 | 108 | 7 |
| −5 | −1 | 20 | 53 | 34 | 9 |
| −3 | −1 | 20 | 74 | 74 | 6 |
| −22 | 0 | 20 | 34 | 27 | 17 |
| −20 | 0 | 20 | 143 | 124 | 7 |
| −18 | 0 | 20 | 27 | 39 | 26 |
| −16 | 0 | 20 | 48 | 46 | 11 |
| −14 | 0 | 20 | 29 | 31 | 28 |
| −12 | 0 | 20 | 171 | 156 | 8 |
| −10 | 0 | 20 | 171 | 143 | 7 |
| −16 | −2 | 2 | 0 | 32 | 1 |
| −14 | −2 | 2 | 233 | 232 | 6 |
| −12 | −2 | 2 | 417 | 450 | 9 |
| −10 | −2 | 2 | 873 | 787 | 45 |
| −8 | −2 | 2 | 97 | 113 | 9 |
| −6 | −2 | 2 | 690 | 741 | 38 |
| −4 | −2 | 2 | 151 | 161 | 12 |
| −2 | −2 | 2 | 184 | 215 | 12 |
| 0 | −2 | 2 | 494 | 462 | 14 |
| 2 | −2 | 2 | 488 | 531 | 30 |
| 10 | −2 | 2 | 137 | 128 | 5 |
| 12 | −2 | 2 | 218 | 213 | 10 |
| 14 | −2 | 2 | 83 | 96 | 7 |
| 16 | −2 | 2 | 87 | 108 | 7 |
| 18 | −2 | 2 | 155 | 147 | 8 |
| 20 | −2 | 2 | 31 | 49 | 15 |
| −23 | −1 | 2 | 79 | 62 | 7 |
| −21 | −1 | 2 | 28 | 35 | 27 |
| −19 | −1 | 2 | 111 | 113 | 6 |
| −17 | −1 | 2 | 69 | 63 | 9 |
| −15 | −1 | 2 | 121 | 117 | 5 |
| −13 | −1 | 2 | 172 | 172 | 7 |
| −11 | −1 | 2 | 375 | 405 | 22 |
| −9 | −1 | 2 | 203 | 198 | 12 |
| −7 | −1 | 2 | 933 | 965 | 48 |

TABLE 8-continued

Observed and calculated structure factors for 24F2-DM.

| h | k | l | 10Fc | 10Fc | 10s |
|---|---|---|------|------|-----|
| -5 | -1 | 2 | 697 | 678 | 25 |
| -3 | -1 | 2 | 422 | 411 | 14 |
| -1 | -1 | 2 | 666 | 618 | 23 |
| 3 | -1 | 2 | 44 | 56 | 5 |
| 5 | -1 | 2 | 373 | 413 | 20 |
| 7 | -1 | 2 | 173 | 197 | 10 |
| 9 | -1 | 2 | 328 | 317 | 17 |
| 11 | -1 | 2 | 235 | 244 | 6 |
| 13 | -1 | 2 | 155 | 154 | 6 |
| 15 | -1 | 2 | 110 | 111 | 7 |
| 17 | -1 | 2 | 107 | 94 | 8 |
| 19 | -1 | 2 | 50 | 56 | 11 |
| 21 | -1 | 2 | 114 | 100 | 7 |
| -22 | 0 | 2 | 36 | 38 | 35 |
| -20 | 0 | 2 | 78 | 80 | 11 |
| -18 | 0 | 2 | 92 | 105 | 11 |
| -16 | 0 | 2 | 0 | 4 | 1 |
| -14 | 0 | 2 | 152 | 146 | 8 |
| -12 | 0 | 2 | 118 | 127 | 11 |
| -10 | 0 | 2 | 434 | 460 | 22 |
| -8 | 0 | 2 | 831 | 815 | 42 |
| -6 | 0 | 2 | 32 | 40 | 32 |
| -4 | 0 | 2 | 909 | 875 | 46 |
| -2 | 0 | 2 | 99 | 107 | 4 |
| 0 | 0 | 2 | 265 | 250 | 7 |
| 2 | 0 | 2 | 354 | 339 | 18 |
| 4 | 0 | 2 | 437 | 497 | 22 |
| 6 | 0 | 2 | 116 | 136 | 3 |
| 8 | 0 | 2 | 196 | 274 | 11 |
| 10 | 0 | 2 | 57 | 52 | 15 |
| 12 | 0 | 2 | 134 | 145 | 5 |
| 14 | 0 | 2 | 78 | 74 | 7 |
| 16 | 0 | 2 | 43 | 63 | 13 |
| 18 | 0 | 2 | 38 | 41 | 22 |
| -23 | 1 | 2 | 44 | 62 | 14 |
| -21 | 1 | 2 | 50 | 35 | 16 |
| -19 | 1 | 2 | 95 | 113 | 11 |
| -17 | 1 | 2 | 64 | 63 | 17 |
| -15 | 1 | 2 | 122 | 116 | 9 |
| -13 | 1 | 2 | 167 | 171 | 7 |
| -11 | 1 | 2 | 417 | 405 | 20 |
| -9 | 1 | 2 | 224 | 198 | 11 |
| -7 | 1 | 2 | 941 | 964 | 48 |
| -5 | 1 | 2 | 713 | 680 | 25 |
| -3 | 1 | 2 | 401 | 410 | 15 |
| -1 | 1 | 2 | 628 | 621 | 35 |
| 1 | 1 | 2 | 1352 | 1283 | 69 |
| 3 | 1 | 2 | 45 | 52 | 13 |
| 5 | 1 | 2 | 392 | 413 | 19 |
| 7 | 1 | 2 | 183 | 195 | 10 |
| 9 | 1 | 2 | 333 | 319 | 17 |
| 11 | 1 | 2 | 239 | 244 | 9 |
| 13 | 1 | 2 | 155 | 153 | 8 |
| 15 | 1 | 2 | 89 | 111 | 10 |
| 17 | 1 | 2 | 94 | 93 | 10 |
| -22 | 2 | 2 | 44 | 43 | 23 |
| -20 | 2 | 2 | 27 | 33 | 27 |
| -18 | 2 | 2 | 57 | 90 | 20 |
| -16 | 2 | 2 | 0 | 32 | 1 |
| -14 | 2 | 2 | 237 | 232 | 13 |
| -12 | 2 | 2 | 394 | 428 | 21 |
| -8 | 2 | 2 | 129 | 115 | 9 |
| -1 | 1 | 4 | 720 | 680 | 35 |
| 1 | 1 | 4 | 467 | 409 | 23 |
| 3 | 1 | 4 | 480 | 520 | 28 |
| 5 | 1 | 4 | 218 | 222 | 13 |
| 7 | 1 | 4 | 239 | 241 | 13 |
| 9 | 1 | 4 | 74 | 76 | 8 |
| 11 | 1 | 4 | 148 | 148 | 7 |
| 13 | 1 | 4 | 236 | 216 | 12 |
| 15 | 1 | 4 | 181 | 146 | 6 |
| -24 | 2 | 4 | 30 | 23 | 29 |
| -22 | 2 | 4 | 0 | 31 | 1 |
| -20 | 2 | 4 | 229 | 215 | 13 |
| -18 | 2 | 4 | 299 | 273 | 15 |
| -16 | 2 | 4 | 167 | 178 | 11 |
| -14 | 2 | 4 | 153 | 171 | 10 |
| -4 | 2 | 4 | 130 | 119 | 8 |
| -2 | 2 | 4 | 263 | 261 | 14 |
| 0 | 2 | 4 | 213 | 193 | 12 |
| 2 | 2 | 4 | 231 | 220 | 13 |
| 4 | 2 | 4 | 587 | 541 | 30 |
| 6 | 2 | 4 | 310 | 288 | 17 |
| 8 | 2 | 4 | 116 | 99 | 6 |
| 10 | 2 | 4 | 50 | 42 | 15 |
| 12 | 2 | 4 | 88 | 85 | 11 |
| 18 | 2 | 4 | 66 | 64 | 11 |
| -23 | 3 | 4 | 30 | 34 | 29 |
| -21 | 3 | 4 | 44 | 59 | 29 |
| -19 | 3 | 4 | 41 | 22 | 41 |
| -17 | 3 | 4 | 153 | 169 | 11 |
| 15 | 3 | 4 | 86 | 97 | 12 |
| 17 | 3 | 4 | 46 | 52 | 19 |
| 10 | 4 | 4 | 84 | 95 | 11 |
| 12 | 4 | 4 | 22 | 30 | 21 |
| 14 | 4 | 4 | 34 | 14 | 34 |
| 16 | 4 | 4 | 31 | 11 | 31 |
| -14 | -6 | 5 | 11 | 27 | 10 |
| -12 | -6 | 5 | 74 | 75 | 11 |
| -10 | -6 | 5 | 30 | 18 | 13 |
| -8 | -6 | 5 | 105 | 99 | 5 |
| -6 | -6 | 5 | 38 | 36 | 9 |
| -4 | -6 | 5 | 134 | 160 | 7 |
| -2 | -6 | 5 | 117 | 110 | 4 |
| 0 | -6 | 5 | 32 | 27 | 22 |
| 2 | -6 | 5 | 71 | 59 | 9 |
| 4 | -6 | 5 | 92 | 84 | 8 |
| 6 | -6 | 5 | 64 | 54 | 9 |
| -17 | -6 | 5 | 14 | 8 | 13 |
| -15 | -5 | 5 | 0 | 25 | 1 |
| -13 | -5 | 5 | 66 | 67 | 7 |
| -11 | -5 | 5 | 160 | 156 | 5 |
| -9 | -5 | 5 | 266 | 255 | 8 |
| -7 | -5 | 5 | 279 | 256 | 8 |
| -5 | -5 | 5 | 190 | 189 | 5 |
| -3 | -5 | 5 | 123 | 125 | 5 |
| -1 | -5 | 5 | 77 | 78 | 5 |
| 1 | -5 | 5 | 166 | 163 | 10 |
| 3 | -5 | 5 | 61 | 64 | 11 |
| 5 | -5 | 5 | 30 | 40 | 30 |
| 7 | -5 | 5 | 92 | 97 | 9 |
| 9 | -5 | 5 | 60 | 45 | 13 |
| 11 | -5 | 5 | 24 | 28 | 23 |
| -20 | -4 | 5 | 28 | 13 | 20 |
| -18 | -4 | 5 | 20 | 21 | 20 |
| -16 | -4 | 5 | 54 | 65 | 9 |
| -14 | -4 | 5 | 218 | 247 | 6 |
| -12 | -4 | 5 | 182 | 10 | 6 |
| -10 | -4 | 5 | 219 | 206 | 6 |
| -8 | -4 | 5 | 113 | 103 | 3 |
| -6 | -4 | 5 | 127 | 113 | 5 |
| -4 | -4 | 5 | 178 | 181 | 5 |
| -2 | -4 | 5 | 116 | 107 | 4 |
| 0 | -4 | 5 | 125 | 102 | 5 |
| 2 | -4 | 5 | 112 | 103 | 19 |
| 4 | -4 | 5 | 57 | 66 | 12 |
| 6 | -4 | 5 | 157 | 157 | 11 |
| 8 | -4 | 5 | 71 | 80 | 12 |
| 10 | -4 | 5 | 43 | 47 | 24 |
| 12 | -4 | 5 | 54 | 42 | 17 |
| 14 | -4 | 5 | 29 | 24 | 23 |
| -23 | -3 | 5 | 51 | 50 | 7 |
| -21 | -3 | 5 | 57 | 65 | 8 |
| -19 | -3 | 5 | 190 | 191 | 8 |
| -17 | -3 | 5 | 206 | 193 | 6 |
| -15 | -3 | 5 | 38 | 39 | 11 |
| -13 | -3 | 5 | 196 | 206 | 6 |
| -11 | -3 | 5 | 118 | 119 | 4 |
| -9 | -3 | 5 | 246 | 250 | 5 |
| -9 | -3 | 7 | 313 | 303 | 6 |
| -7 | -3 | 7 | 92 | 80 | 3 |
| -5 | -3 | 7 | 255 | 251 | 7 |

TABLE 8-continued

Observed and calculated structure factors for 24F2-DM.

| h | k | l | 10Fo | 10Fc | 10s |
|---|---|---|------|------|-----|
| −3 | −3 | 7 | 201 | 201 | 8 |
| −1 | −3 | 7 | 141 | 143 | 7 |
| 1 | −3 | 7 | 177 | 166 | 8 |
| 3 | −3 | 7 | 225 | 233 | 12 |
| 5 | −3 | 7 | 149 | 132 | 9 |
| 7 | −3 | 7 | 233 | 226 | 13 |
| 9 | −3 | 7 | 69 | 58 | 14 |
| −24 | −2 | 7 | 30 | 33 | 29 |
| −22 | −2 | 7 | 70 | 48 | 12 |
| −20 | −2 | 7 | 143 | 127 | 7 |
| −18 | −2 | 7 | 65 | 57 | 10 |
| −16 | −2 | 7 | 180 | 182 | 6 |
| −14 | −2 | 7 | 154 | 167 | 5 |
| −12 | −2 | 7 | 140 | 141 | 4 |
| −10 | −2 | 7 | 266 | 246 | 15 |
| −8 | −2 | 7 | 152 | 150 | 10 |
| −6 | −2 | 7 | 242 | 252 | 15 |
| −4 | −2 | 7 | 225 | 294 | 13 |
| −2 | −2 | 7 | 208 | 193 | 12 |
| 0 | −2 | 7 | 160 | 160 | 12 |
| 4 | −2 | 7 | 80 | 83 | 5 |
| 6 | −2 | 7 | 204 | 207 | 8 |
| 8 | −2 | 7 | 0 | 15 | 1 |
| 10 | −2 | 7 | 193 | 210 | 8 |
| 12 | −2 | 7 | 60 | 74 | 6 |
| 14 | −2 | 7 | 130 | 119 | 7 |
| 16 | −2 | 7 | 55 | 58 | 5 |
| −25 | −1 | 7 | 73 | 65 | 9 |
| −23 | −1 | 7 | 35 | 82 | 35 |
| −21 | −1 | 7 | 104 | 108 | 14 |
| −19 | −1 | 7 | 258 | 252 | 10 |
| −17 | −1 | 7 | 154 | 157 | 6 |
| −15 | −1 | 7 | 388 | 397 | 11 |
| −13 | −1 | 7 | 157 | 152 | 10 |
| −11 | −1 | 7 | 360 | 291 | 19 |
| −9 | −1 | 7 | 814 | 760 | 43 |
| −7 | −1 | 7 | 783 | 724 | 40 |
| −5 | −1 | 7 | 915 | 845 | 48 |
| −3 | −1 | 7 | 102 | 115 | 7 |
| −1 | −1 | 7 | 218 | 207 | 8 |
| 1 | −1 | 7 | 0 | 28 | 1 |
| 3 | −1 | 7 | 500 | 522 | 29 |
| 5 | −1 | 7 | 475 | 492 | 13 |
| 7 | −1 | 7 | 285 | 276 | 9 |
| 9 | −1 | 7 | 142 | 142 | 8 |
| 11 | −1 | 7 | 271 | 269 | 13 |
| 13 | −1 | 7 | 36 | 21 | 14 |
| 15 | −1 | 7 | 55 | 51 | 8 |
| 17 | −1 | 7 | 0 | 31 | 1 |
| −26 | 0 | 7 | 29 | 41 | 29 |
| −24 | 0 | 7 | 0 | 5 | 1 |
| −22 | 0 | 7 | 63 | 72 | 13 |
| −20 | 0 | 7 | 45 | 52 | 22 |
| −18 | 0 | 7 | 98 | 94 | 11 |
| −16 | 0 | 7 | 55 | 82 | 14 |
| −14 | 0 | 7 | 159 | 160 | 12 |
| −12 | 0 | 7 | 274 | 228 | 15 |
| −10 | 0 | 7 | 312 | 305 | 17 |
| −8 | 0 | 7 | 176 | 158 | 7 |
| −6 | 0 | 7 | 263 | 307 | 15 |
| −4 | 0 | 7 | 750 | 803 | 34 |
| −2 | 0 | 7 | 750 | 790 | 27 |
| 0 | 0 | 7 | 805 | 867 | 41 |
| 2 | 0 | 7 | 451 | 519 | 23 |
| 4 | 0 | 7 | 88 | 81 | 11 |
| 6 | 0 | 7 | 156 | 153 | 5 |
| 8 | 0 | 7 | 193 | 174 | 6 |
| 10 | 0 | 7 | 360 | 348 | 9 |
| 12 | 0 | 7 | 70 | 65 | 6 |
| 14 | 0 | 7 | 0 | 18 | 1 |
| 16 | 0 | 7 | 9 | 45 | 8 |
| −25 | 1 | 7 | 59 | 66 | 15 |
| −23 | 1 | 7 | 63 | 62 | 14 |
| −21 | 1 | 7 | 114 | 108 | 10 |
| −19 | 1 | 7 | 277 | 253 | 13 |
| −17 | 1 | 7 | 154 | 156 | 10 |

TABLE 8-continued

Observed and calculated structure factors for 24F2-DM.

| h | k | l | 10Fo | 10Fc | 10s |
|---|---|---|------|------|-----|
| −15 | 1 | 7 | 375 | 397 | 19 |
| −9 | 1 | 7 | 831 | 760 | 42 |
| −7 | 1 | 7 | 788 | 722 | 40 |
| −5 | 1 | 7 | 944 | 844 | 47 |
| −3 | 1 | 7 | 119 | 116 | 9 |
| −1 | 1 | 7 | 223 | 207 | 12 |
| 1 | 1 | 7 | 0 | 26 | 1 |
| 3 | 1 | 7 | 566 | 522 | 26 |
| 6 | 2 | 9 | 521 | 517 | 18 |
| 8 | 2 | 9 | 220 | 236 | 13 |
| 10 | 2 | 9 | 126 | 140 | 6 |
| 12 | 2 | 9 | 62 | 60 | 18 |
| 14 | 2 | 9 | 0 | 23 | 1 |
| −3 | 3 | 9 | 98 | 113 | 10 |
| −1 | 3 | 9 | 357 | 362 | 19 |
| 1 | 3 | 9 | 308 | 293 | 15 |
| 3 | 3 | 9 | 368 | 363 | 18 |
| 5 | 3 | 9 | 211 | 206 | 8 |
| 7 | 3 | 9 | 82 | 79 | 7 |
| 9 | 3 | 9 | 59 | 64 | 17 |
| 11 | 3 | 9 | 69 | 50 | 8 |
| 13 | 3 | 9 | 76 | 69 | 6 |
| 2 | 4 | 9 | 139 | 142 | 10 |
| 4 | 4 | 9 | 94 | 95 | 10 |
| 6 | 4 | 9 | 0 | 20 | 1 |
| 8 | 4 | 9 | 92 | 73 | 9 |
| 10 | 4 | 9 | 64 | 55 | 8 |
| 7 | 5 | 9 | 31 | 29 | 30 |
| −8 | −6 | 10 | 128 | 126 | 6 |
| −6 | −6 | 10 | 24 | 22 | 24 |
| −4 | −6 | 10 | 56 | 57 | 10 |
| −2 | −6 | 10 | 34 | 50 | 20 |
| 0 | −6 | 10 | 0 | 13 | 1 |
| −17 | −5 | 10 | 0 | 37 | 1 |
| −15 | −5 | 10 | 59 | 72 | 9 |
| −13 | −5 | 10 | 37 | 46 | 36 |
| −11 | −5 | 10 | 52 | 45 | 9 |
| −9 | −5 | 10 | 90 | 83 | 6 |
| −7 | −5 | 10 | 80 | 68 | 9 |
| −5 | −5 | 10 | 51 | 59 | 30 |
| −3 | −5 | 10 | 0 | 25 | 1 |
| −1 | −5 | 10 | 115 | 137 | 8 |
| 1 | −5 | 10 | 157 | 159 | 10 |
| 3 | −5 | 10 | 126 | 132 | 9 |
| 5 | −5 | 10 | 86 | 101 | 8 |
| −22 | −4 | 10 | 46 | 43 | 10 |
| −20 | −4 | 10 | 71 | 63 | 7 |
| −18 | −4 | 10 | 93 | 97 | 6 |
| −16 | −4 | 10 | 83 | 79 | 6 |
| −14 | −4 | 10 | 110 | 111 | 4 |
| −12 | −4 | 10 | 198 | 196 | 6 |
| −10 | −4 | 10 | 133 | 130 | 13 |
| −8 | −4 | 10 | 17 | 20 | 17 |
| −6 | −4 | 10 | 68 | 71 | 6 |
| −4 | −4 | 10 | 51 | 37 | 11 |
| −2 | −4 | 10 | 306 | 330 | 15 |
| 0 | −4 | 10 | 134 | 141 | 9 |
| 2 | −4 | 10 | 175 | 172 | 11 |
| 4 | −4 | 10 | 52 | 45 | 16 |
| 6 | −4 | 10 | 18 | 44 | 18 |
| 8 | −4 | 10 | 68 | 77 | 11 |
| −23 | −3 | 10 | 139 | 120 | 13 |
| −21 | −3 | 10 | 102 | 93 | 10 |
| −19 | −3 | 10 | 191 | 189 | 9 |
| −17 | −3 | 10 | 52 | 54 | 9 |
| −15 | −3 | 10 | 262 | 295 | 8 |
| −13 | −3 | 10 | 268 | 257 | 6 |
| −11 | −3 | 10 | 30 | 34 | 10 |
| −9 | −3 | 10 | 85 | 77 | 9 |
| −7 | −3 | 10 | 132 | 145 | 5 |
| −5 | −3 | 10 | 182 | 173 | 8 |
| −3 | −3 | 10 | 165 | 162 | 7 |
| −1 | −3 | 10 | 105 | 96 | 11 |
| 1 | −3 | 10 | 257 | 238 | 13 |
| 3 | −3 | 10 | 369 | 376 | 18 |
| −26 | −2 | 10 | 73 | 68 | 11 |

TABLE 8-continued

Observed and calculated structure factors for 24F2-DM.

| h | k | l | 10Fc | 10Fc | 10s |
|---|---|---|------|------|-----|
| −24 | −2 | 10 | 75 | 56 | 7 |
| −22 | −2 | 10 | 53 | 44 | 9 |
| −20 | −2 | 10 | 20 | 22 | 19 |
| −18 | −2 | 10 | 35 | 37 | 16 |
| −16 | −2 | 10 | 41 | 61 | 13 |
| −14 | −2 | 10 | 162 | 157 | 6 |
| −12 | −2 | 10 | 256 | 247 | 6 |
| −10 | −2 | 10 | 116 | 102 | 8 |
| −8 | −2 | 10 | 299 | 288 | 7 |
| −6 | −2 | 10 | 256 | 249 | 7 |
| −4 | −2 | 10 | 143 | 144 | 7 |
| −2 | −2 | 10 | 92 | 81 | 6 |
| 0 | −2 | 10 | 164 | 172 | 8 |
| 2 | −2 | 10 | 152 | 157 | 7 |
| 4 | −2 | 10 | 108 | 110 | 7 |
| 6 | −2 | 10 | 59 | 61 | 6 |
| 8 | −2 | 10 | 28 | 34 | 16 |
| 10 | −2 | 10 | 116 | 104 | 6 |
| 12 | −2 | 10 | 23 | 26 | 16 |
| −14 | 2 | 12 | 42 | 34 | 25 |
| −12 | 2 | 12 | 91 | 108 | 10 |
| −10 | 2 | 12 | 67 | 58 | 12 |
| −8 | 2 | 12 | 119 | 135 | 9 |
| −6 | 2 | 12 | 243 | 238 | 13 |
| −4 | 2 | 12 | 230 | 244 | 10 |
| −2 | 2 | 12 | 138 | 135 | 12 |
| 0 | 2 | 12 | 73 | 71 | 8 |
| 2 | 2 | 12 | 273 | 294 | 20 |
| 4 | 2 | 12 | 109 | 112 | 10 |
| 6 | 2 | 12 | 195 | 209 | 8 |
| 8 | 2 | 12 | 89 | 86 | 6 |
| 10 | 2 | 12 | 63 | 58 | 6 |
| −9 | 3 | 12 | 142 | 150 | 11 |
| −7 | 3 | 12 | 163 | 172 | 13 |
| −5 | 3 | 12 | 57 | 51 | 16 |
| −3 | 3 | 12 | 149 | 142 | 12 |
| −1 | 3 | 12 | 112 | 98 | 9 |
| 1 | 3 | 12 | 130 | 143 | 7 |
| 3 | 3 | 12 | 75 | 74 | 9 |
| 5 | 3 | 12 | 120 | 126 | 11 |
| 7 | 3 | 12 | 79 | 70 | 7 |
| 9 | 3 | 12 | 65 | 66 | 6 |
| −4 | 4 | 12 | 76 | 66 | 11 |
| −2 | 4 | 12 | 63 | 58 | 13 |
| 0 | 4 | 12 | 94 | 89 | 10 |
| 2 | 4 | 12 | 85 | 83 | 9 |
| 4 | 4 | 12 | 60 | 48 | 11 |
| 6 | 4 | 12 | 38 | 29 | 18 |
| −17 | −5 | 13 | 60 | 55 | 10 |
| −15 | −5 | 13 | 134 | 118 | 12 |
| −13 | −5 | 13 | 102 | 78 | 11 |
| −11 | −5 | 13 | 87 | 68 | 6 |
| −9 | −5 | 13 | 112 | 94 | 5 |
| −7 | −5 | 13 | 132 | 117 | 10 |
| −5 | −5 | 13 | 80 | 78 | 9 |
| −3 | −5 | 13 | 57 | 52 | 11 |
| −1 | −5 | 13 | 58 | 56 | 10 |
| 1 | −5 | 13 | 56 | 61 | 10 |
| −20 | −4 | 13 | 94 | 82 | 11 |
| −18 | −4 | 13 | 27 | 50 | 27 |
| −16 | −4 | 13 | 43 | 44 | 12 |
| −14 | −4 | 13 | 172 | 160 | 20 |
| −12 | −4 | 13 | 125 | 134 | 6 |
| −10 | −4 | 13 | 196 | 222 | 12 |
| −8 | −4 | 13 | 114 | 130 | 6 |
| −6 | −4 | 13 | 108 | 116 | 5 |
| −4 | −4 | 13 | 39 | 41 | 27 |
| −2 | −4 | 13 | 56 | 55 | 14 |
| 0 | −4 | 13 | 82 | 85 | 10 |
| 2 | −4 | 13 | 80 | 70 | 10 |
| −23 | −3 | 13 | 55 | 39 | 7 |
| −21 | −3 | 13 | 148 | 131 | 6 |
| −19 | −3 | 13 | 118 | 134 | 6 |
| −17 | −3 | 13 | 52 | 59 | 8 |
| −15 | −3 | 13 | 43 | 59 | 9 |
| −13 | −3 | 13 | 60 | 73 | 9 |
| −11 | −3 | 13 | 117 | 110 | 7 |
| −9 | −3 | 13 | 80 | 81 | 7 |
| −7 | −3 | 13 | 296 | 280 | 21 |
| −5 | −3 | 13 | 178 | 199 | 24 |
| −3 | −3 | 13 | 158 | 160 | 10 |
| −26 | −2 | 13 | 93 | 70 | 6 |
| −24 | −2 | 13 | 38 | 35 | 13 |
| −22 | −2 | 13 | 42 | 52 | 10 |
| −20 | −2 | 13 | 121 | 137 | 5 |
| −18 | −2 | 13 | 111 | 137 | 5 |
| −16 | −2 | 13 | 190 | 178 | 7 |
| −14 | −2 | 13 | 87 | 87 | 6 |
| −12 | −2 | 13 | 310 | 283 | 7 |
| −10 | −2 | 13 | 154 | 143 | 4 |
| −8 | −2 | 13 | 119 | 124 | 5 |
| −6 | −2 | 13 | 240 | 232 | 8 |
| −4 | −2 | 13 | 117 | 122 | 7 |
| −2 | −2 | 13 | 197 | 186 | 9 |
| 0 | −2 | 13 | 79 | 84 | 6 |
| 2 | −2 | 13 | 41 | 54 | 9 |
| 4 | −2 | 13 | 36 | 46 | 11 |
| 6 | −2 | 13 | 153 | 146 | 7 |
| −27 | −1 | 13 | 43 | 55 | 17 |
| −25 | −1 | 13 | 92 | 82 | 7 |
| −23 | −1 | 13 | 95 | 89 | 8 |
| −21 | −1 | 13 | 83 | 91 | 6 |
| −19 | −1 | 13 | 126 | 124 | 6 |
| −17 | −1 | 13 | 257 | 248 | 7 |
| −15 | −1 | 13 | 181 | 190 | 6 |
| −13 | −1 | 13 | 39 | 40 | 24 |
| 0 | −2 | 16 | 0 | 15 | 1 |
| 2 | −2 | 16 | 83 | 67 | 6 |
| −25 | −1 | 16 | 101 | 85 | 5 |
| −23 | −1 | 16 | 63 | 52 | 7 |
| −21 | −1 | 16 | 80 | 75 | 8 |
| −19 | −1 | 16 | 50 | 48 | 9 |
| −17 | −1 | 16 | 135 | 152 | 5 |
| −15 | −1 | 16 | 314 | 331 | 9 |
| −13 | −1 | 16 | 258 | 272 | 13 |
| −11 | −1 | 16 | 243 | 237 | 11 |
| −9 | −1 | 16 | 312 | 151 | 8 |
| −7 | −1 | 16 | 174 | 213 | 6 |
| −5 | −1 | 16 | 219 | 16 | 7 |
| −3 | −1 | 16 | 29 | 16 | 28 |
| −1 | −1 | 16 | 161 | 153 | 8 |
| 1 | −1 | 16 | 65 | 68 | 8 |
| 3 | −1 | 16 | 57 | 55 | 8 |
| 5 | −1 | 16 | 52 | 40 | 7 |
| −26 | 0 | 16 | 70 | 48 | 7 |
| −24 | 0 | 16 | 34 | 7 | 25 |
| −22 | 0 | 16 | 112 | 109 | 14 |
| −20 | 0 | 16 | 51 | 60 | 9 |
| −18 | 0 | 16 | 160 | 183 | 11 |
| −16 | 0 | 16 | 81 | 100 | 9 |
| −14 | 0 | 16 | 534 | 561 | 34 |
| −12 | 0 | 16 | 98 | 86 | 6 |
| −10 | 0 | 16 | 363 | 337 | 12 |
| −8 | 0 | 16 | 102 | 102 | 12 |
| −6 | 0 | 16 | 144 | 149 | 7 |
| −4 | 0 | 16 | 12 | 21 | 11 |
| −2 | 0 | 16 | 123 | 132 | 7 |
| 0 | 0 | 16 | 9 | 35 | 8 |
| 2 | 0 | 16 | 96 | 93 | 7 |
| 4 | 0 | 16 | 94 | 78 | 6 |
| 6 | 0 | 16 | 26 | 14 | 25 |
| −23 | 1 | 16 | 74 | 51 | 11 |
| −21 | 1 | 16 | 95 | 75 | 10 |
| −19 | 1 | 16 | 36 | 49 | 36 |
| −17 | 1 | 16 | 151 | 153 | 11 |
| −15 | 1 | 16 | 322 | 236 | 11 |
| −13 | 1 | 16 | 262 | 270 | 12 |
| −11 | 1 | 16 | 225 | 236 | 14 |
| −9 | 1 | 16 | 309 | 299 | 16 |
| −7 | 1 | 16 | 164 | 152 | 13 |
| −5 | 1 | 16 | 176 | 212 | 9 |
| −3 | 1 | 16 | 20 | 14 | 19 |

TABLE 8-continued

Observed and calculated structure factors for 24F2-DM.

| h | k | l | 10Fc | 10Fc | 10s |
|---|---|---|------|------|-----|
| -1 | 1 | 16 | 159 | 153 | 18 |
| 1 | 1 | 16 | 77 | 68 | 6 |
| 3 | 1 | 16 | 58 | 56 | 11 |
| 5 | 1 | 16 | 26 | 40 | 23 |
| -20 | 2 | 16 | 13 | 36 | 13 |
| -18 | 2 | 16 | 80 | 94 | 11 |
| -16 | 2 | 16 | 208 | 189 | 12 |
| -14 | 2 | 16 | 192 | 190 | 13 |
| -12 | 2 | 16 | 221 | 193 | 13 |
| -10 | 2 | 16 | 339 | 338 | 17 |
| -8 | 2 | 16 | 81 | 79 | 8 |
| -6 | 2 | 16 | 94 | 98 | 17 |
| -4 | 2 | 16 | 10 | 21 | 10 |
| -2 | 2 | 16 | 48 | 63 | 9 |
| 0 | 2 | 16 | 28 | 15 | 28 |
| 2 | 2 | 16 | 88 | 67 | 5 |
| 4 | 2 | 16 | 0 | 23 | 1 |
| -15 | 3 | 16 | 0 | 51 | 1 |
| -13 | 3 | 16 | 187 | 174 | 11 |
| -11 | 3 | 16 | 67 | 40 | 15 |
| -9 | 3 | 16 | 63 | 69 | 14 |
| -7 | 3 | 16 | 63 | 83 | 12 |
| -5 | 3 | 16 | 109 | 118 | 6 |
| -3 | 3 | 16 | 88 | 99 | 6 |
| -1 | 3 | 16 | 77 | 77 | 7 |
| 1 | 3 | 16 | 60 | 53 | 7 |
| -8 | 4 | 16 | 0 | 25 | 1 |
| -6 | 4 | 16 | 0 | 22 | 1 |
| -4 | 4 | 16 | 28 | 29 | 27 |
| -2 | 4 | 16 | 61 | 60 | 9 |
| -18 | -4 | 16 | 20 | 32 | 19 |
| -16 | -4 | 17 | 64 | 67 | 6 |
| -14 | -4 | 17 | 62 | 61 | 7 |
| -12 | -4 | 17 | 156 | 141 | 6 |
| -10 | -4 | 17 | 43 | 48 | 8 |
| -8 | -4 | 17 | 59 | 52 | 13 |
| -6 | -4 | 17 | 50 | 52 | 14 |
| -21 | -3 | 17 | 0 | 15 | 1 |
| -19 | -3 | 17 | 51 | 60 | 10 |
| -17 | -3 | 17 | 75 | 74 | 7 |
| -15 | -3 | 17 | 84 | 83 | 6 |
| -8 | 0 | 20 | 14 | 22 | 13 |
| -6 | 0 | 20 | 49 | 29 | 11 |
| -4 | 0 | 20 | 62 | 45 | 8 |
| -23 | 1 | 20 | 50 | 29 | 14 |
| -21 | 1 | 20 | 42 | 46 | 21 |
| -19 | 1 | 20 | 34 | 27 | 21 |
| -17 | 1 | 20 | 0 | 14 | 1 |
| -15 | 1 | 20 | 65 | 78 | 8 |
| -13 | 1 | 20 | 55 | 56 | 10 |
| -11 | 1 | 20 | 82 | 70 | 11 |
| -9 | 1 | 20 | 91 | 88 | 6 |
| -7 | 1 | 20 | 116 | 109 | 6 |
| -5 | 1 | 20 | 32 | 34 | 32 |
| -20 | 2 | 20 | 72 | 60 | 9 |
| -18 | 2 | 20 | 0 | 43 | 1 |
| -16 | 2 | 20 | 0 | 39 | 1 |
| -14 | 2 | 20 | 66 | 53 | 9 |
| -12 | 2 | 20 | 0 | 7 | 1 |
| -10 | 2 | 20 | 55 | 48 | 10 |
| -8 | 2 | 20 | 41 | 56 | 13 |
| -6 | 2 | 20 | 0 | 15 | 1 |
| -15 | 3 | 20 | 12 | 16 | 11 |
| -13 | 3 | 20 | 82 | 85 | 9 |
| -11 | 3 | 20 | 0 | 6 | 1 |
| -9 | 3 | 20 | 0 | 29 | 1 |
| -16 | -2 | 21 | 44 | 38 | 12 |
| -14 | -2 | 21 | 53 | 19 | 9 |
| -12 | -2 | 21 | 48 | 25 | 11 |
| -10 | -2 | 21 | 17 | 4 | 17 |
| -8 | -2 | 21 | 26 | 23 | 26 |
| -21 | -1 | 21 | 35 | 32 | 20 |
| -19 | -1 | 21 | 38 | 45 | 20 |
| -17 | -1 | 21 | 79 | 59 | 9 |
| -15 | -1 | 21 | 91 | 75 | 7 |
| -13 | -1 | 21 | 44 | 53 | 14 |
| -11 | -1 | 21 | 64 | 71 | 9 |
| -9 | -1 | 21 | 43 | 31 | 12 |
| -7 | -1 | 21 | 40 | 35 | 12 |
| -22 | 0 | 21 | 26 | 4 | 25 |
| -20 | 0 | 21 | 26 | 10 | 25 |
| -18 | 0 | 21 | 0 | 1 | 1 |
| -16 | 0 | 21 | 91 | 72 | 6 |
| -14 | 0 | 21 | 41 | 46 | 12 |
| -12 | 0 | 21 | 104 | 87 | 6 |
| -8 | 0 | 21 | 20 | 16 | 20 |
| -6 | 0 | 21 | 36 | 9 | 14 |
| -21 | 1 | 21 | 44 | 33 | 16 |
| -19 | 1 | 21 | 36 | 46 | 20 |
| -17 | 1 | 21 | 67 | 59 | 7 |
| -15 | 1 | 21 | 78 | 75 | 6 |
| -13 | 1 | 21 | 50 | 54 | 10 |
| -11 | 1 | 21 | 68 | 71 | 7 |
| -9 | 1 | 21 | 44 | 30 | 10 |
| -7 | 1 | 21 | 27 | 35 | 27 |
| -18 | 2 | 21 | 27 | 32 | 26 |
| -16 | 2 | 21 | 36 | 37 | 18 |
| -14 | 2 | 21 | 0 | 18 | 1 |
| -12 | 2 | 21 | 23 | 25 | 23 |
| -10 | 2 | 21 | 0 | 4 | 1 |
| -8 | 2 | 21 | 6 | 23 | 6 |
| -18 | 0 | 22 | 16 | 31 | 16 |
| -16 | 0 | 22 | 40 | 40 | 40 |
| -14 | 0 | 22 | 29 | 7 | 28 |
| -17 | 1 | 22 | 33 | 31 | 14 |
| -15 | 1 | 22 | 68 | 34 | 10 |
| -13 | 1 | 22 | 86 | 76 | 6 |
| -11 | 1 | 22 | 68 | 71 | 8 |

REFERENCES

1. CrysAlis RED, Oxford Diffraction Ltd., Version 1.171.28 cycle2 beta (release 25-10-2005 CrysAlis171.NET) (compiled Oct. 25 2005, 08:50:05). Empirical absorption correction using spherical harmonics, implemented in SCALE3 ABSPACK scaling algorithm.
2. CrysAlis CCD, Oxford Diffraction Ltd., Version 1.171.28 cycle2 beta; CrysAlis RED, Oxford Diffraction Ltd., Version 1.171.28 cycle2 beta.
3. G. M. Sheidrick, Acta Crystallogr. 1990, A46, 467-473.
4. G. M. Sheldrick, SHELXL93. *Program for the Reminement of Crystal Structures*, Univ. of Götttingen, Germany.
5. *International Tables for Crystallography*, Ed. A. J. C. Wilson, Kluwer:Dordrecth, 1992, Vol. C.

Example 2

Synthesis of 24F2-DM

The preparation of 24F2-DM having the basic structure I can be accomplished by a common general method otherwise referred to as the condensation of a bicyclic Windaus-Grundmann type ketone II with the allylic phosphine oxide III to the corresponding 19-nor-vitamin D analog IV followed by deprotection at C-1 and C-3 in the latter compound IV to obtain compound I (24F2-DM).

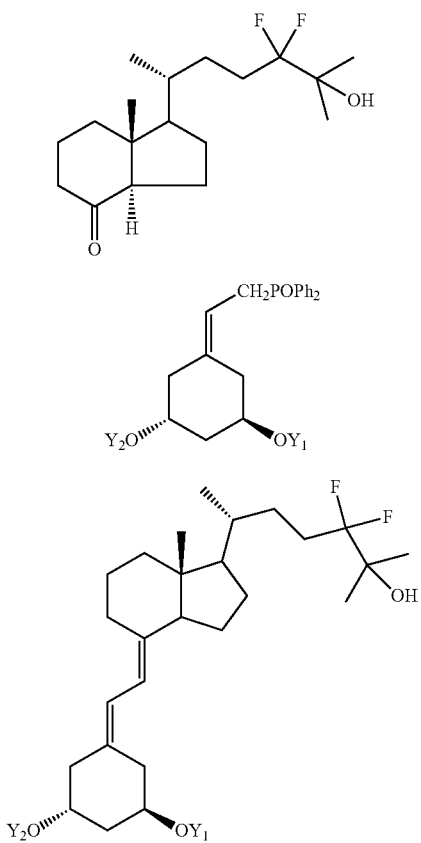

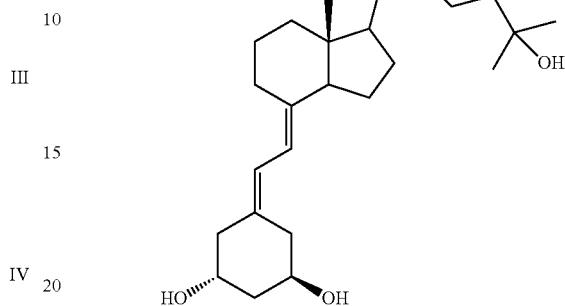

In phosphine oxide III, $Y_1$ and $Y_2$ are preferably hydroxy-protecting groups such as silyl protecting groups. The t-butyldimethylsilyl (TMDMS) group is an example of a particularly useful hydroxy-protecting group. The process described above represents an application of the convergent synthesis concept, which has been applied effectively to the preparation of numerous vitamin D compounds (see Lythgoe et al., *J. Chem. Soc. Perkin Trans.* 1, 590 (1978); Lythgoe, *Chem. Soc. Rev.* 9, 449 (1983); Toh et al., *J. Org. Chem.* 48, 1414 (1983); Baggiolini et al., *J. Org. Chem.* 51, 3098 (1986); Sardina et al., *J. Org. Chem.* 51, 1264 (1986); *J. Org. Chem.* 51, 1269 (1986); DeLuca et al., U.S. Pat. No. 5,086,191; DeLuca et al., U.S. Pat. No. 5,536,713; and DeLuca et al., U.S. Pat. No. 5,843,928 all of which are hereby incorporated by reference in their entirety and for all purposes as if fully set forth herein.

Phosphine oxide III is a convenient reagent that can be used to prepare a large number of 19-nor-vitamin D compounds and is prepared according to the procedures described by Sicinski et al., *J. Med. Chem.*, 41, 4662 (1998), DeLuca et al., U.S. Pat. No. 5,843,928; Perlman et al., *Tetrahedron Lett.* 32, 7663 (1991); and DeLuca et al., U.S. Pat. No. 5,086,191 which are hereby incorporated by reference in their entirety as if fully set forth herein.

An overall process for the synthesis of compound I is illustrated and described more completely in U.S. Pat. No. 5,843,928 entitled "2-Alkylidene-19-Nor-Vitamin D Compounds," the specification of which is specifically incorporated herein by reference.

We claim:

1. A compound having the formula

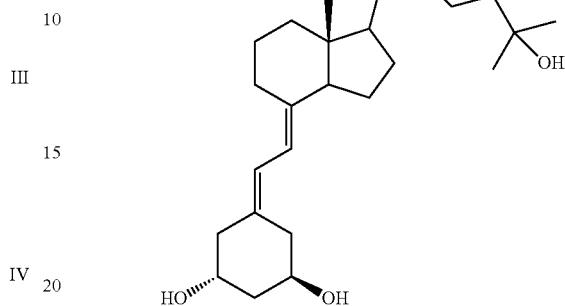

in crystalline form, and named (20R)-19-nor-24-difluoro-1α,25-dihydroxyvitamin $D_3$, wherein the crystalline form has a molecular packing arrangement defined by space group C2 and unit cell dimensions a=23.88 Å, b=6.16 Å, c=19.63 Å, α=90°, β=121.83° and γ=90°.

2. A three dimensional structure for (20R)-9-nor-24-difluoro-1α,25-dihydroxyvitamin D as defined by the molecular packing arrangement set forth in claim 1.

3. A method of purifying (20R)-19-nor-24-difluoro-1α,25-dihydroxyvitamin $D_3$, comprising the steps of:

(a) preparing a solvent comprising hexane;

(b) adding a product containing (20R)-9-nor-24-difluoro-1α,25-dihydroxyvitamin $D_3$ to be purified to said hexane to form a suspension of the product in the hexane;

(c) adding 2-propanol dropwise to the suspension to form a mixture of the product in the hexane and 2-propanol;

(d) heating the mixture to dissolve the product containing (20R)-19-nor-24-difluoro-1α,25-dihydroxyvitamin D- to be purified in said mixture;

(e) cooling said mixture and dissolved product below ambient temperature for a sufficient amount of time to form a precipitate of (20R)-19-nor-24-difluoro-1α,25-dihydroxyvitamin D crystals; and (f) separating the (20R)-19-nor-24-difluoro-1α,25-dihydroxyvitamin $D_3$ crystals from the solvent.

4. The method of claim 3 including the further step of allowing said solvent and dissolved product to cool to ambient temperature prior to cooling below ambient temperature.

5. The method of claim 3 wherein the step of separating comprises filtering the mixture and precipitate to obtain the crystals.

6. The method of claim 3 including, a further step (g) comprising repeating steps (a) through (f) using the recovered crystals from step (f) as the product of step (b).

7. The method of claim 3 wherein said mixture comprises about 15% 2-propanol and about 85% hexane by volume.

\* \* \* \* \*